United States Patent
Paul et al.

(10) Patent No.: US 9,899,037 B2
(45) Date of Patent: Feb. 20, 2018

(54) SYSTEM AND METHOD FOR EMOTION ASSESSMENT

(71) Applicant: Lena Foundation, Boulder, CO (US)

(72) Inventors: Terrance D. Paul; Dongxin D. Xu, Boulder, CO (US); Sharmistha Sarkar Gray, Dracut, MA (US); Umit Yapanel, Sunnyvale, CA (US); Jill S. Gilkerson, Boulder, CO (US); Jeffrey A. Richards, Boulder, CO (US)

(73) Assignee: LENA FOUNDATION, Boulder, CO (US)

( * ) Notice: Subject to any disclaimer, the term of this patent is extended or adjusted under 35 U.S.C. 154(b) by 0 days.

(21) Appl. No.: 14/997,179

(22) Filed: Jan. 15, 2016

(65) Prior Publication Data
US 2016/0210986 A1    Jul. 21, 2016

Related U.S. Application Data

(60) Division of application No. 12/359,124, filed on Jan. 23, 2009, now Pat. No. 9,240,188, which is a
(Continued)

(51) Int. Cl.
*G10L 15/00* (2013.01)
*G10L 15/04* (2013.01)
(Continued)

(52) U.S. Cl.
CPC .............. *G10L 25/63* (2013.01); *G10L 15/02* (2013.01); *G10L 15/075* (2013.01); *G10L 15/14* (2013.01); *G10L 2015/022* (2013.01)

(58) Field of Classification Search
CPC combination set(s) only.
See application file for complete search history.

(56) References Cited

U.S. PATENT DOCUMENTS

| 4,087,632 A | 5/1978 | Hafer |
| 4,139,732 A | 2/1979 | Fourcin |

(Continued)

FOREIGN PATENT DOCUMENTS

| EP | 0896319 | 2/1999 |
| EP | 2248077 | 11/2010 |

(Continued)

OTHER PUBLICATIONS

Huang et al. "Advances in Unsupervised Audio Classification and Segmentation for the Broadcast News and NGSW Corpora." IEEE Transactions on Audio, Speech, and Language Processing. vol. 14, No. 3. May 2006.*

(Continued)

*Primary Examiner* — Jialong He
(74) *Attorney, Agent, or Firm* — Bryan Cave LLP

(57) ABSTRACT

A method of determining an emotion of an utterance. The method can include receiving the utterance at a processor-based device comprising an audio engine. The method also can include extracting emotion-related acoustic features from the utterance. The method additionally can include comparing the emotion-related acoustic features to a plurality of emotion models that are representative of emotions. The method further can include selecting a model from the plurality of emotion models based on the comparing the emotion-related acoustic features to the plurality of emotion models. The method additionally can include outputting the emotion of the utterance, wherein the emotion corresponds to the selected model. Other embodiments are provided.

20 Claims, 33 Drawing Sheets

Related U.S. Application Data continuation-in-part of application No. 12/109,785, filed on Apr. 25, 2008, now Pat. No. 8,744,847, which is a continuation-in-part of application No. 12/018,647, filed on Jan. 23, 2008, now Pat. No. 8,078,465.

(60) Provisional application No. 60/886,122, filed on Jan. 23, 2007, provisional application No. 60/886,167, filed on Jan. 23, 2007.

(51) Int. Cl.
 *G09B 19/04* (2006.01)
 *G10L 25/63* (2013.01)
 *G10L 15/02* (2006.01)
 *G10L 15/14* (2006.01)
 *G10L 15/07* (2013.01)

(56) References Cited

U.S. PATENT DOCUMENTS

| | | |
|---|---|---|
| 4,408,616 A | 10/1983 | Duffy et al. |
| 4,464,119 A | 8/1984 | Vildgrube et al. |
| 4,675,904 A | 6/1987 | Silverman |
| 4,809,332 A | 2/1989 | Jongman et al. |
| 4,852,181 A | 7/1989 | Morito et al. |
| 4,857,030 A | 8/1989 | Rose |
| 4,903,304 A | 2/1990 | Schlang et al. |
| 5,014,327 A | 5/1991 | Potter et al. |
| 5,033,087 A | 7/1991 | Bahl et al. |
| 5,167,004 A | 11/1992 | Netsch et al. |
| 5,169,316 A | 12/1992 | Lorman et al. |
| 5,260,869 A | 11/1993 | Ferrier et al. |
| 5,459,815 A | 10/1995 | Aikawa et al. |
| 5,479,576 A * | 12/1995 | Watanabe ............... G06N 3/08 700/1 |
| 5,497,447 A | 3/1996 | Bahl et al. |
| 5,572,624 A | 11/1996 | Sejnoha |
| 5,598,507 A | 1/1997 | Kimber |
| 5,617,855 A | 4/1997 | Waletzky et al. |
| 5,659,662 A | 8/1997 | Wilcox et al. |
| 5,679,001 A | 10/1997 | Russell et al. |
| 5,717,828 A | 2/1998 | Rothenberg |
| 5,729,658 A | 3/1998 | Hou et al. |
| 5,765,127 A | 6/1998 | Nishiguchi et al. |
| 5,812,972 A | 9/1998 | Juang et al. |
| 5,813,862 A | 9/1998 | Merzenich et al. |
| 5,873,728 A | 2/1999 | Jeong et al. |
| 5,878,392 A | 3/1999 | Meyer et al. |
| 5,884,259 A | 3/1999 | Bahl et al. |
| 5,890,113 A | 3/1999 | Takagi |
| 5,893,720 A | 4/1999 | Cohen |
| 5,913,188 A | 6/1999 | Tzirkel-Hancock |
| 5,927,988 A | 7/1999 | Jenkins et al. |
| 5,953,701 A | 9/1999 | Neti et al. |
| 5,960,397 A | 9/1999 | Rahim |
| 5,964,593 A | 10/1999 | Cohen |
| 5,966,691 A | 10/1999 | Kibre et al. |
| 5,978,759 A | 11/1999 | Tsushima et al. |
| 6,006,188 A | 12/1999 | Bogdashevsky et al. |
| 6,018,706 A | 1/2000 | Huang et al. |
| 6,029,124 A | 2/2000 | Gillick et al. |
| 6,061,646 A | 5/2000 | Martino et al. |
| 6,071,123 A | 6/2000 | Tallal et al. |
| 6,073,095 A | 6/2000 | Dharanipragada et al. |
| 6,123,548 A | 9/2000 | Tallal et al. |
| 6,134,529 A | 10/2000 | Rothenberg |
| 6,157,913 A | 12/2000 | Bernstein |
| 6,173,260 B1 | 1/2001 | Slaney |
| 6,212,502 B1 | 4/2001 | Ball et al. |
| 6,246,985 B1 | 6/2001 | Kanevsky et al. |
| 6,253,173 B1 * | 6/2001 | Ma ...................... G10L 15/30 704/222 |
| 6,253,181 B1 | 6/2001 | Junqua |
| 6,296,489 B1 | 10/2001 | Blass et al. |
| 6,304,846 B1 | 10/2001 | George et al. |
| 6,336,089 B1 | 1/2002 | Everding |
| 6,341,267 B1 | 1/2002 | Taub |
| 6,364,666 B1 | 4/2002 | Jenkins et al. |
| 6,395,482 B1 | 5/2002 | Karayiorgou et al. |
| 6,404,925 B1 | 6/2002 | Foote et al. |
| 6,405,167 B1 | 6/2002 | Cogliano |
| 6,468,084 B1 | 10/2002 | MacMillan |
| 6,539,352 B1 | 3/2003 | Sharma et al. |
| 6,554,617 B1 | 4/2003 | Dolan |
| 6,584,440 B2 | 6/2003 | Litovsky |
| 6,661,345 B1 | 12/2003 | Bevan et al. |
| 6,662,162 B2 | 12/2003 | Casper |
| 6,665,642 B2 | 12/2003 | Kanevsky et al. |
| 6,676,412 B1 | 1/2004 | Masterston et al. |
| 6,697,778 B1 | 2/2004 | Kuhn et al. |
| 6,721,706 B1 | 4/2004 | Strubbe et al. |
| 6,725,198 B2 | 4/2004 | Waryas et al. |
| 6,732,076 B2 | 5/2004 | Masterson et al. |
| 6,774,917 B1 | 8/2004 | Foote |
| 6,807,395 B2 | 10/2004 | Iwazaki et al. |
| 7,011,525 B2 | 3/2006 | Mejia |
| 7,013,276 B2 | 3/2006 | Bickley et al. |
| 7,063,535 B2 | 6/2006 | Stamm et al. |
| 7,143,044 B2 | 11/2006 | Zadrozny et al. |
| 7,180,892 B1 | 2/2007 | Tackin |
| 7,184,959 B2 | 2/2007 | Gibbon et al. |
| 7,272,559 B1 | 9/2007 | Hayre |
| 7,275,034 B2 | 9/2007 | Odell et al. |
| 7,295,970 B1 | 11/2007 | Gorin et al. |
| 7,457,753 B2 | 11/2008 | Moran et al. |
| 7,590,513 B2 | 9/2009 | Jiang et al. |
| 7,603,276 B2 | 10/2009 | Yoshizawa |
| 7,627,475 B2 | 12/2009 | Petrushin |
| 7,711,652 B2 | 5/2010 | Schmelzer |
| 7,720,012 B1 | 5/2010 | Borah et al. |
| 7,826,981 B2 | 11/2010 | Goode, Jr. et al. |
| 7,914,468 B2 | 3/2011 | Shalon et al. |
| 7,930,179 B1 | 4/2011 | Gorin et al. |
| 8,009,193 B2 | 8/2011 | Zhou et al. |
| 8,078,465 B2 | 12/2011 | Paul et al. |
| 8,402,026 B2 * | 3/2013 | Gallivan ............. G06F 17/3071 707/737 |
| 8,744,847 B2 | 6/2014 | Paul et al. |
| 2002/0052741 A1 | 5/2002 | Seo et al. |
| 2002/0150869 A1 | 10/2002 | Shpiro |
| 2003/0009333 A1 | 1/2003 | Sharma et al. |
| 2003/0033145 A1 | 2/2003 | Petrushin |
| 2003/0074191 A1 | 4/2003 | Byrnes et al. |
| 2003/0088565 A1 | 5/2003 | Walter et al. |
| 2003/0125099 A1 * | 7/2003 | Basson ................. A63F 13/10 463/7 |
| 2003/0144839 A1 | 7/2003 | Dharanipragada et al. |
| 2003/0171924 A1 | 9/2003 | Bi et al. |
| 2004/0019484 A1 | 1/2004 | Kobayashi et al. |
| 2004/0068406 A1 | 4/2004 | Maekawa et al. |
| 2004/0111263 A1 | 6/2004 | Nishitani et al. |
| 2004/0143434 A1 | 7/2004 | Divakaran et al. |
| 2004/0197750 A1 | 10/2004 | Donaher et al. |
| 2004/0199386 A1 | 10/2004 | Attias et al. |
| 2004/0215449 A1 | 10/2004 | Roy |
| 2004/0220493 A1 * | 11/2004 | Teicher ................ A61B 5/1127 600/558 |
| 2004/0236573 A1 | 11/2004 | Sapeluk |
| 2004/0236577 A1 | 11/2004 | Nishitani et al. |
| 2005/0064375 A1 * | 3/2005 | Blank .................. G09B 17/003 434/178 |
| 2005/0096907 A1 | 5/2005 | Bacchiani et al. |
| 2005/0102135 A1 * | 5/2005 | Goronzy ................ G10L 15/00 704/213 |
| 2005/0112534 A1 | 5/2005 | McCarton et al. |
| 2005/0131688 A1 | 6/2005 | Goronzy et al. |
| 2005/0137862 A1 | 6/2005 | Monkowski |
| 2005/0142522 A1 | 6/2005 | Kullok et al. |
| 2005/0170333 A1 * | 8/2005 | Vojdani ............... C07K 16/2851 435/5 |
| 2005/0176057 A1 | 8/2005 | Bremer et al. |
| 2005/0187770 A1 | 8/2005 | Kompe et al. |
| 2005/0228236 A1 | 10/2005 | Diederich et al. |

(56) References Cited

U.S. PATENT DOCUMENTS

| | | | |
|---|---|---|---|
| 2005/0251532 | A1 | 11/2005 | Radhakrishnan et al. |
| 2006/0020458 | A1 | 1/2006 | Kwon et al. |
| 2006/0028556 | A1 | 2/2006 | Bunn et al. |
| 2006/0041427 | A1 | 2/2006 | Yegnanarayanan et al. |
| 2006/0052428 | A1 | 3/2006 | Chez |
| 2006/0052945 | A1 | 3/2006 | Rabinowitz et al. |
| 2006/0053014 | A1 | 3/2006 | Yoshizawa |
| 2006/0058998 | A1 | 3/2006 | Yamamoto et al. |
| 2006/0058999 | A1 | 3/2006 | Barker et al. |
| 2006/0069566 | A1* | 3/2006 | Fukada .................. G10L 13/06 704/260 |
| 2006/0074656 | A1 | 4/2006 | Mathias et al. |
| 2006/0093997 | A1 | 5/2006 | Kearby et al. |
| 2006/0105305 | A1 | 5/2006 | Stewart |
| 2006/0136217 | A1 | 6/2006 | Mullin |
| 2006/0149558 | A1 | 7/2006 | Kahn et al. |
| 2006/0206724 | A1 | 9/2006 | Schaufele et al. |
| 2006/0212296 | A1 | 9/2006 | Espy-Wilson et al. |
| 2006/0278532 | A1 | 12/2006 | Goldknopf et al. |
| 2007/0009865 | A1 | 1/2007 | Palacios |
| 2007/0010998 | A1 | 1/2007 | Radhakrishnan et al. |
| 2007/0055151 | A1 | 3/2007 | Shertukde et al. |
| 2007/0110042 | A1 | 5/2007 | Li et al. |
| 2007/0112764 | A1 | 5/2007 | Yih et al. |
| 2007/0124135 | A1 | 5/2007 | Schultz |
| 2007/0168187 | A1 | 7/2007 | Fletcher et al. |
| 2007/0172805 | A1* | 7/2007 | Paul ........................ G09B 5/00 434/308 |
| 2007/0198263 | A1 | 8/2007 | Chen |
| 2007/0239441 | A1 | 10/2007 | Navratil et al. |
| 2008/0045805 | A1 | 2/2008 | Sarel et al. |
| 2008/0063264 | A1 | 3/2008 | Porikli et al. |
| 2008/0082337 | A1 | 4/2008 | Joublin et al. |
| 2008/0096172 | A1 | 4/2008 | Brumfield et al. |
| 2008/0133141 | A1 | 6/2008 | Frost |
| 2008/0133221 | A1 | 6/2008 | Smith |
| 2008/0159560 | A1 | 7/2008 | Song et al. |
| 2008/0208581 | A1 | 8/2008 | Pelecanos et al. |
| 2008/0235016 | A1* | 9/2008 | Paul ..................... G06N 99/005 704/246 |
| 2008/0235017 | A1 | 9/2008 | Satomura |
| 2008/0243503 | A1 | 10/2008 | Soong et al. |
| 2009/0024050 | A1 | 1/2009 | Jung et al. |
| 2009/0155751 | A1 | 6/2009 | Paul et al. |
| 2009/0191521 | A1 | 7/2009 | Paul et al. |
| 2009/0208913 | A1 | 8/2009 | Xu et al. |
| 2010/0204993 | A1 | 8/2010 | Vogt |
| 2014/0255887 | A1 | 9/2014 | Xu et al. |
| 2016/0203832 | A1* | 7/2016 | Paul ........................ G10L 17/16 704/201 |

FOREIGN PATENT DOCUMENTS

| | | |
|---|---|---|
| WO | 1994010666 | 5/1994 |
| WO | 2000070584 | 11/2000 |
| WO | 2006034029 | 3/2006 |
| WO | 2009094039 | 7/2009 |

OTHER PUBLICATIONS

Xu, Dongxin, et al. "Signal processing for young child speech language development." First Workshop on Child, Computer and Interaction. Oct. 2008.*

Howlin, Patricia, Lynn Mawhood, and Michael Rutter. "Autism and developmental receptive language disorder—A follow-up comparison in early adult life. II: Social, behavioural, and psychiatric outcomes." The Journal of Child Psychology and Psychiatry and Allied Disciplines 41.5 (2000): 561-578.*

Abedi, Jamal. "The no child left behind act and English language learners: Assessment and accountability issues." Educational Researcher 33.1 (2004): 4-14.*

Xu Dongxin et al. "Reliability of the LENA Language Environment Analysis System in Young Children's Natural Home Environment", LENA Foundation, Boulder, CO, Feb. 2009.*

Ajmera et al.; "Speech/music segmentation using entropy and dynamism features in a HMM classification framework"; Speech Communication, 2003; Elsevier Science B.V. 2002; 40:351-363.

Baron-Cohen et al.; "Can autism be detected at 18 months? The needle, the haystack, and the CHAT"; British Journal of Psychiatry; vol. 161; Dec. 1992; pp. 839-843.

Brown; "A First Language: The Early Stages"; Harvard University Press; Jun. 1973.

Fell et al.; "Analysis of Infant Babble by the Early Vocalization Analyzer"; presented at the American Speech-Language-Hearing Convention; Nov. 17, 2000.

Fell et al.; "Automatic Babble Recognition for Early Detection of Speech Related Disorders"; Proceedings of the Third International ACM SIGCAPH Conference on Assistive Technologies; Apr. 15-17, 1998; Marina Del Rey, CA.

Fell et al.; "EVA, an Early Vocalization Analyzer—An Empirical Validity Study of Computer Categorization"; ftp.cs.rpl.edu/pub/assets96/papers/ascii/Fell.txt., accessed Jul. 18, 2008.

Fell et al.; "Using Early Vocalization Analysis for Visual Feedback," 2003.

Fell et al.; "Vocalization Age as a Clinical Tool"; presented at the 7th International Conference on Spoken Language Processing; Sep. 16-20, 2002; Denver, CO.

Fredouille et al.; "Application of Automatic Speaker Recognition techniques to pathological voice assessment (dysphona)"; Author Manuscript; Consultez L'Archive Half-Vous; 2007.

Harriet Fell's Home Page; www.ccs.neu.edu/home/fell, accessed Jul. 18, 2008.

Huang et al.; A Mandarin Speech Dictation System Based on Neural Network and Language Processing Model; IEEE Transactions on Consumer Electronics, Aug. 1994; 40(3).

International Search Report in co-pending PCT Application No. PCT/US05/33155, dated Mar. 15, 2006, 15 pages.

International Search Report in co-pending PCT Application No. PCT/US10/21852, dated Mar. 26, 2010, 6 pages.

Joel MacAuslan, PhD; Founder and President; biography, undated.

Loveland et al.; "Joint attention and language in autism and developmental language delay"; Springer Netherlands; vol. 16, No. 3, Sep. 1986; pp. 335-349.

Magrin-Chagnolleau et al., "Detection of a Target Speakers in Audio Databases," 1999 IEEE International Conference on Acoustics, Speech, and Signal Processing; Mar. 15-19, 1999, Phoenix, AZ; 821-824.

Mahdhaoui et al.; "Automatic Motherese Detection for Face-to-Face Interaction Analysis"; Multimodal Signals; LNAI 5398; Springer-Verlag Berlin Heidelberg: 2009; 2489-255.

Mahdhaoui et al.; "Motherese Detection Based on Segmental and Supra-Segmental Features"; IEEE, 2008.

Miller et al.; "The Relation Between Age and Mean Length of Utterance in Morphemes"; Journal of Speech and Hearing Research; vol. 24; Jun. 1981; pp. 154-161.

Morris, Suzanne Evans; "Pre-Speech Assessment Scale: A Rating Scale for the Measurement of Pre-Speech Behaviors from Birth through Two Years"; J.A. Preston Corporation; 1982 edition.

Mundy et al.; Nonverbal communication, affective sharing, and intersubjectivity; Infant Behavior & Development; Elsevier, New York, New York; vol. 15, No. 3, 1992; pp. 377-381.

Munson, B.; "A method for studying variability in fricatives using dynamic measures of spectral mean," Journal of the Acoustical Society of America, vol. 110, Issue 2; Aug. 2001.

MVDR Based Feature Extraction for Robust Speech Recognition; Tech TIPS Technology Case; University of California, San Diego; Invent.ucsd.edu/technology/cases/2001/sd2001-138.html, 2001.

Nittrouer et al.; "Developmental weighting shifts for noise components of fricative-vowel syllables," Journal of the Acoustical Society of America, vol. 102, Issue 1; Jul. 1997.

(56) References Cited

OTHER PUBLICATIONS

Northeastern University College of Computer and Information Science—Faculty Members; www.ccs.neu.edu/groups/faculty/fell.html, accessed Jul. 18, 2008.

Paul et al.; "Perception and Production of Prosody by Speakers With Autism Spectrum Disorders"; Springer Netherlands; vol. 35, No. 2; Apr. 2005; pp. 205-220.

Petitto et al.; "Babbling in the manual mode: evidence for the ontogeny of language," American Association for the Advance of Science, vol. 251, Issue n5000; Mar. 22, 1991.

Pronovost et al.; "A longitudinal study of the speech behavior and language comprehension of fourteen children diagnosed atypical or autistic"; Exceptional Children; vol. 33, No. 1; pp. 19-26, 1966.

Samuel; "Instructional Resources for Pronunciation Practice"; www.utoronto.ca/writing/pronunciation.html, accessed Jul. 18, 2008.

Scheffler et al.; "Screening for communication and cognitive disorders in infants and toddlers," Pediatric Nursing, vol. 33, Issue 6; Nov. 2007.

Sheinkopf et al.; "Vocal Atypicalities of Preverbal Autistic Children"; Journal of Autism and Developmental Disorders; vol. 30, No. 4; Aug. 2000; pp. 345-354.

Slaney et al.; "BabyEars: A recognition system for affective vocalizations," Speech Communications, 2003; 29:367-384.

The Guide to Computing Literature; portal.acm.org/results.cfm?query+author, accessed Jul. 18, 2008.

Yapanel et al.; "A New Perceptually Motivated MVDR-Based Acoustic Front-End (PMVDR) for Robust Automatic Speech Recognition"; The Center for Spoken Language Research; University of Colorado at Boulder; Jun. 21, 2004.

Sugiyama et al., "Speech Segmentation and Clustering Based on Speaker Features," Proc. Int. Conf. Acoustics, Speech and Signal Processing, Apr. 1993, vol. 2, pp. 395-398.

Murthy et al., "Automatic segmentation and labeling of continuous speech without bootstrapping." Proc. of EUSIPCO. 2004.

Morris, Suzanne E. "Pre-Speech Assessment Scale: A Rating Scale for Measurement of Pre-Speech Behaviors from Birth through Two Years". 1982.

\* cited by examiner

| "Phone" | Corr | "Phone" | Corr | "Phone" | Corr |
|---|---|---|---|---|---|
| R | 0.71 | W | 0.22 | G | -0.12 |
| ER | 0.65 | DH | 0.22 | D | -0.12 |
| AW | 0.61 | AY | 0.19 | V | -0.21 |
| IY | 0.55 | M | 0.18 | OW | -0.22 |
| Y | 0.53 | CH | 0.17 | AO | -0.22 |
| L | 0.47 | OY | 0.14 | K | -0.24 |
| N | 0.45 | TH | 0.10 | P | -0.25 |
| SH | 0.36 | ZH | 0.10 | T | -0.26 |
| S | 0.36 | AE | 0.01 | IH | -0.33 |
| Z | 0.33 | UH | 0.01 | AA | -0.38 |
| HH | 0.33 | EH | -0.02 | EY | -0.48 |
| JH | 0.29 | UW | -0.04 | B | -0.55 |
| NG | 0.27 | F | -0.06 | AH | -0.57 |

Figure 13

| Phone | All Ages | 0-6 Months | 7-13 Months | 14-20 Months | 21-30 Months | 31+ Months |
|---|---|---|---|---|---|---|
| R | 0.71 | 0.02 | 0.12 | 0.36 | 0.35 | 0.12 |
| ER | 0.65 | 0.08 | 0.11 | 0.25 | 0.28 | -0.01 |
| AW | 0.62 | -0.19 | 0.02 | 0.33 | 0.13 | 0.02 |
| AH | -0.57 | -0.06 | -0.13 | -0.21 | -0.24 | -0.02 |
| B | -0.56 | 0.05 | -0.05 | -0.24 | -0.25 | 0.00 |
| IY | 0.55 | 0.04 | 0.06 | 0.22 | 0.30 | 0.20 |
| Y | 0.53 | 0.14 | 0.11 | 0.15 | 0.18 | 0.09 |
| EY | -0.48 | 0.13 | -0.16 | -0.17 | -0.03 | -0.05 |
| L | 0.48 | 0.09 | 0.10 | 0.19 | -0.02 | -0.05 |
| N | 0.45 | -0.05 | 0.18 | 0.06 | 0.19 | -0.09 |
| AA | -0.38 | -0.20 | -0.23 | -0.12 | -0.02 | -0.01 |
| SH | 0.37 | 0.14 | 0.06 | 0.13 | 0.15 | -0.09 |
| S | 0.36 | -0.04 | 0.02 | 0.27 | 0.09 | -0.08 |
| IH | -0.34 | 0.05 | -0.08 | -0.13 | -0.09 | 0.28 |
| Z | 0.34 | -0.05 | 0.00 | 0.18 | 0.11 | -0.14 |
| HH | 0.33 | 0.20 | 0.04 | 0.08 | -0.02 | -0.06 |

Figure 14

|  | phone | 6 months | 12 months | 18 months | 24 months | 36 months |
|---|---|---|---|---|---|---|
| $b_1$ | +BREATH+ | 3.125557 | 7.377753 | -6.394588 | -2.83189 | 34.63505 |
| $b_2$ | +COUGH+ | -4.479990 | -9.036144 | -9.197089 | -8.54507 | -6.78925 |
| $b_3$ | +NOISE+ | -5.330784 | -5.571879 | 1.612521 | 4.17991 | 1.52012 |
| $b_4$ | +SMACK+ | 6.954375 | 5.760466 | 2.148514 | 3.11875 | 5.60514 |
| $b_5$ | +UH+ | 8.527651 | -5.105363 | -13.452590 | -14.05091 | -23.02752 |
| $b_6$ | +UM+ | -7.152641 | -10.685700 | 24.974180 | 9.81340 | -58.82121 |
| $b_7$ | SILENCE | -1.413627 | 7.098048 | 7.206686 | 4.44607 | -2.78011 |
| $b_8$ | AA | 7.685157 | -13.806020 | 31.287880 | 46.80778 | -29.55611 |
| $b_9$ | AE | -0.774203 | -6.584876 | -2.210732 | 16.40878 | -1.02520 |
| $b_{10}$ | AH | 0.271203 | -0.499897 | -11.033600 | -12.38318 | 6.53627 |
| $b_{11}$ | AO | 19.243300 | 29.924390 | -12.351380 | -31.07597 | 28.75396 |
| $b_{12}$ | AW | 2.175357 | 43.165320 | -10.289460 | -42.24812 | -23.92788 |
| $b_{13}$ | AY | -40.747460 | -24.235270 | -14.013280 | -15.01908 | -12.15185 |
| $b_{14}$ | B | 2.108008 | 7.698441 | 3.280957 | 5.91572 | 3.17980 |
| $b_{15}$ | CH | -239.702000 | -29.131360 | 10.236920 | -6.85704 | -52.90835 |
| $b_{16}$ | D | 5.401007 | -11.386330 | -6.418972 | -17.46120 | -29.56230 |
| $b_{17}$ | DH | 12.664490 | 13.104690 | 14.640670 | -1.61795 | 0.28894 |
| $b_{18}$ | EH | -4.875359 | 4.092418 | 12.817090 | 5.24342 | 6.82377 |
| $b_{19}$ | ER | 23.275770 | -42.450810 | 0.589681 | 14.51674 | 31.07541 |
| $b_{20}$ | EY | -13.599550 | 4.183425 | 5.650123 | 0.59353 | 35.07248 |
| $b_{21}$ | F | 33.212580 | -3.155725 | 20.493540 | 14.39225 | -11.59104 |
| $b_{22}$ | G | -13.950850 | 18.248470 | 17.078510 | 47.71386 | 69.28384 |
| $b_{23}$ | HH | -13.815710 | 9.044451 | 4.491190 | 8.41946 | -26.94111 |

Figure 15a

|  | phone | 6 months | 12 months | 18 months | 24 months | 36 months |
|---|---|---|---|---|---|---|
| $b_{24}$ | IH | -16.884420 | -28.426910 | -12.831410 | -14.46325 | -63.37338 |
| $b_{25}$ | IY | 48.876380 | -2.084974 | -22.251210 | -15.86588 | -10.63231 |
| $b_{26}$ | JH | 68.057660 | -47.324570 | -97.281480 | -4.68215 | -80.63467 |
| $b_{27}$ | K | 24.542570 | 10.649430 | -47.843910 | -85.82279 | -72.28233 |
| $b_{28}$ | L | 6.979920 | 8.000676 | 10.195310 | 5.11403 | -7.29372 |
| $b_{29}$ | M | 15.951890 | 11.216050 | 6.156351 | 8.92564 | -2.54283 |
| $b_{30}$ | N | -10.670350 | 11.840310 | 17.702970 | 20.36572 | 45.79907 |
| $b_{31}$ | NG | 20.717250 | 10.509790 | 11.006400 | 12.84937 | 9.84875 |
| $b_{32}$ | OW | 4.952251 | -2.036083 | 11.264610 | 3.26010 | -31.87175 |
| $b_{33}$ | OY | -30.818270 | -27.378750 | -2.214016 | 10.99642 | 66.69191 |
| $b_{34}$ | P | 3.185076 | 11.725500 | 23.604480 | 30.85265 | 57.71553 |
| $b_{35}$ | R | 16.118200 | 21.562890 | 9.707237 | 29.13423 | 86.61048 |
| $b_{36}$ | S | -85.662520 | 36.809510 | 13.160290 | -21.70458 | -26.32315 |
| $b_{37}$ | SH | -40.652840 | 9.819386 | 36.425850 | 42.04301 | 54.47242 |
| $b_{38}$ | T | 3.903600 | -6.568943 | 6.785119 | 21.37258 | 20.45459 |
| $b_{39}$ | TH | 65.546130 | 15.803920 | -37.067650 | -19.20251 | 50.91799 |
| $b_{40}$ | UH | -3.498099 | -7.080213 | -6.759240 | -15.69804 | -54.41140 |
| $b_{41}$ | UW | 2.842495 | -5.300199 | -9.814301 | -4.34218 | 10.40091 |
| $b_{42}$ | V | -2.433329 | -7.135176 | -23.293950 | -49.44566 | -32.96628 |
| $b_{43}$ | W | -0.442652 | 11.655380 | 17.664230 | 22.40858 | 33.69935 |
| $b_{44}$ | Y | 22.199500 | 40.728270 | 28.395260 | 37.25442 | 42.47078 |
| $b_{45}$ | Z | 59.402920 | -97.358860 | -58.884430 | 55.01156 | 57.67685 |
| $b_{46}$ | ZH | -82.192380 | 12.481420 | 65.591810 | -16.76468 | -26.99627 |

Figure 15b

| | | A. Rhythm/Syllabicity | Positive classification on group A features suggested speech-like rhythmic organization because values analyzed were islands (roughly, syllables) per utterance (SVIs per SCU) showing group A features. Thus, utterances were rhythmically organized in accord with speech if they tended to show relatively high numbers of syllables per utterance with voicing, canonical formant transitions, and spectral entropy variations typical of speech. |
|---|---|---|---|
| 1 | VC | Voiced or unvoiced: pitch detectable through >50% of island (roughly, syllable) | |
| 2 | CS | Canonical Syllable transitions or not: Formant transitions < 120ms | |
| 3 | SE | Spectral Entropy typical of speech or not | |
| | | B. Low spectral tilt and high pitch control | Positive classification on group B parameters suggested control of high pitch and low spectral tilt, which tend to occur in certain typical emotional expressions of high intensity (squeal quality). More islands per utterance with B parameters suggested more active emotional expression in the high spectral frequency range. |
| 4 | SQ | Mean pitch high or not (Squeal): > 600 Hz | |
| 5 | LT | Low Tilt of spectrum or not | |
| 6 | HF | High Frequency energy concentration or not | |
| | | C. Wide formant bandwidth and low pitch control | Positive classification on group C parameters suggested control of low pitch and high bandwidths of the first two formants, qualities which tend to occur in certain typical emotional expressions of high intensity (growl quality). More islands per utterance with C parameters suggested more active emotional expression in the low spectral frequency range. |
| 7 | GW | Mean pitch low or not (Growl): <250 Hz | |
| 8 | WB | Wide bandwidth of first two formants or not | |
| | | D. Duration of islands within utterances (SCUs) | Group D parameters split according to duration typical of syllables in speech. Positive classification on parameters 9 and 10 suggested speech-like rhythmic organization because the durational values indicated are typical of syllables in speech. More islands per utterance with 9 and 10 thus suggested more speech-like syllables. Positive classification on parameters 11 and 12 suggested the opposite, because the corresponding ranges are beyond the durations of typical syllables. |
| 9 | S | Short (110 - 250 ms) | |
| 10 | M | Medium (250 - 600 ms) | |
| 11 | L | Long (600 - 900 ms) | |
| 12 | XL | EXtra Long (900 - 3000 ms) | |

Figure 21

| | |
|---|---|
| AUL | adult vocalization length in sec |
| AUC | adult vocalization count |
| CIC | child initiated conversations |
| TT | conversational turns |
| TT-CIC | conversational turns in child initiated conversations |
| CVL-TT | child vocalization length in sec in conversational turns |
| CVC-TT | child vocalization counts in conversational turns |
| CVL-GC | child vocalization length in conversations with adult |
| CVC-GC | child vocalization counts in conversations with adult |

Figure 22

LR with CSATP at EER - LOOCV

N: Normative [328]
D: Delayed [30]
A: Autistic set [34]
$P_t$ = Prob. at EER

Machine $P_t$ = .42

| Truth | Machine A | Machine D |
|---|---|---|
| A | 65% [22] | 35% [12] |
| D | 39% [11] | 62% [19] |

Machine $P_t$ = .98

| Truth | Machine N | Machine A |
|---|---|---|
| N | 93% [304] | 7% [24] |
| A | 12% [4] | 88% [30] |

Machine $P_t$ = .96

| Truth | Machine N | Machine D |
|---|---|---|
| N | 78% [256] | 22% [72] |
| D | 19% [5] | 81% [25] |

LDA with CSATP at EER - LOOCV

Machine $P_t$ = .50

| Truth | Machine A | Machine D |
|---|---|---|
| A | 68% [23] | 32% [11] |
| D | 32% [10] | 68% [20] |

Machine $P_t$ = .88

| Truth | Machine N | Machine A |
|---|---|---|
| N | 91% [299] | 9% [29] |
| A | 9% [3] | 91% [31] |

Machine $P_t$ = .64

| Truth | Machine N | Machine D |
|---|---|---|
| N | 83% [272] | 17% [58] |
| D | 16% [4] | 84% [26] |

All Acoustic Parameters are used for modeling LDA and LR, LOOCV testing
EER: Equal Error Rate

SYSTEM AND METHOD FOR EMOTION ASSESSMENT

CROSS-REFERENCE TO RELATED APPLICATIONS

This application is a divisional of U.S. patent application Ser. No. 12/359,124, filed Jan. 23, 2009, which is a continuation in part of U.S. patent application Ser. No. 12/109,785, filed on Apr. 25, 2008, which is a continuation-in-part of U.S. patent application Ser. No. 12/018,647, filed Jan. 23, 2008, which claims the benefit of U.S. Provisional Application No. 60/886,122, filed Jan. 23, 2007, and U.S. Provisional Application No. 60/886,167, filed Jan. 23, 2007.

This application also is related to U.S. patent application Ser. No. 11/162,520, filed Sep. 13, 2005 (the "'520 application"), which claims the benefit of U.S. Provisional Application No. 60/522,340, filed Sep. 16, 2004.

U.S. patent application Ser. Nos. 12/359,124, 12/109,785, 12/018,647, and 11/162,520, and U.S. Provisional Application Nos. 60/886,122, 60/886,167, and 60/522,340 are incorporated herein by reference in their entirety.

TECHNICAL FIELD

The present invention relates generally to automated language assessment and, specifically, to assessing a key child's expressive language development by analyzing phones used by the child, to analyzing recordings to assist in the detection of diseases and disorders such as Autism, and to detecting emotion.

BACKGROUND

As discussed in more detail in the '520 application, the language environment surrounding a young child is key to the child's development. A child's language and vocabulary ability at age three, for example, can indicate intelligence and test scores in academic subjects such as reading and math at later ages. Improving language ability typically results in a higher intelligent quotient (IQ) as well as improved literacy and academic skills.

Exposure to a rich aural or listening language environment in which many words are spoken with a large number of interactive conversational turns between the child and adult and a relatively high number of affirmations versus prohibitions may promote an increase in the child's language ability and IQ. The effect of a language environment surrounding a child of a young age on the child's language ability and IQ may be particularly pronounced.

In the first four years of human life, a child experiences a highly intensive period of speech and language development due in part to the development and maturing of the child's brain. Even after children begin attending school or reading, much of the child's language ability and vocabulary, including the words known (receptive vocabulary) and the words the child uses in speech (expressive vocabulary), are developed from conversations the child experiences with other people.

In addition to hearing others speak to them and responding (i.e., conversational turns), a child's language development may be promoted by the child's own speech. The child's own speech is a dynamic indicator of cognitive functioning, particularly in the early years of a child's life. Research techniques have been developed which involve counting a young child's vocalizations and utterances to estimate a child's cognitive development. Current processes of collecting information may include obtaining data via a human observer and/or a transcription of an audio recording of the child's speech. The data is analyzed to provide metrics with which the child's language environment can be analyzed and potentially modified to promote increasing the child's language development and IQ.

The presence of a human observer, however, may be intrusive, influential on the child's performance, costly, and unable to adequately obtain information on a child's natural environment and development. Furthermore, the use of audio recordings and transcriptions is a costly and time-consuming process of obtaining data associated with a child's language environment. The analysis of such data to identify canonical babbling, count the number of words, determine mean length of utterances and other vocalization metrics, and determine content spoken is also time intensive.

Counting the number of words and determining content spoken may be particularly time and resource intensive, even for electronic analysis systems, since each word is identified along with its meaning. Accordingly, a need exists for methods and systems for obtaining and analyzing data associated with a child's language environment independent of content and reporting metrics based on the data in a timely manner. The analysis should also include an automatic assessment of the child's expressive language development.

Beyond an automatic assessment of a child's expressive language development, a need exists for the development of specific metrics and methodologies for determining specific developmental disorders in a child. As expressed above, a test that is largely non-invasive, in terms of providing a human observer, and that is of low cost while at the same time generating a substantial amount of data is desirable. One such developmental disorder of interest that can be detected through the analysis of speech is autism. Another factor contributing to language development may be emotion. When children are exposed to an emotionally stressed environment there learning and language development may suffer. Therefore, a system and method for detecting the emotional content of subject interactions may be desirable for assisting in language development.

SUMMARY

Certain embodiments of the system and method for expressive language development provide methods and systems for providing metrics associated with a key child's language environment and development in a relatively quick and cost effective manner. The metrics may be used to promote improvement of the language environment, key child's language development, and/or to track development of the child's language skills. In one embodiment of the present invention, a method is provided for generating metrics associated with the key child's language environment. An audio recording from the language environment can be captured. The audio recordings may be segmented into a plurality of segments. A segment ID can be identified for each of the plurality of segments. The segment ID may identify a source for audio in the segment of the recording. Key child segments can be identified from the segments. Each of the key child segments may have the key child as the segment ID. Key child segment characteristics can be estimated based in part on at least one of the key child segments. The key child segment characteristics can be estimated independent of content of the key child segments. At least one metric associated with the language environment and/or language development may be determined using the key child segment characteristics. Examples of metrics include the number of words or vocalizations spoken by the key child in a pre-set time period and the number of conversational turns. The at least one metric can be output to an output device.

In some embodiments, adult segments can be identified from the segments. Each of the adult segments may have the adult as the segment ID. Adult segment characteristics can be estimated based in part on at least one of the adult segments. The adult segment characteristics can be estimated independent of content of the adult segments. At least one metric associated with the language environment may be determined using the adult segment characteristics.

In one embodiment of the system and method for expressive language development, a system for providing metrics associated with a key child's language environment is provided. The system may include a recorder and a processor-based device. The recorder may be adapted to capture audio recordings from the language environment and provide the audio recordings to a processor-based device. The processor-based device may include an application having an audio engine adapted to segment the audio recording into segments and identify a segment ID for each of the segments. At least one of the segments may be associated with a key child segment ID. The audio engine may be further adapted to estimate key child segment characteristics based in part on the at least one of the segments, determine at least one metric associated with the language environment or language development using the key child segment characteristics, and output the at least one metric to an output device. The audio engine may estimate the key child segment characteristics independent of content of the segments.

In one embodiment of the system and method for expressive language development, the key child's vocalizations are analyzed to identify the number of occurrences of certain phones and to calculate a frequency distribution or a duration distribution for the phones. The analysis may be performed independent of the content of the vocalizations. A phone decoder designed for use with an automatic speech recognition system used to identify content from adult speech can be used to identify the phones. The key child's chronological age is used to select an age-based model which uses the distribution of the phones, as well as age-based weights associated with each phone, to assess the key child's expressive language development. The assessment can result in a standard score, an estimated developmental age, or an estimated mean length of utterance measure.

In one embodiment, a method of assessing a key child's expressive language development includes processing an audio recording taken in the key child's language environment to identify segments of the recording that correspond to the key child's vocalizations. The method further includes applying an adult automatic speech recognition phone decoder to the segments to identify each occurrence of each of a plurality of bi-phone categories. Each of the bi-phone categories corresponds to a pre-defined speech sound sequence. The method also includes determining a distribution for the bi-phone categories and using the distribution in an age-based model to assess the key child's expressive language development.

In another embodiment, a system for assessing a key child's language development includes a processor-based device comprising an application having an audio engine for processing an audio recording taken in the key child's language environment to identify segments of the recording that correspond to the key child's vocalizations. The system also includes an adult automatic speech recognition phone decoder for processing the segments that correspond to the key child's vocalizations to identify each occurrence of each of a plurality of bi-phone categories. Each of the bi-phone categories corresponds to a pre-defined speech sound sequence. The system further includes an expressive language assessment component for determining a distribution for the bi-phone categories and using the distributions in an age-based model to assess the key child's expressive language development. The age-based model is selected based on the key child's chronological age, and the age-based model includes a weight associated with each of the bi-phone categories.

In one embodiment of the system and method for expressive language development, a method for detecting autism in a natural language environment includes using a microphone, sound recorder, and a computer programmed with software for the specialized purpose of processing recordings captured by the microphone and sound recorder combination. The computer is programmed to execute a method that includes segmenting an audio signal captured by the microphone and sound recorder combination using the computer programmed for the specialized purpose into a plurality of recording segments. The method further includes determining which of the plurality of recording segments correspond to a key child. The method also includes extracting acoustic parameters of the key child recordings and comparing the acoustic parameters of the key child recordings to known acoustic parameters for children. The method returns a determination of a likelihood of autism.

In another embodiment, a method for detecting autism includes transforming an audio recording to display an indication of autism on an output mechanism selected from the group consisting of a display, a printout, and an audio output, the transforming of the audio recording performed by comparing it to a model developed by analyzing the transparent parameters of a plurality of sound recordings captured in a natural language environment.

Additionally, another embodiment includes a method for detecting a disorder in a natural language environment using a microphone, sound recorder, and a computer programmed with software for the specialized purpose of processing recordings captured by the microphone and sound recorder combination. The computer is programmed to execute a method. The method includes segmenting an audio signal captured by the microphone and sound recorder combination using the computer programmed for the specialized purpose into a plurality of recording segments; determining which of the plurality of recording segments correspond to a key subject; determining which of the plurality of recording segments that correspond to the key subject are classified as key subject recordings; extracting acoustic parameters of the key subject recordings; comparing the acoustic parameters of the key subject recordings to known acoustic parameters for subjects; and determining a likelihood of the disorder.

In yet another embodiment, a method for detecting a disorder includes transforming an audio recording to display an indication of autism on an output mechanism selected from the group consisting of a display, a printout, and an audio output, the transforming of the audio recording performed by comparing it to a model developed by analyzing the transparent parameters of a plurality of sound recordings captured in a natural language environment. In the case of each of the plurality of sound recordings, the analyzing includes segmenting the sound recording into a plurality of recording segments, wherein the sound recording is captured by a microphone and sound recorder combination; determining which of the plurality of recording segments correspond to a key subject; determining which of the plurality of recording segments that correspond to the key subject are classified as key subject recordings; and extracting acoustic parameters of the key subject recordings.

In one embodiment, a method of creating an automatic language characteristic recognition system includes receiving a plurality of audio recordings. The audio recordings are segmented to create a plurality of audio segments for each audio recording. The plurality of audio segments is clustered according to audio characteristics of each audio segment to form a plurality of audio segment clusters.

In one embodiment, a method of decoding speech using an automatic language characteristic recognition system includes receiving a plurality of audio recordings and segmenting each of the plurality of audio recordings to create a first plurality of audio segments for each audio recording. The method further includes clustering each audio segment of the plurality of audio recordings according to audio characteristics of each audio segment to form a plurality of audio segment clusters. The method additionally includes receiving a new audio recording, segmenting the new audio recording to create a second plurality of audio segments for the new audio recording, and determining to which cluster of the plurality of audio segment clusters each segment of the second plurality of audio segments corresponds.

In one embodiment, a method of determining the emotion of an utterance includes receiving the utterance at a processor-based device comprising an application having an audio engine. The method further includes extracting emotion-related acoustic features from the utterance. The method additionally includes comparing the emotion-related acoustic features to a plurality of models representative of emotions. Further included is selecting a model from the plurality of models based on the comparing and outputting the emotion corresponding to the selected model.

In some embodiments, a method of determining an emotion of an utterance. The method can include receiving the utterance at a processor-based device comprising an audio engine. The method also can include extracting emotion-related acoustic features from the utterance. The method additionally can include comparing the emotion-related acoustic features to a plurality of emotion models that are representative of emotions. The method further can include selecting a model from the plurality of emotion models based on the comparing the emotion-related acoustic features to the plurality of emotion models. The method additionally can include outputting the emotion of the utterance, wherein the emotion corresponds to the selected model.

These embodiments are mentioned not to limit or define the invention, but to provide examples of embodiments of the invention to aid understanding thereof. Embodiments are discussed in the Detailed Description and advantages offered by various embodiments of the present invention may be further understood by examining the Detailed Description and Drawings.

BRIEF DESCRIPTION OF THE DRAWINGS

These and other features, aspects, and advantages of the present invention are better understood when the following Detailed Description is read with reference to the accompanying drawings, wherein:

FIG. 13 illustrates the correlation between chronological age and certain phones;

FIG. 14 illustrates the non-linear relationship between some of the phones of FIG. 13 and chronological age;

FIGS. 15*a* and 15*b*, collectively referred to herein as FIG. 15, is a table illustrating the weights used for the expressive language index z-score according to one embodiment of the present invention;

FIG. 21 shows 12 acoustic parameters of vocal development;

FIG. 22 shows an example of non-acoustic parameters;

FIG. 31 shows tables showing the accuracy of a machine employing one embodiment of the system and methods of detecting autism;

DESCRIPTION OF EXAMPLES OF EMBODIMENTS

Figure 1:
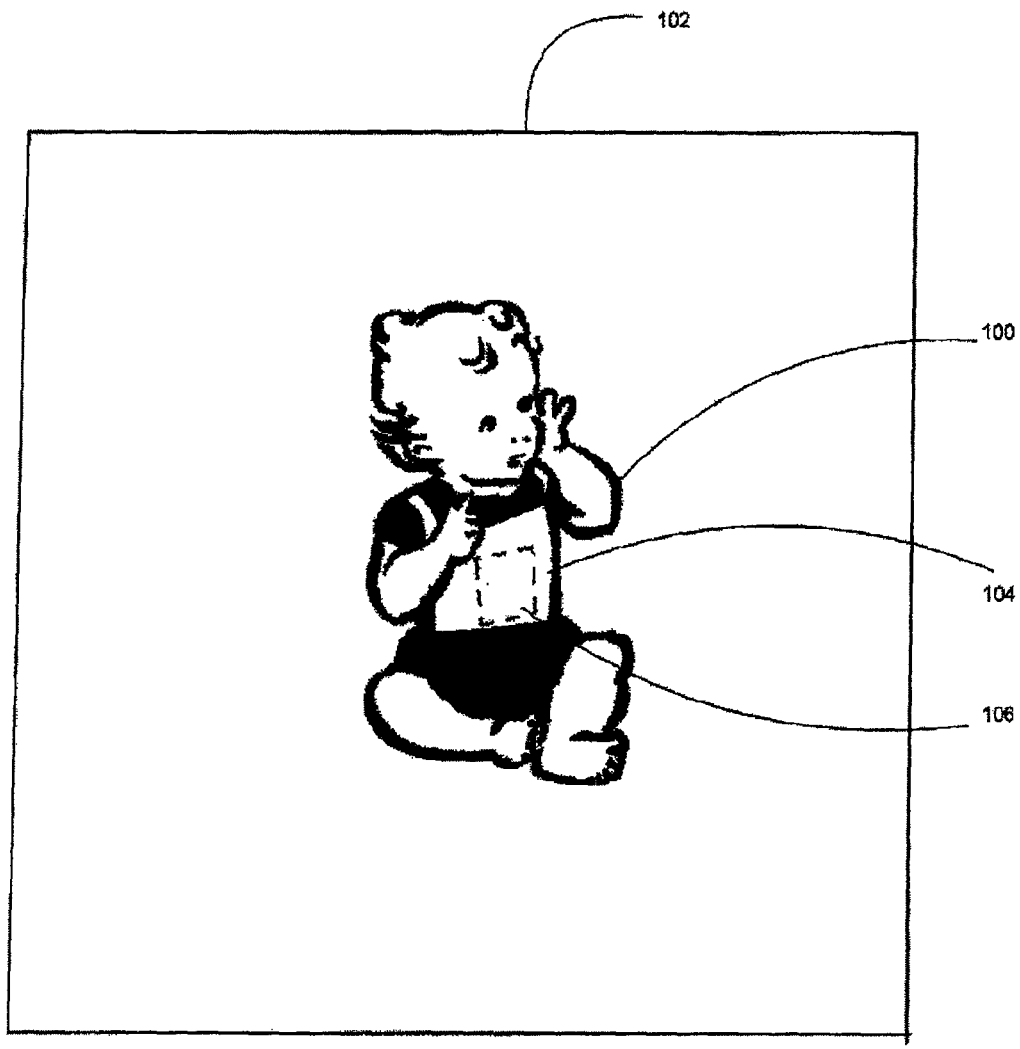
FIG. 1 illustrates a key child's language environment according to one embodiment of the present invention.

Certain aspects and embodiments of the present invention are directed to systems and methods for monitoring and analyzing the language environment, vocalizations, and the development of a key child. A key child as used herein may be a child, an adult, such as an adult with developmental disabilities, or any individual whose language development is of interest. A key child's language environment and language development can be monitored without placing artificial limitations on the key child's activities or requiring a third-party observer. The language environment can be analyzed to identify words or other noises directed to or vocalized by the key child independent of content. Content may include the meaning of vocalizations such as words and utterances. The analysis can include the number of responses between the child and another, such as an adult (referred to herein as "conversational turns"), and the number of words spoken by the child and/or another, independent of content of the speech.

A language environment can include a natural language environment or other environments such as a clinical or research environment. A natural language environment can include an area surrounding a key child during his or her normal daily activities and contain sources of sounds that may include the key child, other children, an adult, an electronic device, and background noise. A clinical or research environment can include a controlled environment or location that contains pre-selected or natural sources of sounds.

In some embodiments of the present invention, the key child may wear an article of clothing that includes a recording device located in a pocket attached to or integrated with the article of clothing. The recording device may be configured to record and store audio associated with the child's language environment for a predetermined amount of time. The audio recordings can include noise, silence, the key child's spoken words or other sounds, words spoken by others, sounds from electronic devices such as televisions and radios, or any sound or words from any source. The location of the recording device preferably allows it to record the key child's words and noises and conversational turns involving the key child without interfering in the key child's normal activities. During or after the pre-set amount of time, the audio recordings stored on the recording device can be analyzed independent of content to provide characteristics associated with the key child's language environment or language development. For example, the recordings may be analyzed to identify segments and assign a segment ID or a source for each audio segment using a Minimum Duration Gaussian Mixture Model (MD-GMM).

Sources for each audio segment can include the key child, an adult, another child, an electronic device, or any person or object capable of producing sounds. Sources may also include general sources that are not associated with a particular person or device. Examples of such general sources include noise, silence, and overlapping sounds. In some embodiments, sources are identified by analyzing each audio segment using models of different types of sources. The models may include audio characteristics commonly associated with each source. In some embodiments, to detect the source type of audio signal, silence is detected. Any non-silent segment may still contain some short silence period, such as the pause involved in the explosive consonants like "p" and "t". Such a short low energy region may not contain the information about the signal source type; thus, it will be removed from the likelihood calculation of a non-silence-segment. Audio segments for which the key child or an adult is identified as the source may be further analyzed, such as by determining certain characteristics associated with the key child and/or adult, to provide metrics associated with the key child's language environment or language development.

In some embodiments of the present invention, the key child is a child between the ages of zero and four years old. Sounds generated by young children differ from adult speech in a number of respects. For example, the child may generate a meaningful sound that does not equate to a word; the formant transitions from a consonant to a vowel or visa-versa for child speech are less pronounced than the transitions for adult speech, and the child's speech changes over the age range of interest due to physical changes in the child's vocal tract. Differences between child and adult speech may be recognized and used to analyze child speech and to distinguish child speech from adult speech, such as in identifying the source for certain audio segments.

Certain embodiments of the present invention use a system that analyzes speech independent of content rather than a system that uses speech recognition to determine content. These embodiments greatly reduce the processing time of an audio file and require a system that is significantly less expensive than if a full speech recognition system were used. In some embodiments, speech recognition processing may be used to generate metrics of the key child's language environment and language development by analyzing vocalizations independent of content. In one embodiment, the recommended recording time is twelve hours with a minimum time of ten hours. In order to process the recorded speech and to provide meaningful feedback on a timely basis, certain embodiments of the present invention are adapted to process a recording at or under half of real time. For example, the twelve-hour recording may be processed in less than six hours. Thus, the recordings may be processed overnight so that results are available the next morning. Other periods of recording time may be sufficient for generating metrics associated with the key child's language environment and/or language development depending upon the metrics of interest and/or the language environment. A one- to two-hour recording time may be sufficient in some circumstances such as in a clinical or research environment. Processing for such recording times may be less than one hour.

Audio Acquisition

As stated above, a recording device may be used to capture, record, and store audio associated with the key child's language environment and language development. The recording device may be any type of device adapted to capture and store audio and to be located in or around a child's language environment. In some embodiments, the recording device includes one or more microphones connected to a storage device and located in one or more rooms that the key child often occupies. In other embodiments, the recording device is located in an article of clothing worn by the child.

FIG. 1 illustrates a key child, such as child 100, in a language environment 102 wearing an article of clothing 104 that includes a pocket 106. The pocket 106 may include a recording device (not shown) that is adapted to record audio from the language environment 102. The language environment 102 may be an area surrounding the child 100 that includes sources for audio (not shown), including one or more adults, other children, and/or electronic devices such as a television, a radio, a toy, background noise, or any other source that produces sounds. Examples of language environment 102 include a natural language environment and a clinical or research language environment. The article of clothing 104 may be a vest over the child's 100 normal clothing, the child's 100 normal clothing, or any article of clothing commonly worn by the key child.

In some embodiments, the recorder is placed at or near the center of the key child's chest. However, other placements are possible. The recording device in pocket 106 may be any device capable of recording audio associated with the child's language environment.

Figure 2A:
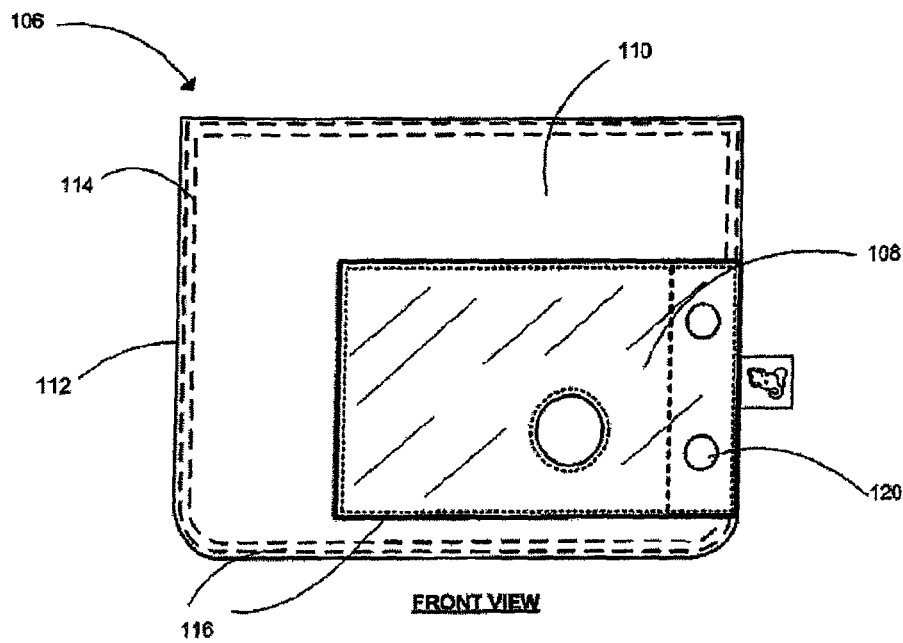
FIG. 2*a* is a front view of a recorder in a pocket according to one embodiment of the present invention.
Figure 2B:
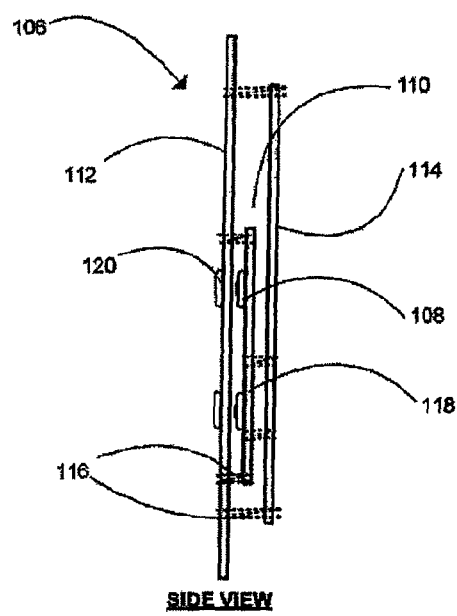
FIG. 2*b* is a side view of the recorder and pocket of FIG. 2*a*.

One example of a recording device is a digital recorder of the LENA system. The digital recorder may be relatively small and lightweight and can be placed in pocket 106. The pocket 106 can hold the recorder in place in an unobtrusive manner so that the recorder does not distract the key child, other children, and adults that interact with the key child. FIGS. 2a and 2b illustrate one embodiment of a pocket 106 including a recorder 108. The pocket 106 may be designed to keep the recorder 108 in place and to minimize acoustic interference. The pocket 106 can include an inner area 110 formed by a main body 112 and an overlay 114 connected to the main body 112 via stitches 116 or another connecting mechanism. The main body 112 can be part of the clothing or attached to the article of clothing 104 using stitches or otherwise. A stretch layer 118 may be located in the inner area 110 and attached to the main body 112 and overlay 114 via stitches 116 or other connecting mechanism. The recorder 108 can be located between the main body 112 and the stretch layer 118. The stretch layer 118 may be made of a fabric adapted to stretch but provide a force against the recorder 108 to retain the recorder 108 in its position. For example, the stretch layer may be made from a blend of nylon and spandex, such as 85% nylon, 15% spandex, which helps to keep the recorder in place. The overlay 114 may cover the stretch layer 118 and may include at least one opening where the microphone of recorder 108 is located. The opening can be covered with a material that provides certain desired acoustic properties. In one embodiment, the material is 100% cotton.

The pocket 106 may also include snap connectors 120 by which the overlay 114 is opened and closed to install or remove the recorder 108. In some embodiments, at least one of the stitches 116 can be replaced with a zipper to provide access to the recorder 108 in addition or alternative to using snap connectors 120.

If the recorder 108 includes multiple microphones, then the pocket 106 may include multiple openings that correspond to the placement of the microphones on the recorder 108. The particular dimensions of the pocket 106 may change as the design of the recorder 108 changes or as the number or type of microphones change. In some embodiments, the pocket 106 positions the microphone relative to the key child's mouth to provide certain acoustical properties and secure the microphone (and optionally the recorder 108) in a manner that does not result in friction noises. The recorder 108 can be turned on and thereafter record audio, including speech by the key child, other children, and adults, as well as other types of sounds that the child encounters, including television, toys, environmental noises, etc. The audio may be stored in the recorder 108. In some embodiments, the recorder can be periodically removed from pocket 106 and the stored audio can be analyzed.

Illustrative Audio Recording Analysis System Implementation

Figure 3:
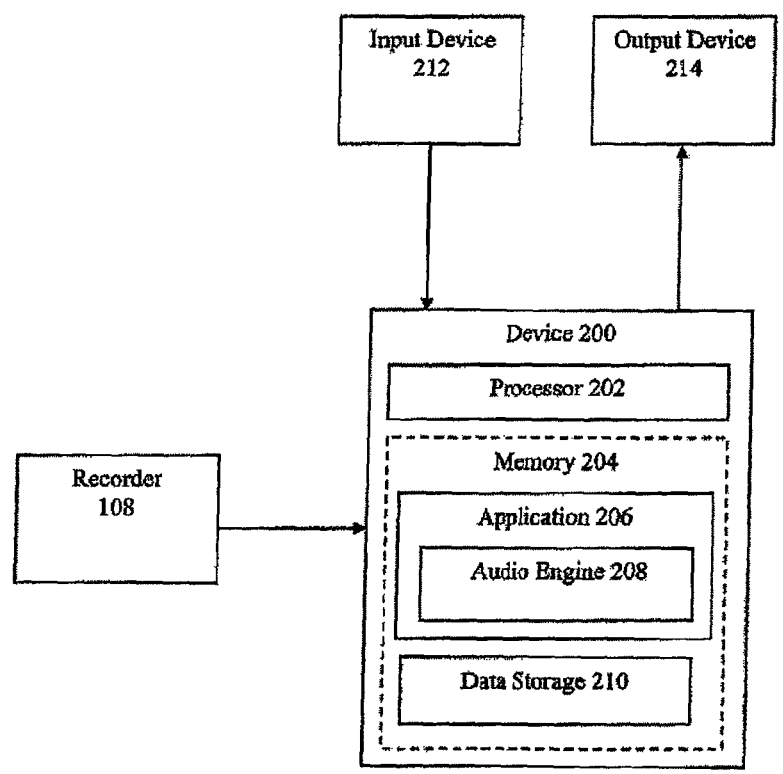
FIG. 3 is a recording processing system according to one embodiment of the present invention.

Methods for analyzing audio recordings from a recorder according to various embodiments of the present invention may be implemented on a variety of different systems. An example of one such system is illustrated in FIG. 3. The system includes the recorder 108 connected to a processor-based device 200 that includes a processor 202 and a computer-readable medium, such as memory 204. The recorder 108 may be connected to the processor-based device 200 via wireline or wirelessly. In some embodiments, the recorder 108 is connected to the device 200 via a USB cable. The device 200 may be any type of processor-based device, examples of which include a computer and a server. Memory 204 may be adapted to store computer-executable code and data. Computer-executable code may include an application 206, such as a data analysis application that can be used to view, generate, and output data analysis. The application 206 may include an audio engine 208 that, as described in more detail below, may be adapted to perform methods according to various embodiments of the present invention to analyze audio recordings and generate metrics associated therewith. In some embodiments, the audio engine 208 may be a separate application that is executable separate from, and optionally concurrent with, application 206. Memory 204 may also include a data storage 210 that is adapted to store data generated by the application 206 or audio engine 208, or input by a user. In some embodiments, data storage 210 may be separate from device 200 but connected to the device 200 via wireline or wireless connection.

The device 200 may be in communication with an input device 212 and an output device 214. The input device 212 may be adapted to receive user input and communicate the user input to the device 200. Examples of input device 212 include a keyboard, mouse, scanner, and network connection. User inputs can include commands that cause the processor 202 to execute various functions associated with the application 206 or the audio engine 208. The output device 214 may be adapted to provide data or visual output from the application 206 or the audio engine 208. In some embodiments, the output device 214 can display a graphical user interface (GUI) that includes one or more selectable buttons that are associated with various functions provided by the application 206 or the audio engine 208. Examples of output device 214 include a monitor, network connection, and printer. The input device 212 may be used to setup or otherwise configure audio engine 208. For example, the age of the key child and other information associated with the key child's learning environment may be provided to the audio engine 208 and stored in local storage 210 during a setup or configuration.

The audio file stored on the recorder 108 may be uploaded to the device 200 and stored in local storage 210. In one embodiment, the audio file is uploaded in a proprietary format which prevents the playback of the speech from the device 200 or access to content of the speech, thereby promoting identity protection of the speakers. In other embodiments, the audio file is uploaded without being encoded to allow for storage in local storage 210 and playback of the file or portions of the file.

In some embodiments, the processor-based device 200 is a web server, and the input device 212 and output device 214 are combined to form a computer system that sends data to and receives data from the device 200 via a network connection. The input device 212 and output device 214 may be used to access the application 206 and audio engine 208 remotely and cause it to perform various functions according to various embodiments of the present invention. The recorder 108 may be connected to the input device 212 and output device 214, and the audio files stored on the recorder 108 may be uploaded to the device 200 over a network such as an internet or intranet where the audio files are processed and metrics are provided to the output device 214. In some embodiments, the audio files received from a remote input device 212 and output device 214 may be stored in local storage 210 and subsequently accessed for research purposes such as on a child's learning environment or otherwise.

To reduce the amount of memory needed on the recorder 108, the audio file may be compressed. In one embodiment, a DVI-4 ADPCM compression scheme is used. If a compression scheme is used, then the file is decompressed after it is uploaded to the device 200 to a normal linear PCM audio format.

Illustrative Methods for Audio Recording Analysis

Figure 4:
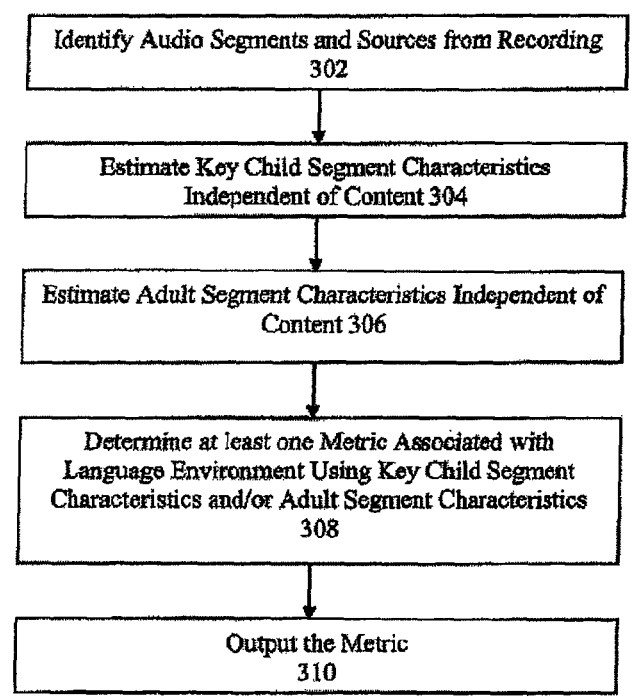
FIG. 4 is flow chart of a method for processing recordings according to one embodiment of the present invention.

Various methods according to various embodiments of the present invention can be used to analyze audio recordings. FIG. 4 illustrates one embodiment of a method for analyzing and providing metrics based on the audio recordings from a key child's language environment. For purposes of illustration only, the elements of this method are described with reference to the system depicted in FIG. 3. Other system implementations of the method are possible.

In block 302, the audio engine 208 divides the recording into one or more audio segments and identifies a segment ID or source for each of the audio segments from the recording received from the recorder 108. This process is referred to herein as "segmentation" and "segment ID". An audio segment may be a portion of the recording having a certain duration and including acoustic features associated with the child's language environment during the duration. The recording may include a number of audio segments, each associated with a segment ID or source. Sources may be an individual or device that produces the sounds within the audio segment. For example, an audio segment may include the sounds produced by the key child, who is identified as the source for that audio segment. Sources also can include other children, adults, electronic devices, noise, overlapped sounds, and silence. Electronic devices may include televisions, radios, telephones, toys, and any device that provides recorded or simulated sounds such as human speech.

Sources associated with each of the audio segments may be identified to assist in further classifying and analyzing the recording. Some metrics provided by some embodiments of the present invention include data regarding certain sources and disregard data from other sources. For example, audio segments associated with live speech directed to the key child can be distinguished from audio segments associated with electronic devices, since live speech has been shown to be a better indicator and better promoter of a child's language development than exposure to speech from electronic devices.

To perform segmentation to generate the audio segments and identify the sources for each segment, a number of models may be used that correspond to the key child, other children, male adult, female adult, noise, TV noise, silence, and overlap. Alternative embodiments may use more, fewer, or different models to perform segmentation and identify a corresponding segment ID. One such technique performs segmentation and segment ID separately. Another technique performs segmentation and identifies a segment ID for each segment concurrently.

Traditionally, a Hidden Markov Model (HMM) with minimum duration constraint has been used to perform segmentation and identify segment IDs concurrently. A number of HMM models may be provided, each corresponding to one source. The result of the model may be a sequence of sources with a likelihood score associated with each source. The optimal sequence may be searched using a Viterbi algorithm or dynamic programming and the "best" source identified for each segment based on the score. However, this approach may be complex for some segments in part because it uses transition probabilities from one segment to another—i.e., the transition between each segment. Transition probabilities are related to duration modeling of each source. MINI duration models may have discrete geometric distribution or continuous exponential distribution, which may not be appropriate for the sound sources of concern. Most recordings may include segments of having a high degree of variation in their duration. Although the HMM model may be used in some embodiments of the present invention, alternative techniques may be used to perform segmentation and segment ID.

An alternative technique used in some embodiments of the present invention to perform segmentation and segment ID is a Minimum Duration Gaussian Mixture Model (MD-GMM). Each model of the MD-GMM may include criteria or characteristics associated with sounds from different sources. Examples of models of the MD-GMM include a key child model that includes characteristics of sounds from a key child, an adult model that includes characteristics of sounds from an adult, an electronic device model that includes characteristics of sounds from an electronic device, a noise model that includes characteristics of sounds attributable to noise, another child model that includes characteristics of sounds from a child other than the key child, a parentese model that includes complexity level speech criteria of adult sounds, an age-dependent key child model that includes characteristics of sounds of a key child of different ages, and a loudness/clearness detection model that includes characteristics of sounds directed to a key child. Some models include additional models. For example, the adult model may include an adult male model that includes characteristics of sounds of an adult male and an adult female model that includes characteristics of sounds of an adult female. The models may be used to determine the source of sound in each segment by comparing the sound in each segment to criteria of each model and determining if a match of a pre-set accuracy exists for one or more of the models.

In some embodiments of the present invention, the MD-GMM technique begins when a recording is converted to a sequence of frames or segments. Segments having a duration of 2*D, where D is a minimum duration constraint, are identified using a maximum log-likelihood algorithm for each type of source. The maximum score for each segment is identified. The source associated with the maximum score is correlated to the segment for each identified segment.

The audio engine 208 may process recordings using the maximum likelihood MD-GMM to perform segmentation and segment ID. The audio engine 208 may search all possible segment sequences under a minimum duration constraint to identify the segment sequence with maximum likelihood. One possible advantage of MD-GMM is that any segment longer than twice the minimum duration (2*D) could be equivalently broken down into several segments with a duration between the minimum duration (D) and two times the minimum duration (2*D), such that the maximum likelihood search process ignores all segments longer than 2*D. This can reduce the search space and processing time. The following is an explanation of one implementation of using maximum likelihood MD-GMM. Other implementations are also possible:

1. Acoustic Feature Extraction—the audio stream is converted to a stream of feature vectors $\{X_1, X_2 \ldots X_T | X_i \in R^n\}$ using a feature extraction algorithm, such as the MFCC (mel-frequency cepstrum coefficients).
2. Log likelihood calculation for a segment $\{X_1, X_2 \ldots X_S\}$:

$$Lcs = \sum_{i=1}^{S} \log(f_c(X_i)),$$

where $f_c(X_i)$ is the likelihood of frame $X_i$ being in class c.

The following describes one procedure of maximum likelihood MD-GMM search:

3. Initialize searching variables: $S(c,0,0)=0$, $c=1, \ldots, C$, where c is the index for all segment classes. Generally, the searching variable $S(c,b,n)$ represents the maximum log-likelihood for the segment sequence up to the frame $b-1$ plus the log-likelihood of the segment from frame b to frame n being in class c.
4. Score frames for $n=1, \ldots, T$, i.e. all feature frames:

$$S(c,b,n)=S(c,b,n-1)+\log(f_c(X_n)), \forall b,c,n-b<2*D_c,$$

i.e., the current score at frame n could be derived from the previous score at frame n−1. The searching variable for segments less than twice the minimum duration is retained.

5. Retain a record of the optimal result at frame n (similarly, segments under twice the minimum duration will be considered):

$$S^*(n) = \max_{c,b,2*Dc>9n-b)>Dc} S(c, b, n)$$

$$B^*(n) = \arg\max_{b,(c,b,2*Dc>(n-b)>Dc} S(c, b, n)$$

$$C^*(n) = \arg\max_{c,(c,b,2*Dc>(n-b)>Dc} S(c, b, n)$$

6. Initialize new searching variables for segments starting at frame n:

$$S(c,n,n)=S^*(n), \forall c$$

7. Iterate step 4 to step 6 until the last frame T.
8. Trace back to get the maximum likelihood segment sequence.

The very last segment of the maximum likelihood segment sequence is $(C^*(T),B^*(T),T)$, i.e., the segment starting from frame $B^*(T)$ and ending with frame T with class id of $C^*(T)$. We can obtain the rest segments in the best sequence by using the following back-tracing procedure:

8.1. Initialize back-tracing:

$$t=T, m=1$$

$$S(m)=(C^*(t),B^*(t),t)$$

8.2. Iterate back-tracing until t=0

$$C\_current=C^*(t)$$

$$t=B^*(t)$$

If $C^*(t)=C\_current$, then do nothing;
Otherwise, $m=m+1$, $S(m)=(C^*(t),B^*(t),t)$ Additional processing may be performed to further refine identification of segments associated with the key child or an adult as sources. As stated above, the language environment can include a variety of sources that may be identified initially as the key child or an adult when the source is actually a different person or device. For example, sounds from a child other than the key child may be initially identified as sounds from the key child. Sounds from an electronic device may be confused with live speech from an adult. Furthermore, some adult sounds may be detected that are directed to another person other than the key child. Certain embodiments of the present invention may implement methods for further processing and refining the segmentation and segment ID to decrease or eliminate inaccurate source identifications and to identify adult speech directed to the key child.

Figure 5:
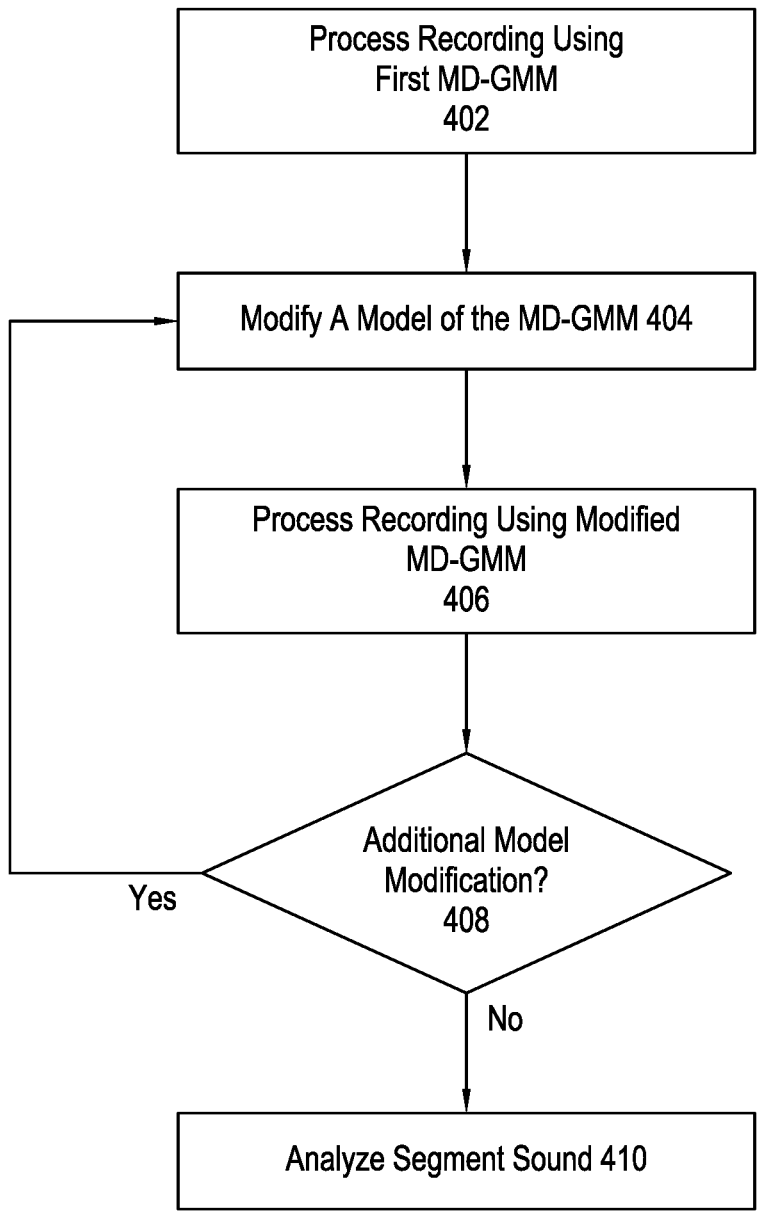
FIG. 5 is a flow chart of a method for performing further recording processing according to one embodiment of the present invention.

Further processing may occur concurrently with, or subsequent to, the initial MD-GMM model described above. FIG. 5 illustrates one embodiment of an adaptation method for further processing the recording by modifying models associated with the MD-GMM subsequent to an initial MD-GMM. In block 402, the audio engine 208 processes the recording using a first MD-GMM. For example, the recording is processed in accordance with the MD-GMM described above to perform an initial segmentation and segment ID.

In block 404, the audio engine 208 modifies at least one model of the MD-GMM. The audio engine 208 may automatically select one or more models of the MD-GMM to modify based on pre-set steps. In some embodiments, if the audio engine 208 detects certain types of segments that may require further scrutiny, it selects the model of the MD-GMM that is most related to the types of segments detected to modify (or for modification). Any model associated with the MD-GMM may be modified. Examples of models that may be modified include the key child model with an age-dependent key child model, an electronic device model, a loudness/clearness model that may further modify the key child model and/or the adult model, and a parentese model that may further modify the key child model and/or the adult model.

In block 406, the audio engine 208 processes the recordings again using the modified models of the MD-GMM. The second process may result in a different segmentation and/or segment ID based on the modified models, providing a more accurate identification of the source associated with each segment.

In block 408, the audio engine 208 determines if additional model modification is needed. In some embodiments, the audio engine 208 analyzes the new segmentation and/or segment ID to determine if any segments or groups of segments require additional scrutiny. In some embodiments, the audio engine 208 accesses data associated with the language environment in data storage 210 and uses it to determine if additional model modification is necessary, such as a modification of the key child model based on the current age of the child. If additional model modification is needed, the process returns to block 404 for additional MD-GMM model modification. If no additional model modification is needed, the process proceeds to block 410 to analyze segment sound. The following describes certain embodiments of modifying exemplary models in accordance with various embodiments of the present invention. Other models than those described below may be modified in certain embodiments of the present invention.

Age-Dependent Key Child Model

In some embodiments of the present invention, the audio engine 208 may implement an age-dependent key child model concurrently with, or subsequent to, the initial MD-GMM to modify the key child model of the MD-GMM to more accurately identify segments in which other children are the source from segments in which the key child is the source. For example, the MD-GMM may be modified to implement an age-dependent key child model during the initial or a subsequent segmentation and segment ID.

The key child model can be age dependent since the audio characteristics of the vocalizations, including utterances and other sounds, of a key child change dramatically over the time that the recorder 108 may be used. Although the use of two separate models within the MD-GMM, one for the key child and one for other children, may identify the speech of the key child, the use of an age-dependent key child model further helps to reduce the confusion between speech of the key child and speech of the other children. In one embodiment, the age-dependent key child models are: 1) less than one-year old, 2) one-year old, 3) two-years old, and 4) three-years old. Alternative embodiments may use other age groupings and/or may use groupings of different age groups. For example, other embodiments could use monthly age groups or a combination of monthly and yearly age groups. Each of the models includes characteristics associated with sounds commonly identified with children of the age group.

In one embodiment of the present invention, the age of the key child is provided to device 200 via input device 212 during a set-up or configuration. The audio engine 208 receives the age of the key child and selects one or more of the key child models based on the age of the key child. For example, if the key child is one year and ten months old, the audio engine 208 may select key child model 2 (one-year-old model) and key child model 3 (two-years-old model) or only key child model 2 based on the age of the key child. The audio engine 208 may implement the selected key child model or models by modifying the MD-GMM models to perform the initial or a subsequent segmentation and segment ID.

Electronic Device Model

In order to more accurately determine the number of adult words that are directed to the key child, any segments including sounds, such as words or speech, generated electronically by an electronic device can be identified as such, as opposed to an inaccurate identification as live speech produced by an adult. Electronic devices can include a television, radio, telephone, audio system, toy, or any electronic device that produces recordings or simulated human speech. In some embodiments of the present invention, the audio engine 208 may modify an electronic device model in the MD-GMM to more accurately identify segments from an electronic device source and separate them from segments from a live adult without the need to determine the content of the segments and without the need to limit the environment of the speaker (e.g., requiring the removal of or inactivation of the electronic devices from the language environment).

The audio engine 208 may be adapted to modify and use the modified electronic device model concurrently with, or subsequent to, the initial MD-GMM process. In some embodiments, the electronic device model can be implemented after a first MD-GMM process is performed and used to adapt the MD-GMM for additional determinations using the MD-GMM for the same recording. The audio engine 208 can examine segments segmented using a first MD-GMM to further identify reliable electronic segments. Reliable electronic segments may be segments that are more likely associated with a source that is an electronic device and include certain criteria. For example, the audio engine 208 can determine if one or more segments include criteria commonly associated with sounds from electronic devices. In some embodiments, the criteria includes (1) a segment that is longer than a predetermined period or is louder than a predetermined threshold; or (2) a series of segments having a pre-set source pattern. An example of one predetermined period is five seconds. An example of one pre-set source pattern can include the following:

Segment 1—Electronic device source;
Segment 2—A source other than the electronic device source (e.g., adult);
Segment 3—Electronic device source;
Segment 4—A source other than the electronic device source; and
Segment 5—Electronic device source.

The reliable electronic device segments can be used to adapt the MD-GMM to include an adaptive electronic device model for further processing. For example, the audio engine 208 may use a regular K-means algorithm as an initial model and tune it with an expectation-maximization (EM) algorithm. The number of Gaussians in the adaptive electronic device model may be proportional to the amount of feedback electronic device data and not exceed an upper limit. In one embodiment, the upper limit is 128.

The audio engine 208 may perform the MD-GMM again by applying the adaptive electronic device model to each frame of the sequence to determine a new adaptive electronic device log-likelihood score for frames associated with a source that is an electronic device. The new score may be compared with previously stored log-likelihood scores for those frames. The audio engine 208 may select the larger log-likelihood score based on the comparison. The larger log-likelihood score may be used to determine the segment ID for those frames.

In some embodiments, the MD-GMM modification using the adaptive electronic device model may be applied using a pre-set number of consecutive equal length adaptation windows moving over all frames. The recording signal may be divided into overlapping frames having a pre-set length. An example of frame length according to one embodiment of the present invention is 25.6 milliseconds with a 10 millisecond shift resulting in 15.6 milliseconds of frame overlap. The adaptive electronic device model may use local data obtained using the pre-set number of adaptation windows. An adaptation window size of 30 minutes may be used in some embodiments of the present invention. An example of one pre-set number of consecutive equal length adaptation windows is three. In some embodiments, adaptation window movement does not overlap. The frames within each adaptation window may be analyzed to extract a vector of features for later use in statistical analysis, modeling, and classification algorithms. The adaptive electronic device model may be repeated to further modify the MD-GMM process. For example, the process may be repeated three times.

Loudness/Clearness Detection Model

In order to select the frames that are most useful for identifying the speaker, some embodiments of the present invention use frame level near/far detection or loudness/clearness detection model. Loudness/clearness detection models can be performed using a Likelihood Ratio Test (LRT) after an initial MD-GMM process is performed. At the frame level, the LRT is used to identify and discard frames that could confuse the identification process. For each frame, the likelihood for each model is calculated. The difference between the most probable model likelihood and the likelihood for silence is calculated and the difference is compared to a predetermined threshold. Based on the comparison, the frame is either dropped or used for segment ID. For example, if the difference meets or exceeds the predetermined threshold, then the frame is used; but if the difference is less than the predetermined threshold, then the frame is dropped. In some embodiments, frames are weighted according to the LRT.

The audio engine 208 can use the LRT to identify segments directed to the key child. For example, the audio engine 208 can determine whether adult speech is directed to the key child or to someone else by determining the loudness/clearness of the adult speech or sounds associated with the segments. Once segmentation and segment ID are performed, segment-level near/far detection is performed using the LRT in a manner similar to that used at the frame level. For each segment, the likelihood for each model is calculated. The difference between the most probable model likelihood and the likelihood for silence is calculated and the difference is compared to a predetermined threshold. Based on the comparison, the segment is either dropped or processed further.

Parentese Model

Sometimes adults use baby talk or "parentese" when directing speech to children. The segments including parentese may be inaccurately associated with a child or the key child as the source because certain characteristics of the speech may be similar to that of the key child or other children. The audio engine 208 may modify the key child model and/or adult model to identify segments including parentese and associate the segments with an adult source. For example, the models may be modified to allow the audio engine 208 to examine the complexity of the speech included in the segments to identify parentese. Since the complexity of adult speech is typically much higher than child speech, the source for segments including relatively complex speech may be identified as an adult. Speech may be complex if the formant structures are well formed, the articulation levels are good, and the vocalizations are of sufficient duration—consistent with speech commonly provided by adults. Speech from a child may include formant structures that are less clear and developed and vocalizations that are typically of a lesser duration. In addition, the audio engine 208 can analyze formant frequencies to identify segments including parentese. When an adult uses parentese, the formant frequencies of the segment typically do not change. Sources for segments including such identified parentese can be determined to be an adult.

The MD-GMM models may be further modified and the recording further processed for a pre-set number of iterations or until the audio engine 208 determines that the segment IDs have been determined with an acceptable level of confidence. Upon completion of the segmentation and segment ID, the identified segment can be further analyzed to extract characteristics associated with the language environment of the key child.

Child Vocalization, Cry, Vegetative-Sound/Fixed-Signal Detection (Classification)

During or after performing segmentation and segment ID, the audio engine 208 may classify key child audio segments into one or more categories. The audio engine 208 analyzes each segment for which the key child is identified as the source and determines a category based on the sound in each segment. The categories can include vocalizations, cries, vegetative-sound, and fixed-signal sounds. Vocalizations can include words, phrases, marginal syllables, including rudimentary consonant-vowel sequences, utterances, phonemes, sequence phonemes, phoneme-like sounds, protophones, lip-trilling sounds commonly called raspberries, canonical syllables, repetitive babbles, pitch variations, or any meaningful sounds which contribute to the language development of the child, indicate at least an attempt by the child to communicate verbally, or explore the capability to create sounds. Vegetative-sound includes non-vocal sounds related to respiration and digestion, such as coughing, sneezing, and burping. Fixed-signal sounds are related to voluntary reactions to the environment and include laughing, moaning, sighing, and lip smacking.

Cries are a type of fixed-signal sound, but are detected separately since cries can be a means of communication.

Figure 6:
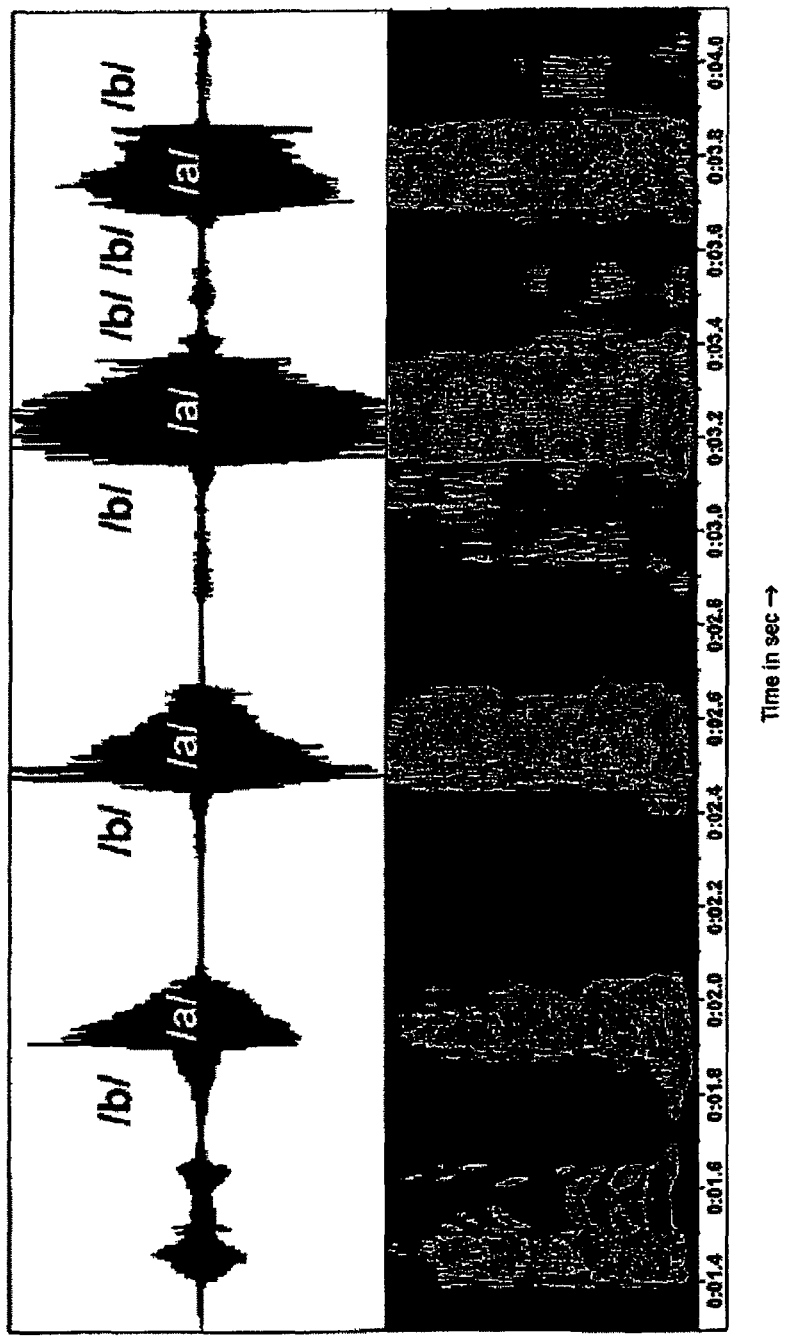
FIG. 6 illustrates sound energy in a segment according to one embodiment of the present invention.

The audio engine 208 may classify key child audio segments using rule-based analysis and/or statistical processing. Rule-based analysis can include analyzing each key child segment using one or more rules. For some rules, the audio engine 208 may analyze energy levels or energy level transitions of segments. An example of a rule based on a pre-set duration is segments including a burst of energy at or above the pre-set duration are identified as a cry or scream and not a vocalization, but segments including bursts of energy less than the pre-set duration are classified as a vocalization. An example of one pre-set duration is three seconds based on characteristics commonly associated with vocalizations and cries. FIG. 6 illustrates energy levels of sound in a segment associated with the key child and showing a series of consonant (/b/) and vowel (/a/) sequences. Using a pre-set duration of three seconds, the bursts of energy indicate a vocalization since they are less than three seconds.

A second rule may be classifying segments as vocalizations that include formant transitions from consonant to vowel or vice versa. FIG. 6 illustrates formant transitions from consonant /b/ to vowel /a/ and then back to consonant /b/, indicative of canonical syllables and, thus, vocalizations. Segments that do not include such transitions may be further processed to determine a classification.

A third rule may be classifying segments as vocalizations if the formant bandwidth is narrower than a pre-set bandwidth. In some embodiments, the pre-set bandwidth is 1000 Hz based on common bandwidths associated with vocalizations.

A fourth rule may be classifying segments that include a burst of energy having a first spectral peak above a pre-set threshold as a cry. In some embodiments, the pre-set threshold is 1500 Hz based on characteristics common in cries.

A fifth rule may be determining a slope of a spectral tilt and comparing it to pre-set thresholds. Often, vocalizations include more energy in lower frequencies, such as 300 to 3000 Hz, than higher frequencies, such as 6000 to 8000 Hz. A 30 dB drop is expected from the first part of the spectrum to the end of the spectrum, indicating a spectral tilt with a negative slope and a vocalization when compared to pre-set slope thresholds. Segments having a slope that is relatively flat may be classified as a cry since the spectral tilt may not exist for cries. Segments having a positive slope may be classified as vegetative-sound.

A sixth rule may be comparing the entropy of the segment to entropy thresholds. Segments including relatively low entropy levels may be classified as vocalizations. Segments having high entropy levels may be classified as cries or vegetative-sound due to randomness of the energy.

A seventh rule may be comparing segment pitch to thresholds. Segments having a pitch between 250 to 600 Hz may be classified as a vocalization. Segments having a pitch of more than 600 Hz may be classified as a cry or squeal, and a pitch of less than 250 Hz may be classified as a growl.

An eighth rule may be determining pitch contours. Segments having a rising pitch may be classified as a happy sound. Segments having a falling pitch may be classified as an angry sound.

A ninth rule may be determining the presence of consonants and vowels. Segments having a mix of consonants and vowels may be classified as vocalizations. Segments having all or mostly consonants may be classified as a vegetative-sound or fixed-signal sound.

A rule according to various embodiments of the present invention may be implemented separately or concurrently with other rules. For example, in some embodiments the audio engine 208 implements one rule only while in other embodiments the audio engine 208 implements two or more rules. Statistical processing may be performed in addition to or alternatively to the rule-based analysis.

Statistical processing may include processing segments with a MD-GMM using 2000 or more Gaussians in which models are created using Mel-scale Frequency Cepstral Coefficients (MFCC) and Subband Spectral Centroids (SSC). MFCCs can be extracted using a number of filter banks with coefficients. In one embodiment, 40 filter banks are used with 36 coefficients. SSCs may be created using filter banks to capture formant peaks. The number of filter banks used to capture formant peaks may be 7 filter banks in the range of 300 to 7500 Hz. Other statistical processing may include using statistics associated with one or more of the following segment characteristics:

Formants;
Formant bandwidth;
Pitch;
Voicing percentage;
Spectrum entropy;
Maximum spectral energy in dB;
Frequency of maximum spectral energy; and
Spectral tilt.

Statistics regarding the segment characteristics may be added to the MFCC-SSC combinations to provide additional classification improvement.

As children age, characteristics associated with each key child segment category may change due to growth of the child's vocal tract. In some embodiments of the present invention, an age-dependent model may be used in addition or alternatively to the techniques described above to classify key child segments. For example, vocalization, cry, and fixed-signal/vegetative-sound models may be created for each age group. In one embodiment, 12 different models are used with Group 1 corresponding to 1 to 2 months old, Group 2 corresponding to 3 to 4 months old, Group 3 corresponding to 5 to 6 months old, Group 4 corresponding to 7 to 8 months old, Group 5 corresponding to 9 to 10 months old, Group 6 corresponding to 11 to 12 months old, Group 7 corresponding to 13 to 14 months old, Group 8 corresponding to 15 to 18 months old, Group 9 corresponding to 19 to 22 months old, Group 10 corresponding to 23 to 26 months old, Group 11 corresponding to 27 to 30 months old, and Group 12 corresponding to 31 to 48 months old. In an alternative embodiment, vocalization, cry, and fixed-signal/vegetative-sound models may be created for each month of age from 1 month to 48 months. This model will include 144 models, 48 models for each category. Alternative embodiments may use a different number of groups or associate different age ranges with the groups.

The audio engine 208 may also identify segments for which an adult is the source. The segments associated with an adult source can include sounds indicative of conversational turns or can provide data for metrics indicating an estimate of the amount or number of words directed to the key child from the adult. In some embodiments, the audio engine 208 also identifies the occurrence of adult source segments to key child source segments to identify conversational turns.

In block 304, the audio engine 208 estimates key child segment characteristics from at least some of the segments for which the key child is the source, independent of content. For example, the characteristics may be determined without determining or analyzing content of the sound in the key child segments. Key child segment characteristics can include any type of characteristic associated with one or more of the key child segment categories. Examples of characteristics include duration of cries, number of squeals and growls, presence and number of canonical syllables, presence and number of repetitive babbles, presence and number of phonemes, protophones, phoneme-like sounds, word or vocalization count, or any identifiable vocalization or sound element.

The length of cry can be estimated by analyzing segments classified in the cry category. The length of cry typically decreases as the child ages or matures and can be an indicator of the relative progression of the child's development.

The number of squeals and growls can be estimated based on pitch, spectral intensity, and dysphonation by analyzing segments classified as vocalizations. A child's ability to produce squeals and growls can indicate the progression of the child's language ability as it indicates the key child's ability to control the pitch and intensity of sound.

The presence and number of canonical syllables, such as consonant and vowel sequences, can be estimated by analyzing segments in the vocalization category for relatively sharp formant transitions based on formant contours.

The presence and number of repetitive babbles may be estimated by analyzing segments classified in the vocalization category and applying rules related to formant transitions, durations, and voicing. Babbling may include certain consonant/vowel combinations, including three voiced stops and two nasal stops. In some embodiments, the presence and number of canonical babbling may also be determined. Canonical babbling may occur when 15% of syllables produced are canonical, regardless of repetition. The presence, duration, and number of phoneme, protophones, or phoneme-like sounds may be determined. As the key child's language develops, the frequency and duration of phonemes increases or decreases or otherwise exhibits patterns associated with adult speech.

The number of words or other vocalizations made by the key child may be estimated by analyzing segments classified in the vocalization category. In some embodiments, the number of vowels and number of consonants are estimated using a phone decoder and combined with other segment parameters such as energy level and MD-GMM log-likelihood differences. A least-square method may be applied to the combination to estimate the number of words spoken by the child. In one embodiment of the present invention, the audio engine 208 estimates the number of vowels and consonants in each of the segments classified in the vocalization category and compares it to characteristics associated with the native language of the key child to estimate the number of words spoken by the key child. For example, an average number of consonants and vowels per word for the native language can be compared to the number of consonants and vowels to estimate the number of words. Other metrics/characteristics can also be used, including phoneme, protophones, and phoneme-like sounds.

In block 306, the audio engine 208 estimates characteristics associated with identified segments for which an adult is the source, independent of content. Examples of characteristics include a number of words spoken by the adult, duration of adult speech, and a number of parentese. The number of words spoken by the adult can be estimated using similar methods as described above with respect to the number of words spoken by the key child. One example of a method to detect adult word count is based on human annotated word-count, using Least-Squared Linear Regression to train. The model may also be guided or trained by human annotated word-count. The duration of adult speech can be estimated by analyzing the amount of energy in the adult source segments.

Language Environment Metric

In block 308, the audio engine 208 can determine one or more metrics associated with the language environment using the key child segment characteristics and/or the adult segment characteristics. For example, the audio engine 208 can determine a number of conversational turns or "turn-taking" by analyzing the characteristics and time periods associated with each segment. In some embodiments, the audio engine 208 can be configured to automatically determine the one or more metrics. In other embodiments, the audio engine 208 receives a command from input device 212 to determine a certain metric.

Metrics can include any quantifiable measurement of the key child's language environment based on the characteristics. The metrics may also be comparisons of the characteristics to statistical averages of the same type of characteristics for other persons having similar attributes, such as age, to the key child. Examples of metrics include average vocalizations per day expressed by the key child, average vocalizations for all days measured, the number of vocalizations per month, the number of vocalizations per hour of the day, the number of words directed to the child from an adult during a selected time period, and the number of conversational turns.

In some embodiments, metrics may relate to the key child's developmental age. In the alternative or in addition to identifying delays and idiosyncrasies in the child's development as compared to an expected level, metrics may be developed that may estimate causes of such idiosyncratic and developmental delays. Examples of causes include developmental medical conditions such as autism or hearing problems.

Figure 7:
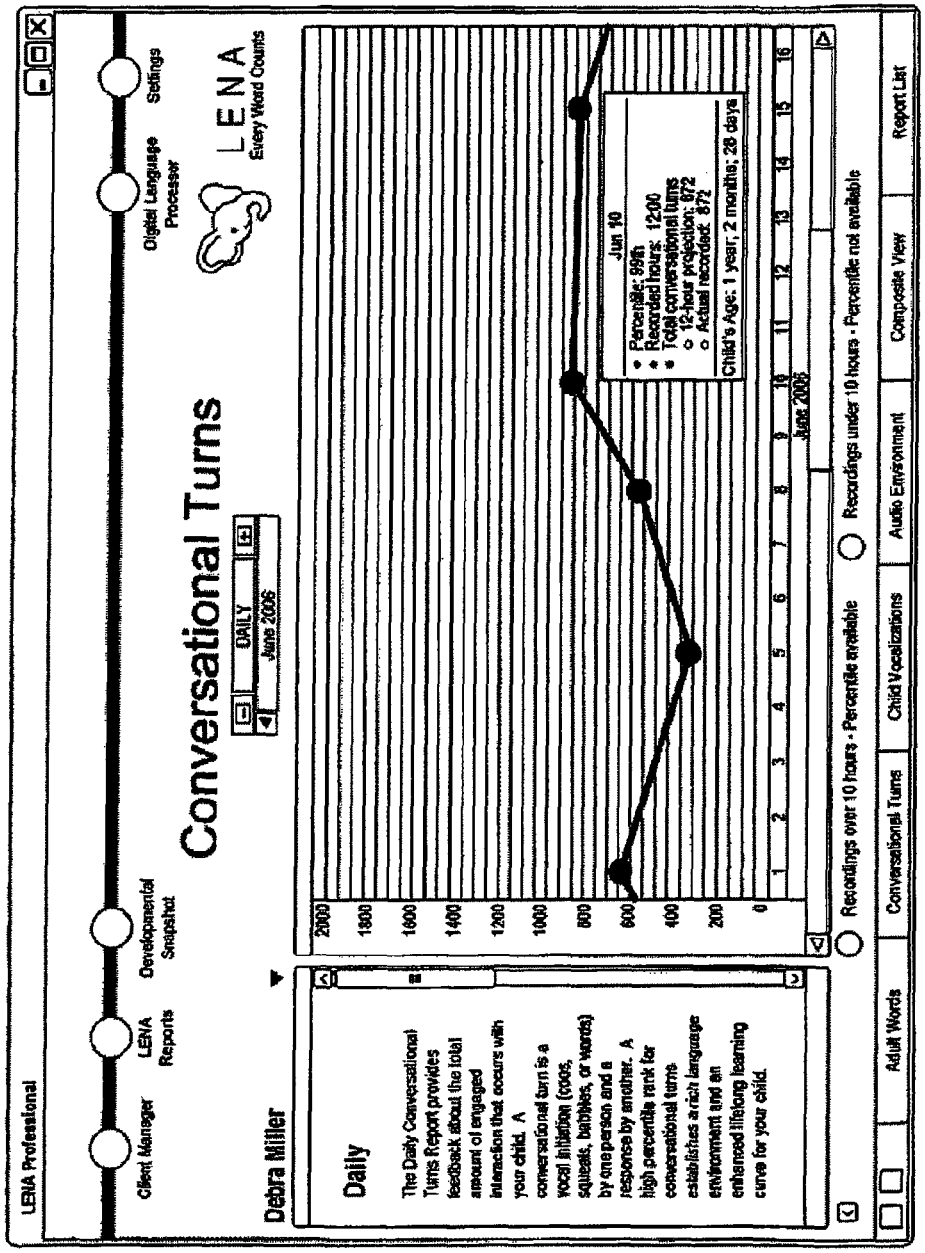
FIGS. 7-12 are screen shots illustrating metrics provided to an output device according to one embodiment of the present invention.
Figure 8:
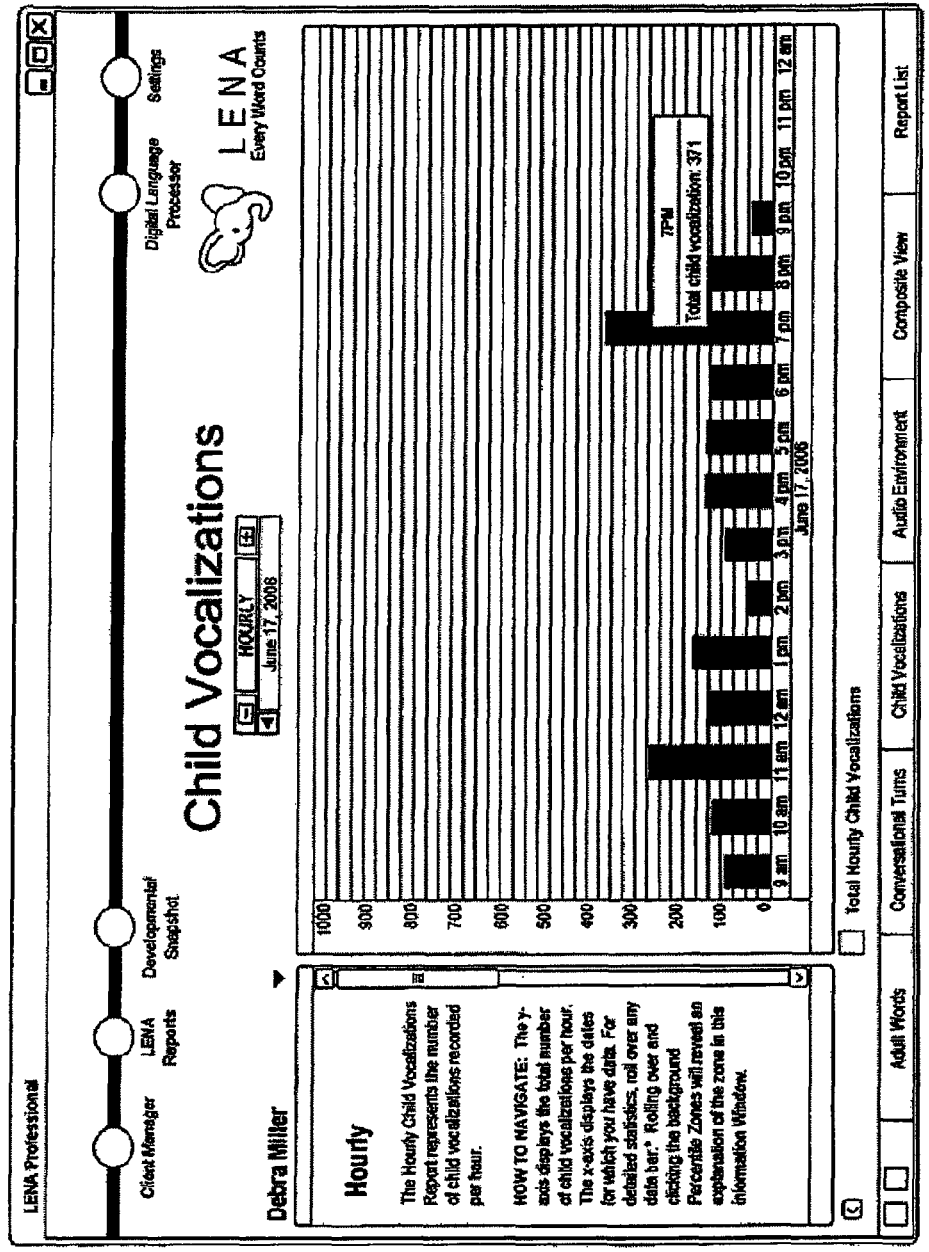
Figure 9:
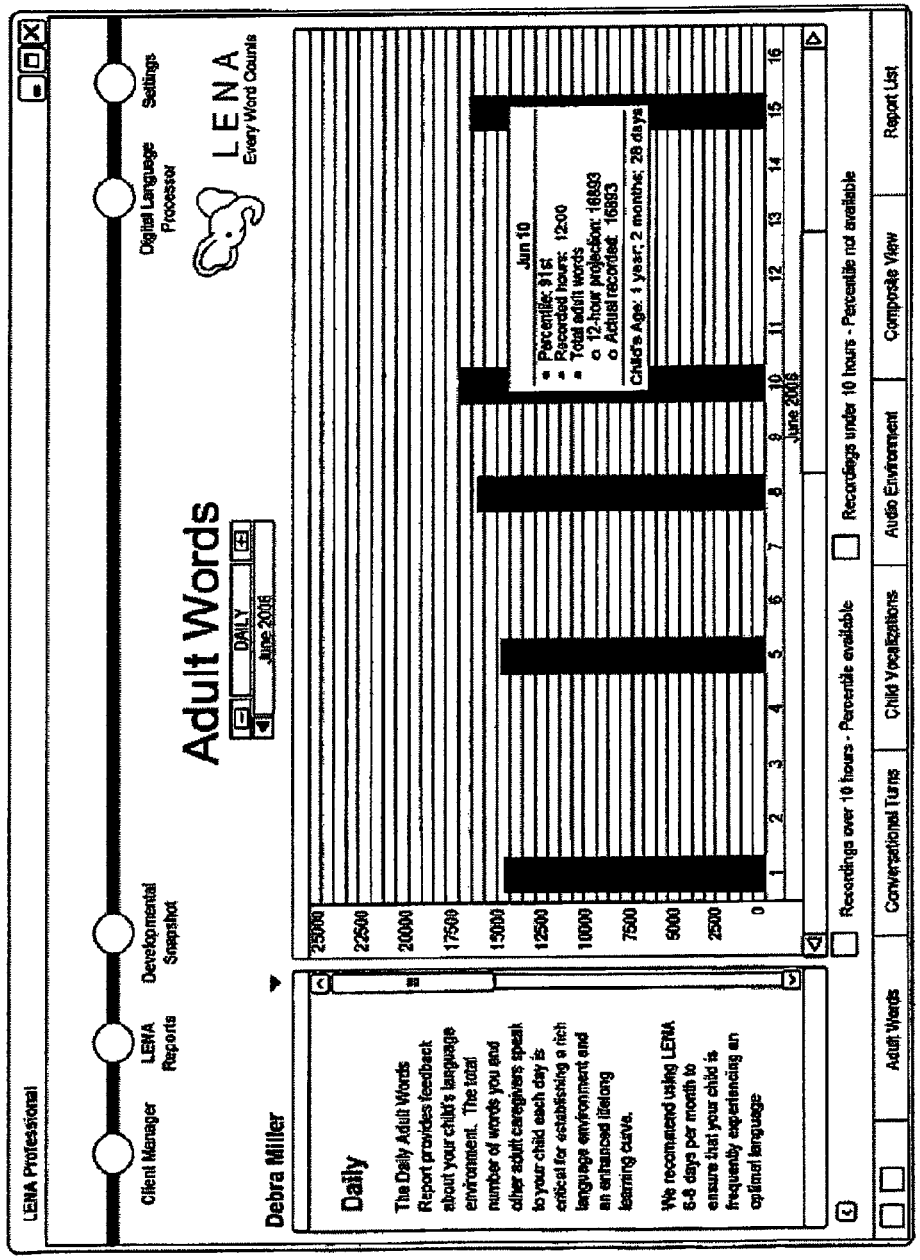
Figure 10:
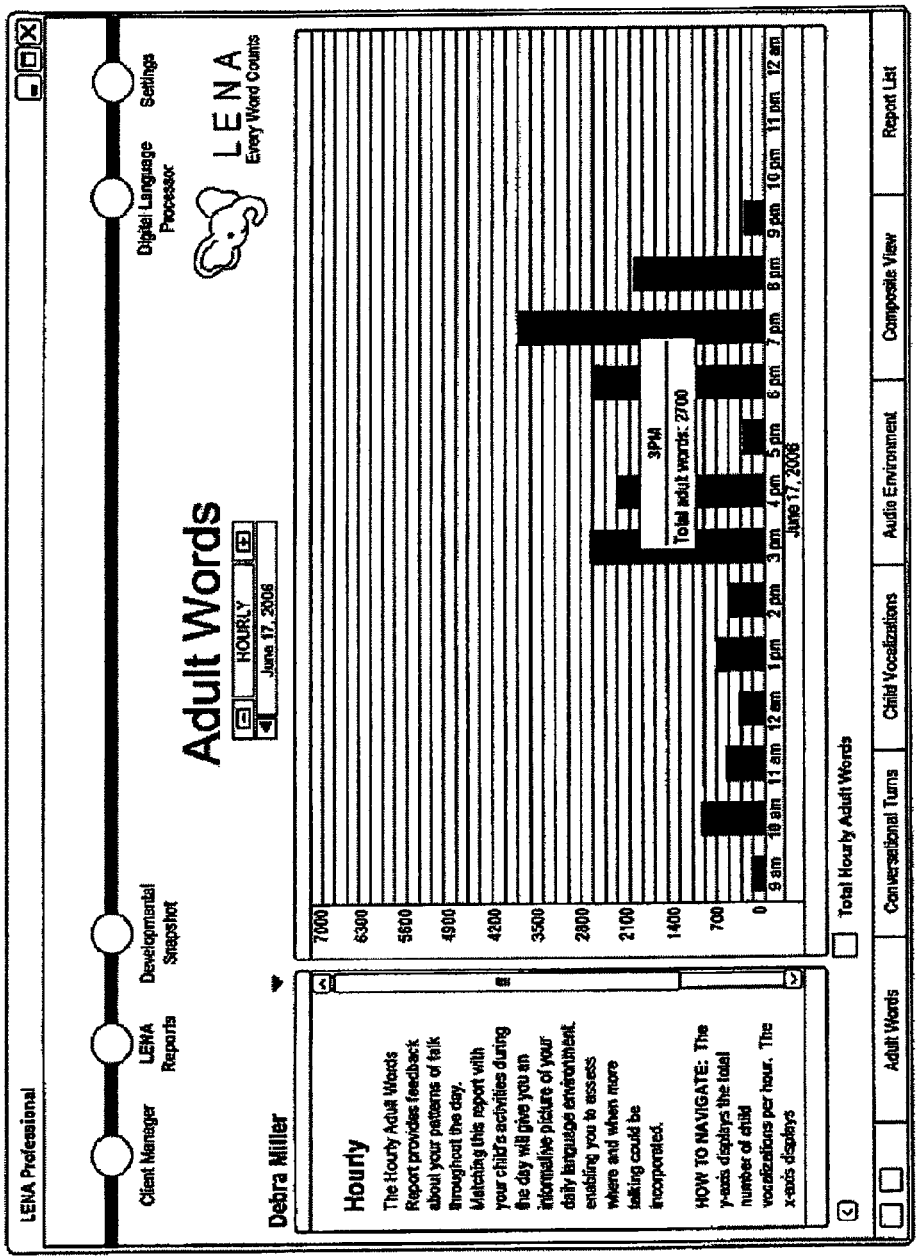
Figure 11:
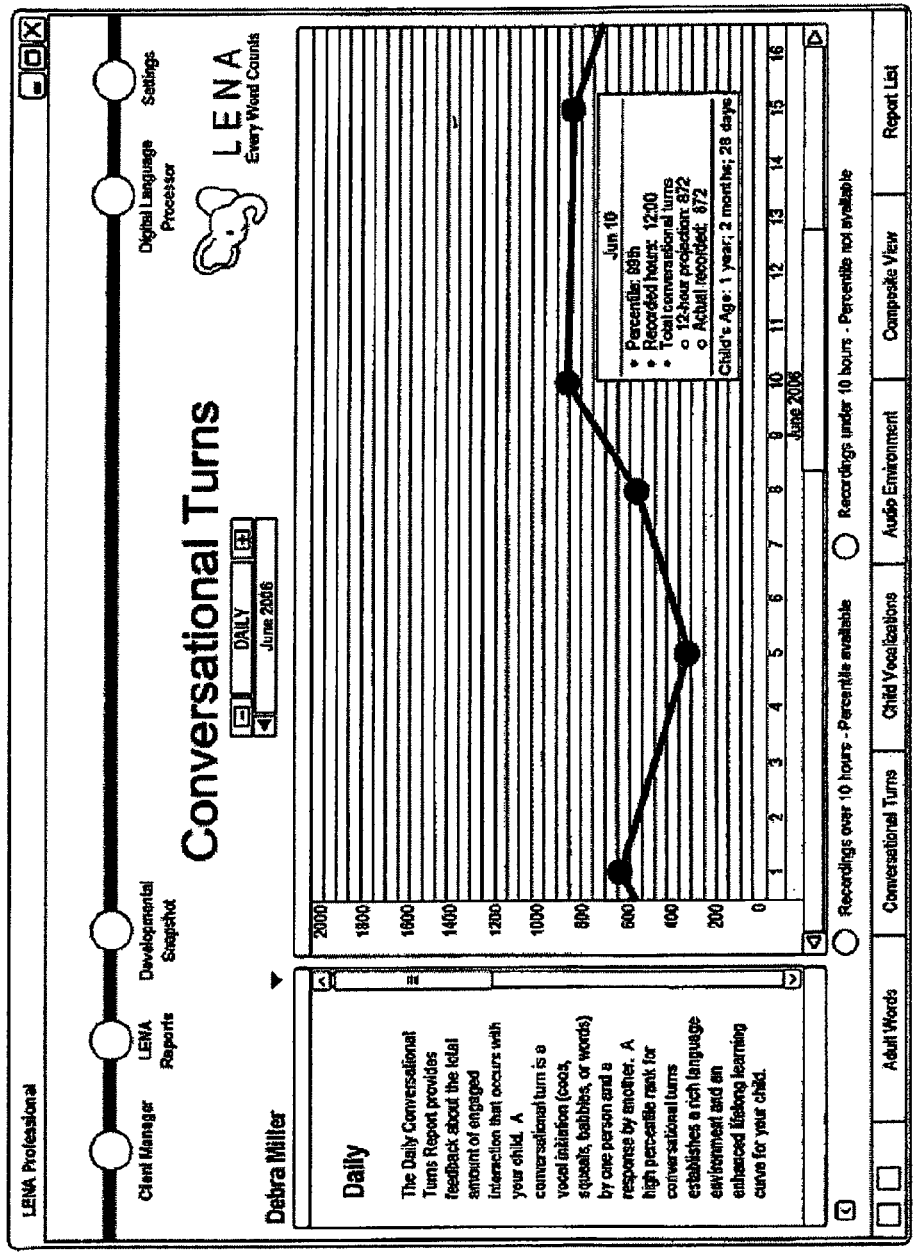
Figure 12:
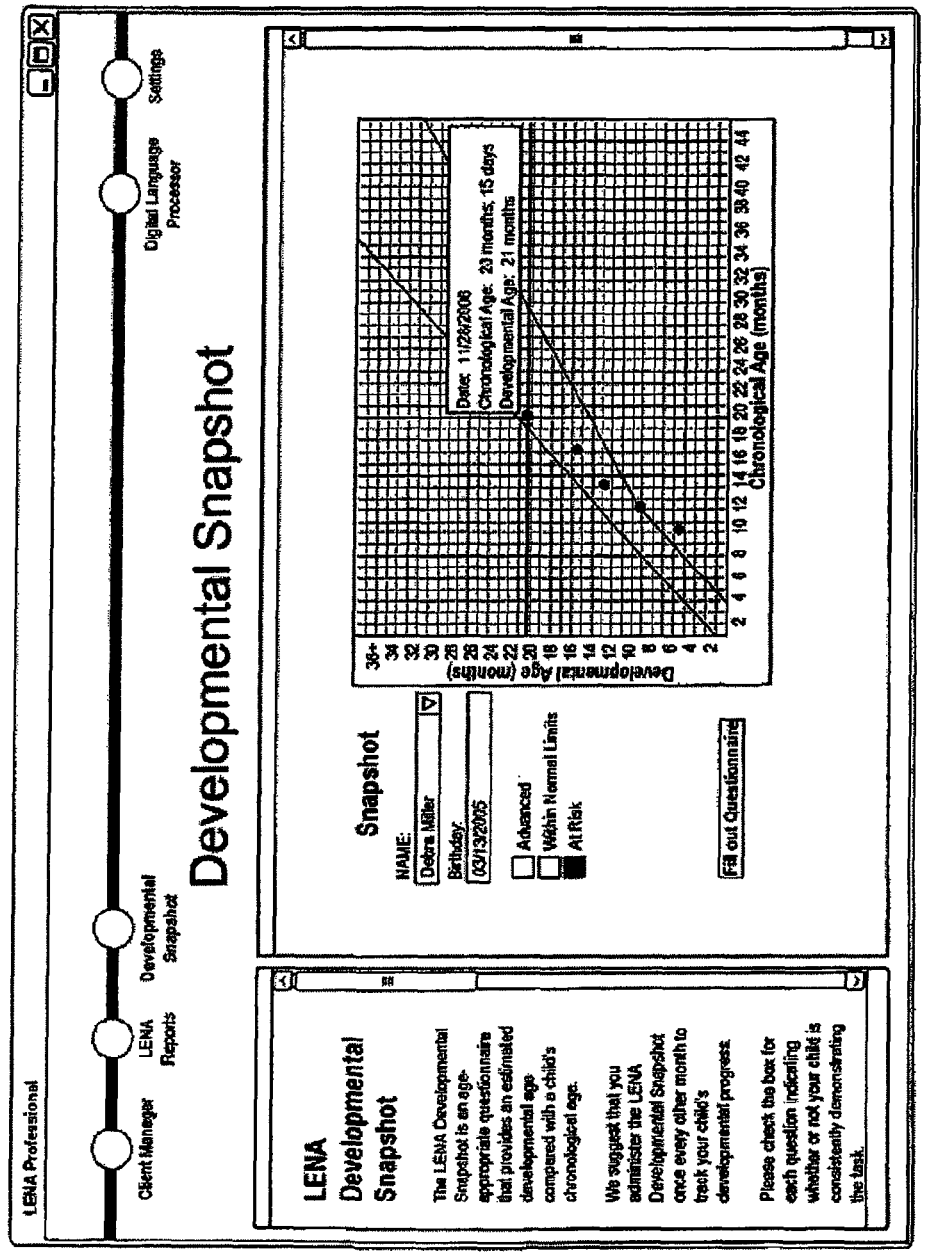

In block 310, the audio engine 208 outputs at least one metric to output device 114. For example, the audio engine 208 may, in response to a command received from input device 212, output a metric associated with a number of words spoken by the child per day to the output device 214, where it is displayed to the user. FIGS. 7-12 are screen shots showing examples of metrics displayed on output device 214. FIG. 7 illustrates a graphical vocalization report showing the number of vocalizations per day attributable to the key child. FIG. 8 illustrates a graphical vocalization timeline showing the number of vocalizations in a day per hour. FIG. 9 illustrates a graphical adult words report showing a number of adult words directed to the key child during selected months. FIG. 10 illustrates a graphical words timeline showing the number of words per hour in a day attributable to the key child. FIG. 11 illustrates a graphical representation of a turn-takings report showing the number of conversational turns experienced by the key child on selected days per month. FIG. 12 illustrates a graphical representation of a key child's language progression over a selected amount of time and for particular characteristics.

Snapshot

In one embodiment, a series of questions are presented to the user to elicit information about the key child's language skills. The questions are based on well-known milestones that children achieve as they learn to speak. Examples of questions include whether the child currently expresses certain vocalizations such as babbling, words, phrases, and sentences. Once the user responds in a predetermined manner to the questions, no new questions are presented and the user is presented with a developmental snapshot of the speaker based on the responses to the questions. In one embodiment, once three "No" answers are entered, indicating that the child does not exhibit certain skills, the system stops and determines the developmental snapshot. The questioning may be repeated periodically and the snapshot developed based on the answers and, in some embodiments, data from recording processing. An example of a snapshot may include the language development chart shown in FIG. 12. In an alternative embodiment, the series of questions is answered automatically by analyzing the recorded speech and using the information obtained to automatically answer the questions.

Certain embodiments of the present invention do not require that the key child or other speakers train the system, as is required by many voice recognition systems. Recording systems according to some embodiments of the present invention may be initially benchmarked by comparing certain determinations made by the system with determinations made by reviewing a transcript. To benchmark the performance of the segmenter, the identification of 1) key child v. non-key child and 2) adult v. non-adult were compared, as well as the accuracy of the identification of the speaker/source associated with the segments.

Although the foregoing describes the processing of the recorded speech to obtain metrics, such as word counts and conversational turns, other types of processing are also possible, including the use of certain aspects of the invention in conventional speech recognition systems. The recorded speech file could be processed to identify a particular word or sequence of words or the speech could be saved or shared. For example, a child's first utterance of "mama" or "dada" could be saved much as a photo of the child is saved or shared via e-mail with a family member.

Expressive Language Assessment

Each language has a unique set of sounds that are meaningfully contrastive, referred to as a phonemic inventory. English has 42 phonemes, 24 consonant phonemes and 18 vowel phonemes. A phoneme is the smallest phonetic unit in a language that is capable of conveying a distinction in meaning. A sound is considered to be a phoneme if its presence in a minimal word pair is associated with a difference in meaning. For example, we know that /t/ and /p/ are phonemes of English because their presence in the same environment results in a meaning change (e.g., "cat" and "cap" have different meanings). Following linguistic conventions, phonemes are represented between slashes, such as /r/.

One embodiment that automatically assesses the key child's language development uses a phone decoder from an automatic speech recognition ("ASR") system used to recognize content from adult speech. One example is the phone detector component from the Sphinx ASR system provided by Carnegie Mellon University. The phone decoder recognizes a set of phones or speech sounds, including consonant-like phones, such as "t" and "r" and vowel-like phones such as "er" and "ey". ASR phones are approximates of phonemes; they are acoustically similar to true phonemes, but they may not always sound like what a native speaker would categorize as phonemic. These pseudo-phonemes are referred to herein as "phones" or "phone categories" and are represented using quotation marks. For example, "r" represents phone or phoneme-like sounds.

Models from systems designed to recognize adult speech have not been successfully used to process child vocalizations due to the significant differences between adult speech and child vocalizations. Child vocalizations are more variable than adult speech, both in terms of pronunciation of words and the language model. Children move from highly unstructured speech patterns at very young ages to more structured patterns at older ages, which ultimately become similar to adult speech especially around 14 years of age. Thus, ASR systems designed to recognize adult speech have not worked when applied to the vocalizations or speech of children under the age of about 6 years. Even those ASR systems designed for child speech have not worked well. The exceptions have been limited to systems that prompt a child to pronounce a particular predetermined word.

The variability of child speech also makes it difficult to develop models for ASR systems to handle child vocalizations. Most ASR systems identify phonemes and words. Very young children (less than 12 months of age) do not produce true phonemes. They produce protophones, which may acoustically look and sound like a phoneme but are not regular enough to be a phoneme and may not convey meaning. The phone frequency distribution for a child is very different from the phone frequency distribution for an adult.

For example, a very young child cannot produce the phoneme /r/, so not many "r" phones appear. However, over time more and more "r" phones appear (at least for an English-speaking child) until the child really does produce the /r/ phoneme. A very young child may not attribute meaning to a protophone or phone. A child begins to produce true phonemes about the time that they start to talk (usually around 12 months of age), but even then the phonemes may only be recognized by those who know the child well. However, even before a child can produce a true phoneme, the child's vocalizations can be used to assess the child's language development.

Although an adult ASR model does not work well with child speech, one embodiment of the present invention uses a phone decoder of an ASR system designed for adult speech, since the objective is to assess the language development of a child independent of the content of the child's speech. Even though a child does not produce a true phoneme, the phone decoder is forced to pick the phone category that best matches each phone produced by the child. By selecting the appropriate phone categories for consideration, the adult ASR phone decoder can be used to assess child vocalizations or speech.

As shown with the "r" phone, there is some correlation between the frequency of a phone and chronological age. The correlation can be positive or negative. The relationship varies for different age ranges and is non-linear for some phones. FIG. 13 describes the correlation between selected phones and chronological age. As shown in FIG. 13, there is a positive correlation between age and the "r" phone and a negative correlation between age and the "b" phone. As shown in FIG. 14, the correlation can be non-linear over the age range of interest. For example, the correlation for the "1" phone is positive for ages 0 to 6 months, 7 to 13 months, and 14 to 20 months, but then becomes negative for ages 21 to 30 months and 31+ months.

To assess the language development of a child, one embodiment uses one or more recordings taken in the child's language environment. Each recording is processed to identify segments within the recording that correspond to the child with a high degree of confidence. Typically, the recording will be around 12 hours in duration in which the child produces a minimum of 3000 phones. As described in more detail above, multiple models can be used to identify the key child segments, including, but not limited to, an age-based key child model, an other-child model, a male adult model, a female adult model, an electronic device model, a silence model, and a loudness/clearness model. The use of these models allows the recording to be taken in the child's language environment rather than requiring that the recording be taken in a controlled or clinical environment.

The phone decoder processes the high confidence key child segments (i.e., key child segments that are deemed to be sufficiently clear), and a frequency count is produced for each phone category. The frequency count for a particular phone represents the number of times that the particular phone was detected in the high confidence key child segments. A phone parameter $PC_n$ for a particular phone category n represents the frequency count for that phone category divided by the total number of phones in all phone categories. One particular embodiment uses 46 phone categories where 39 of the phone categories correspond to a speech sound (see FIG. 13) and 7 of the phone categories correspond to non-speech sounds or noise (filler categories), such as sounds that correspond to a breath, a cough, a laugh, a smack, "uh", "uhum," "um" or silence. Other embodiments may use phone decoders other than the Sphinx decoder. Since different phone decoders may identify different phone categories and/or different non-phone categories, the particular phone and non-phone categories used may vary from that shown in FIGS. 12 and 13. To calculate an expressive language index z-score for the key child, $EL_Z$(key child), the phone parameters PCn are used in the following equation:

$$EL_Z(\text{key child}) = b_1(\text{AGE}) * PC_1 + b_2(\text{AGE}) * PC_2 + \ldots + b_{46}(\text{AGE}) * PC_{46} \qquad (1)$$

The expressive language index includes a weight $b_n$(age) associated with each phone category n at the age (AGE) of the key child. For example, $b_1(12)$ corresponds to the weight associated with phone category 1 at an age of 12 months, and $b_2(18)$ corresponds to the weight associated with phone category 2 at an age of 18 months. The weights $b_n$(age) in the expressive language index equation may differ for different ages, so there is a different equation for each monthly age from 2 months to 48 months. In one embodiment, the equation for a 12-month-old child uses the weights shown in the "12 months" column in FIG. 15. The derivation of the values for the weights $b_n$(age) is discussed below.

To enhance interpretability and to conform to the format that is commonly used in language assessments administered by speech language pathologists ("SLPs"), such as PLS-4 (Preschool Language Scale-4) and REEL-3 (Receptive Expressive Emergent Language-3), the expressive language index can be standardized. This step is optional. Equation (2) modifies the distribution from mean=0 and standard deviation=1 to mean=100 and standard deviation=15 to standardize the expressive language index and to produce the expressive language standard score $EL_{SS}$.

$$EL_{SS} = 100 + 15 * EL_Z(\text{Key Child}) \qquad (2)$$

SLP-administered language assessment tools typically estimate developmental age from counts of observed behaviors. Using a large sample of children in the age range of interest, developmental age is defined as the median age for which a given raw count is attained. In one embodiment of the system, the phone probability distribution does not generate raw counts of observed behaviors, and development age is generated in an alternative approach as an adjustment upward or downward to a child's chronological age. In this embodiment, the magnitude of the adjustment is proportional both to the expressive language standard score ($EL_{SS}$) and to the variability in $EL_{SS}$ observed for the child's chronological age.

Boundary conditions are applied to prevent nonsensical developmental age estimates. The boundary conditions set any estimates that are greater than 2.33 standard deviations from the mean (approximately equal to the 1st and 99th percentiles) to either the $1^{st}$ or $99^{th}$ percentiles. An age-based smoothed estimate of variability is shown below in equation (3). The determination of the values shown in equation (3) other than age is discussed below.

$$SD_{AGE}=0.25+0.02*\text{Age} \quad (3)$$

To determine the child's expressive language developmental age, $EL_{DA}$, the child's chronological age is adjusted as shown below in equation (4). The determination of the constant value shown in equation (4) is discussed below.

$$EL_{DA}=\text{Chronological Age}+\text{Constant}*SD_{AGE}*EL_{SS} \quad (4)$$

In one embodiment for a 12 month old, the expressive language developmental age is calculated using a chronological age of 12 and a constant of 7.81 as shown below:

$$EL_{DA}=12+7.81*SD_{AGE}*EL_{SS} \quad (5)$$

The system can output the child's EL standard score, $EL_{SS}$, and the child's EL developmental age, $EL_{DA}$. Alternatively, the system can compare the child's chronological age to the calculated developmental age and based on the comparison output a flag or other indicator when the difference between the two exceeds a threshold. For example, if the $EL_{SS}$ is more than 1.5 standard deviations lower than normal, then a message might be output suggesting that language development may be delayed or indicating that further assessment is needed.

The validity of the EL model was tested by comparing EL standard scores and EL developmental ages to results derived from the assessments administered by the SLPs. The EL developmental age correlated well with chronological age ($r=0.95$) and with the age estimate from the SLP administered assessments at $r=0.92$. The EL standard score is an accurate predictor of potential expressive language delay. Using a threshold score of 77.5 (1.5 standard deviations below the mean), the EL standard score correctly identified 68% of the children in one study who fell below that threshold based on an SLP assessment. Thirty-two percent of the children identified as having possible delays had below average EL scores, but did not meet the 77.5 threshold score. Only 2% of the non-delayed children were identified as having possible delay based on their EL score.

One way of increasing the accuracy of the EL assessment is to average the EL scores derived from three or more recording sessions. One embodiment averages three EL scores derived from three recordings made on different days for the same key child. Since the models are based on an age in months, the recordings should be taken fairly close together in time. Averaging three or more EL scores increases the correlation between the EL scores and the SLP assessment scores from $r=0.74$ to $r=0.82$.

Combining the EL developmental age with results from a parent questionnaire also increases the accuracy of the EL assessment. The LENA Developmental Snapshot questionnaire is one example of a questionnaire that uses a series of questions to the parent to elicit information about important milestones in a child's language development, such as identifying when the child begins to babble, uses certain words, or constructs sentences. The LENA Developmental Snapshot calculates a developmental age based on the answers to the questions. The questionnaire should be completed at or very near the time the recording session takes place. By averaging the developmental age calculated by the questionnaire and the developmental age calculated by the EL assessment, the correlation between the calculated estimate and the SLP estimate increases to approximately $r=0.82$. If three or more EL scores and the questionnaire results are averaged, then the correlation is even greater, approximately $r=0.85$. Methods other than simple averaging likely will yield even higher correlations. If the questionnaire includes questions directed to receptive language development, as well as expressive language development, then the correlation may be even greater.

Although the foregoing example detects single phones and uses the frequency distribution of the single phones to estimate a standard score and developmental age, it may also be possible to use the frequency distribution for certain phone sequences in a similar manner. For example, it may be possible to use the frequency distributions of both single phones and phone sequences in an equation that includes different weights for different single phones and phone sequences for different ages. In one embodiment, bi-phone sequences may be used instead of single phones and in another embodiment, tri-phone sequences may be used. In yet another embodiment, combinations of phones and bi-phones or phones, bi-phones, and tri-phones may be used. The invention is not limited in use to phones, bi-phones, or tri-phones.

Bi-phone (or the usage of more than one phone) allows for the incorporation of sequence information. In language, phones tend to occur in a logical sequence; therefore, additional resolution is gained by analyzing not just the phones but the sequence of the phones. Bi-phones are defined as each pair of adjacent phones in a decoded sequence. For example, the decoded phone sequence "P A T" contains the phone pairs "P-A" and "A-T". Following from the above example, a tri-phone sequence in this case would be "P A T." Note that uni-phones are included as a single phone paired with an utterance start or stop marker.

The bi-phone frequencies then are used as the input to the same type of linear regression models described above for the uni-phone case. The introduction of bi-phone or tri-phone also introduces a challenging technical issue, i.e., the dimension of bi-phone (total number of bi-phone) is significantly larger than uni-phone (n-squared versus n), and the dimension of tri-phone (n-raised-power-to-3) is even much bigger than that of both bi-phone and uni-phone. Given 46 phone categories plus the utterance start and end markers, the total number of possible pairs is 48*48=2304. It may be problematic to include such high dimensional input to a linear regression; the sheer number of predictors could easily lead to the trained regression model overfitting to the training data, resulting in poor generalization to novel samples. It is possible that, with a sufficient amount of data, this issue will cease to exist. The large dimension makes the model size bigger which needs much more data to train. Principal Component Analysis (PCA) is used to reduce the large dimension to small ones. For bi-phone, the current data shows that the dimension reduced from 2000 to around 50 gives the best result.

To resolve this issue, in one alternative embodiment, principle component analysis (PCA) is used to reduce the dimensions of the bi-phone space from over 2300 to under 100. PCA is a data-driven statistical analysis tool for data compression, dimension reduction, etc. The much lower dimensioned subspace of the data with the most data "spread" or "distribution" is the principal component subspace to be searched. For a one-dimension subspace, the data "spread" could be quantified as the variance. Extensive experimentation has suggested that reducing the bi-phone PCA space to 50 dimensions provided optimal results. The over 2300 bi-phone combinations were reduced to 50 principal components to use as predictors in multiple linear regression models predicting SLP-based scores, exactly as described above in the uni-phone case. The bi-phone approach to estimating improves the correlation with SLP-based expressive language composite scores (r=0.75, p<0.01) compared to the uni-phone approach (r=0.72, p<0.01), both under the leave-one-child-out cross-validation method.

The following is a brief description of PCA. For a set of data $\{x_i | i=1, \ldots, n\}$, the PCA optimal linear transform could be constructed in the following way:
1. Calculate covariance matrix $S=\Sigma(x_i-m)(x_i-m)^T$, where m is the mean of the data set.
2. Calculate sorted eigenvalues and associated eigenvectors: $[\lambda_1, \lambda_2, \ldots, \lambda_n]$, $[v_1, \ldots, v_n]$ where $Sv_i=\lambda_i v_i$ and $\lambda_i \geq \lambda_{i+1}$.
3. To reduce the dimension after linear transform, the first m components could be chosen to construct linear transform, where m<n.
4. The new feature would be $y=[v_1, \ldots, v_m]T^x$.

In the actual experiments, the first step was tried with mean removed and without mean removed. For the current data, there is no fundamental difference between them.

Another alternative embodiment uses phone duration rather than phone frequency. In this embodiment, the phone decoder determines the length of time or duration for each phone category. A phone duration parameter $PC_n$ for a particular phone category n represents the duration for that phone category divided by the total duration of phones in all phone categories. To calculate an expressive language index z-score for the key child, the phone duration parameters are used in an equation that is similar to equation (1), but that uses different weights. The weights may be calculated in a matter similar to that used to calculate weights for frequency distribution.

Estimated Mean Length of Utterance

Speech and language professionals have traditionally used "mean length of utterance" (MLU) as an indicator of child language complexity. This measurement, originally formalized by Brown, assumes that since the length of child utterances increases with age, one can derive a reasonable estimate of a child's expressive language development by knowing the average length of the child's utterances or sentences. See Brown, R., *A First Language: The Early Stages*, Cambridge, Mass., Harvard University Press (1973). Brown and others have associated utterance length with developmental milestones (e.g., productive use of inflectional morphology), reporting consistent stages of language development associated with MLU. Utterance length is considered to be a reliable indicator of child language complexity up to an MLU of 4 to 5 morphemes.

To aid in the development of an MLU-equivalent measure based on phone frequency distributions, transcribers computed the MLU for 55 children 15 to 48 months of age (approximately two children for each age month). The transcribers followed transcription and morpheme-counting guidelines described in Miller and Chapman, which were in turn based on Brown's original rules. See Miller, J. F. & Chapman, R. S., "The Relation between Age and Mean Length of Utterance in Morphemes", Journal of Speech and Hearing Research, Vol. 24, pp. 154-161 (1981). They identified 50 key child utterances in each file and counted the number of morphemes in each utterance. The MLU was calculated by dividing the total number of morphemes in each transcribed file by 50.

In addition to the expressive language standard score ($EL_{SS}$) and developmental age ($EL_{DA}$), the system produces an Estimated Mean Length of Utterance (EMLU). In one embodiment, the EMLU may be generated by predicting human-derived MLU values directly from phone frequency or phone duration distributions, similar to the estimate of the expressive language estimate $EL_Z$. In another embodiment, the EMLU may be generated based on simple linear regression using developmental age estimates to predict human-derived MLU values. For example, $$EMLU=0.297+0.067*EL_{DA} \qquad (6).$$

Derivation of Equation Values

To aid in the development of the various models used to analyze child speech described herein, over 18,000 hours of recordings of 336 children from 2 to 48 months of age in their language environment were collected. Hundreds of hours of these recordings were transcribed, and SLPs administered over 1900 standard assessments of the children, including PLS-4 and/or REEL-3 assessments. The vast majority of the recordings correspond to children demonstrating normal language development. This data was used to determine the values in equations (1), (2)-(5), and (6).

For example, the observations and assessments for each child were averaged together and transformed to a standard z-score to produce an expressive language index value for each child for a particular age. The phone category information output from the Sphinx phone decoder was used along with multiple linear regression to determine the appropriate weights for the expressive language index for each age.

An iterative process was used to determine the set of weights ($b_1(AGE)$ to $b_{46}(AGE)$) for equation (1). In the first step, data for children of a certain month of age were grouped together to determine a set of weights for each age group. For example, data from 6-month olds was used to create a set of weights for the expressive language index for a 6-month old. In the next step, data for children of similar ages was grouped together to determine a different set of weights for each age group. For example, data from 5-, 6-, and 7-month olds was used to create a different set of weights for the expressive language index for a 6-month old. In subsequent steps, data for children of additional age ranges were included. For example, data from 4-, 5-, 6-, 7-, and 8-month olds were used to create a different set of weights for the expressive language index for a 6-month old, etc. This process was repeated for all age months and across increasingly broad age ranges. A dynamic programming approach was used to select the optimal age range and weights for each monthly age group. For example, in one embodiment, at age 12 months, the age band is from age 6 months to age 18 months and the weights are shown in the table in FIG. 15. FIG. 15 also illustrates the weights for another example for a key child aged 6 months with an age band from 3 months to 9 months, and the weight for a key child aged 18 months with an age band from 11 months to 25 months. Although the age ranges in these examples are symmetric, the age ranges do not have to be symmetric and typically are not symmetric for ages at the ends of the age range of interest.

The calculated weights were tested via the method of Leave-One-Out Cross-Validation (LOOCV). The above iterative process was conducted once for each child (N=336), and in each iteration the target child was dropped from the training dataset. The resultant model was then used to predict scores for the target child. Thus, data from each participant was used to produce the model parameters in N−1 rounds. To confirm the model, the Mean Square Error of prediction averaged across all models was considered. The final age models included all children in the appropriate age ranges.

Exemplary EL System

Figure 16:
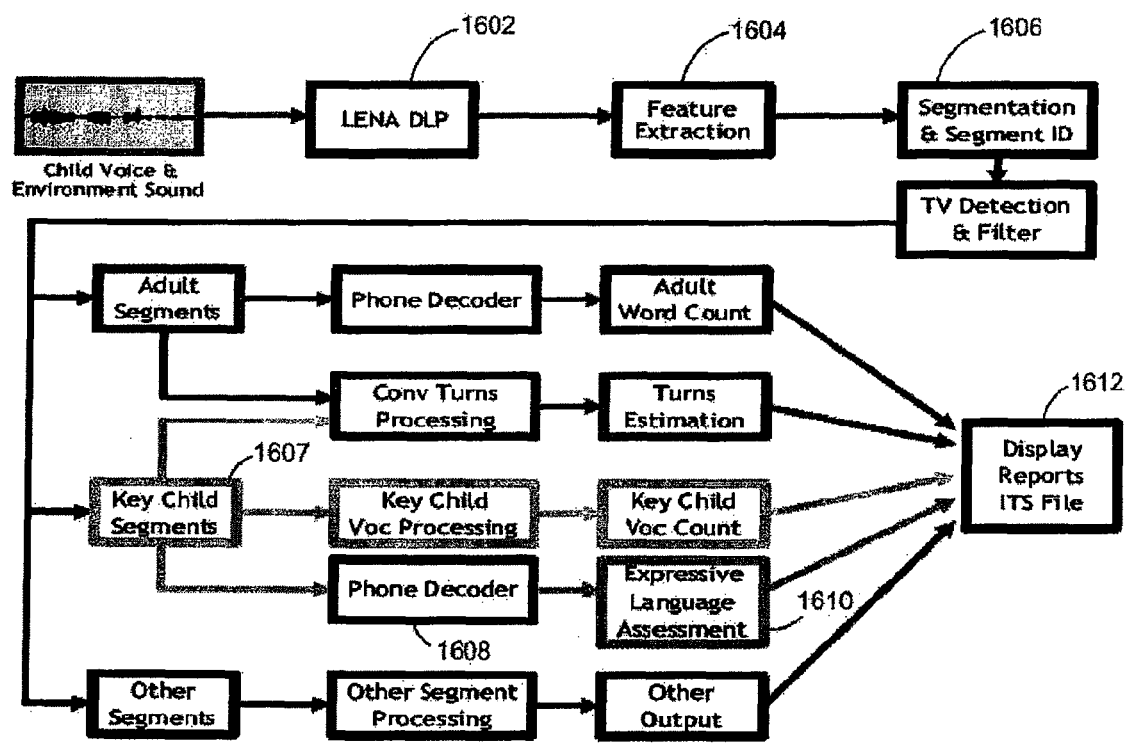
FIG. 16 is a block diagram illustrating the system used to assess language development according to one embodiment of the present invention.

FIG. 16 illustrates a block diagram for an exemplary system that computes an EL score and developmental age as described above. The illustrated system includes a digital recorder 1602 for recording audio associated with the child's language environment. The recorded audio is processed by the feature extraction component 1604 and segmentation and segment ID component 1606 to extract high confidence key child segments. A phone decoder 1608 based on a model used to recognize content from adult speech processes the high confidence key child segments 1607. The phone decoder provides information on the frequency distribution of certain phones to the EL component 1610. The EL component uses the information to calculate the EL score, estimate the developmental age, and/or estimate the mean length of utterances as described above. The Reports and Display component 1612 outputs the EL information as appropriate.

Although FIG. 16 illustrates that a recording is processed using a system that processes recordings taken in the child's language environment, such as the LENA system, the EL assessment can operate with key child segments generated in any manner, including recordings taken in a clinical or research environment, or segments generated using a combination of automatic and manual processing.

Autism Detection

In one embodiment, a system and method for detecting autism uses the automatic language processing system and methodologies described above. Recordings captured in a natural language environment are processed, and a model of the language development of those known subjects is created. By using a large enough sample, trends in language development can be determined. This is referred to as normative trends. Generally, if there is a particular developmental disorder that is desired to be studied, then the language of individuals having the disorder and normal individuals is studied and trends are developed. The methodology described herein is an example of how a particular developmental disorder, autism, may be detected using language analysis. The method and system, however, may be applied to a variety of disorders and diseases, for example autism and Alzheimer's disease. All diseases and disorders that may be detected through the analysis of language may be detected through this embodiment.

In the case of autism, aberrations in the voice of individuals have been noted in the descriptions of Autism Spectrum Disorders (ASD). It has been shown in numerous studies that autism is indeed associated with abnormalities of vocal quality, prosody, and other features of speech. See R. Paul, A. Augustyn, A. Klin, F. R. Volkmar, Journal of Autism and Developmental Disorders 35, 205 (2005); W. Pronovost, M. P. Wakstein, D. J. Wakstein, Exceptional Children 33, 19 (1966); and S. J. Sheinkopf, P. Mundy, D. K. Oiler, M. Steffens, Journal of Autism and Developmental Disorders 30, 345 (2000). However, these features of speech are not easily detected or identified; therefore, the definition of autism (DSM-IV-TR, APA, 2000) does not include a description of what such features may include.

In this embodiment, autism may be affirmatively detected based on positive markers based on the characteristics of speech that could not previously be performed. Generally, autism is detected by using "negative markers," such as a deficit in joint attention. See, for example: S. Baron-Cohen, J. J Allen, C. Gillberg, The British Journal of Psychiatry 161, 839 (1992); K. A. Loveland, S. H. Landry, Journal of Autism and Developmental Disorders 16, 335 (1986); and P. Mundy, C. Kasari, M. Sigman, Infant Behavior and Development 15, 377 (1992).

The method used in determining autism in children may be described as Child Speech Analysis using Transparent Parameters (CSATP). Roughly, Transparent Parameters are those parameters that may be extracted from the sound signal and are independent of the actual content of the sound signal in terms of meaning of the language or sounds produced. Transparent parameters are discussed further below. CSATP includes a number of steps: segmentation; VOC, CRY, and VEGFIX Classification and vocalization count; acoustic analysis; extraction of transparent parameters; and data set classification. Using this methodology and a sample of sufficient size of children having normal speech development, delayed speech development, and autism, trends in language may be developed for these groups. See the above discussion of VOC, CRY, and VEG-FIX classification in relation to audio engine 208 that may classify key child audio segments into one or more categories.

Figure 17:
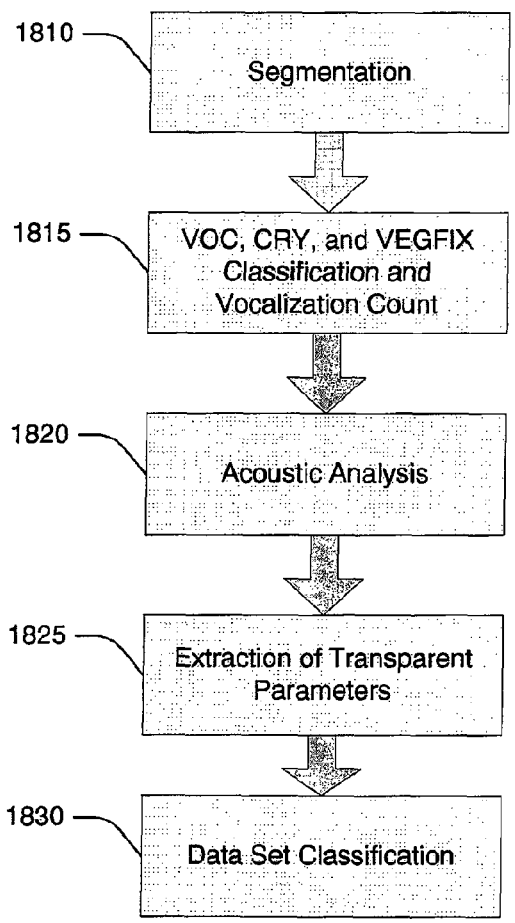
FIG. 17 is a block diagram illustrating one embodiment of a method used to detect disorders or diseases in individuals.
Figure 18:
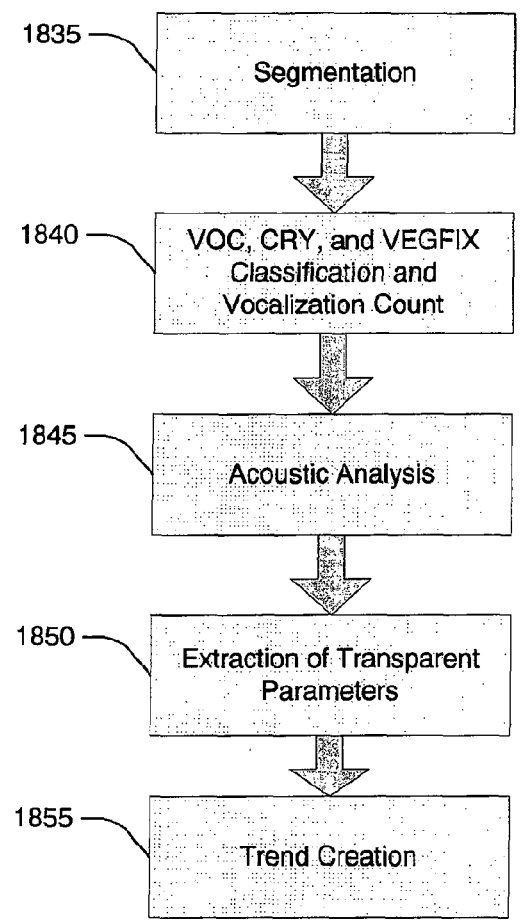
FIG. 18 is a block diagram illustrating one embodiment of a method used to create trends for a population of normal individuals and individuals with the disorder or disease in question.
Figure 19:
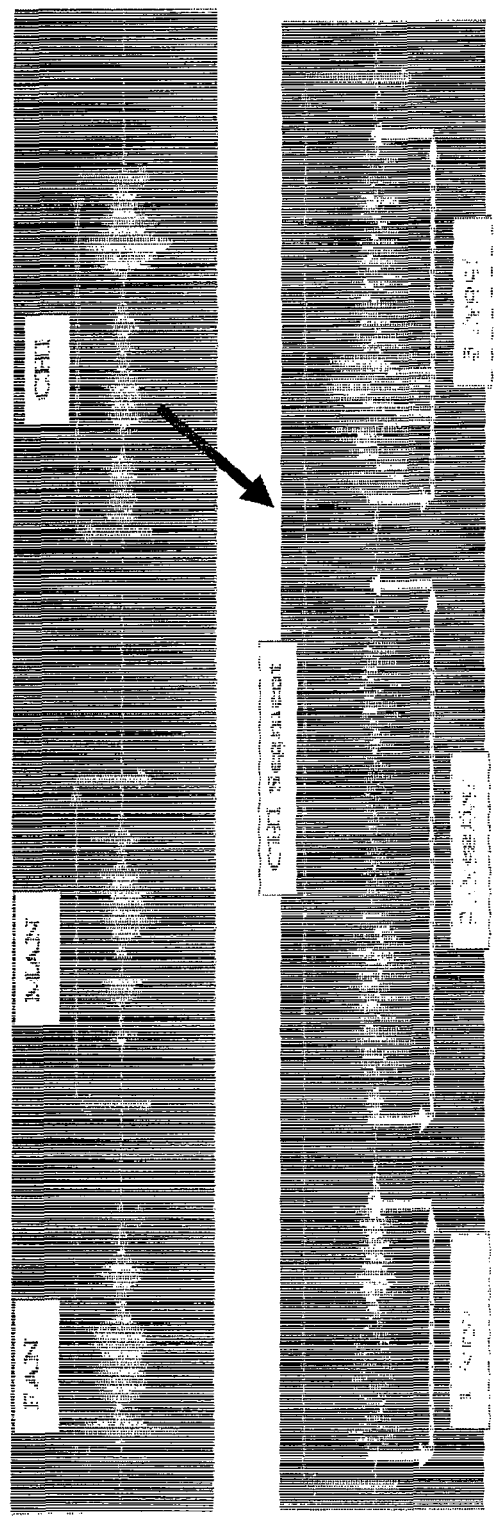
FIG. 19 shows an acoustic signal captured and transformed into a graphical representation.

FIGS. 17 and 18 show a flow chart for a method of detecting autism and a method of creating trends for use in the method of detecting autism, respectively. The segmentation of block 1810 and 1835 is performed as described above in reference to FIG. 4 and block 304. In block 1810, the segmentation is performed on data for an individual key child, and in block 1835 the segmentation is performed on a plurality of recordings of normal, delayed, and autistic children. During segmentation, the speaker is identified for a particular piece of a recording. After the speaker has been identified, the language from the speaker of interest, in this case the key child, is analyzed further. FIG. 19 shows the segmentation process in the top graph and the further break down of key child segments into VOC, CRY, and VEGFIX segments.

The segments identified as belonging to a key child in blocks 1810 and 1835 are then broken down into vocalizations (VOC), cries (CRY), and vegetative-sound and fixed-signal sounds (VEGFIX) in blocks 1815 and 1840 respectively. Vocalizations include various types of speech depending on the age of the child. Between 0 to 4 months, vocalizations include only vowel-like sounds. Around 5 months, a child starts vocalizing marginal syllables which consist of very rudimentary consonant-vowel sequences. Some children make lip-trilling sounds called raspberries, which are also considered as vocalizations. Around seven months, a child's vocalizations may include canonical syllables and repetitive babbles which are well constructed consonant and vowel sequences. At this stage, a child may explore with variation of pitch creating high pitched squeals and low pitched and dysphonated growls. Around a year, a child starts saying isolated words, but keeps babbling too until 18 months or so. By two years, a child will have a fairly large vocabulary of spoken words. In short, vocalizations include all meaningful sounds which contribute to the language development of the child.

Vegetative-sound includes all non-vocal sounds related to respiration and digestion, e.g., coughing, sneezing, and burping. Fixed-signals are sounds which are related to the voluntary reactions to the environment, e.g., laughing, moaning, sighing, and lip smacking. Vegetative-sound and fixed-signal sounds are detected collectively. These types of sounds are eliminated since they do not provide information about linguistic sophistication.

It should be noted that cries are also a type of fixed-signal. Unlike other fixed-signals, cries are very frequent (depending on the age) and convey various emotional feelings and physical needs. Although not performed in this specific method, the analysis of cries according to the described techniques may be used to detect disorders or diseases, since crying is also another means of communication in a baby's life.

Child speech classification is performed by statistical processing using Mel-scale Frequency Cepstral Coefficients (MFCC) and Subband Spectral Centroids (SSC). Other statistical processing techniques may be used.

Using MFCC is a standard state-of-the-art method for automatic speech recognition. Another available type of feature, albeit less popular than MFCC, is SSC. In conventional MFCC features, the power spectrum in a given subband is smoothed out, so that only the weighted amplitude of the power spectrum is kept, while in SSC the centroid frequency of each subband is extracted. SSC's can track the peak frequency in each subband for the speech section, while for the non-speech section it stays at the center of the subband. MFCC is a better feature than SSC by itself, but the combination of MFCC and SSC demonstrates better performance for the automatic speech recognition of adult speech. SSC has been applied for various applications—some of them are listed below:

Adult speech recognition
Speaker authentication or recognition
Timbre recognition of percussive sounds While MFCC is good for extracting the general spectral features, SSC will be useful in detecting the formant peaks. Since formant tracks are found in child vocalizations (although voiced cries may have formant tracks) and not in vegetative-sound/fixed-signal sounds, the formant contours can be tracked in child speech processing.

For child speech processing, a Fixed Boundary Gaussian Mixture Model (FB-GMM) classifiers with 2000 Gaussians are used, i.e., statistical classification is performed for every energy island as identified in the previous stage. The models are created using two sets of features: MFCC and SSC. MFCC's are extracted using 40 filter banks with 36 coefficients. SSC's are created using 7 filter banks to capture the formant peaks only. Since the audio used in this study has a sampling frequency of 16 KHz, filter banks in the range of 300 to 7500 Hz are used. Hence, MFCC-SSC features have dimensions of (36+7=) 43, and with delta information it becomes (43 *2=) 86.

In the context of age dependent modeling, the purpose is to classify three types of speech—vocalizations, cries, and fixed-signal/vegetative-sound sounds. However, these three categories of child speech vary immensely with the variation of age. Hence, one model for the entire age range 0 to 48 months will not serve our purpose. Several studies show that a child's vocal tract may grow from around 5 cm to 12 cm from birth to four years old. Other studies show that formant frequencies are highly dependent on the length of the vocal tract. By the theory of "open tube model of vocal tract", the relationship between $F_i$, i-th formant frequency, and l, the vocal tract length, is given by $$F_i = \frac{c}{4l}(2i - l),$$

where c is the speed of sound in air (moist air inside the mouth, at body temperature, and appropriate pressure). This shows that the larger the vocal tract length, the smaller the formant frequencies. Hence, due to rapid growth of the vocal tract in babies, formant frequencies change and, consequently, the overall speech characteristics change almost every month of age. Hence, three models—/voc/, /cry/, and /vegfix/ are created for each month-age of the child ranging from 0 to 48 months.

Classification is done with prior knowledge of the child's age, by using age dependent vocalization, cry, and fixed-signal/vegetative-sound models.

In blocks 1820 and 1845, acoustic analysis is performed on the VOC islands (recordings corresponding to periods of very high energy bounded by periods of very low energy). The islands within the child segments then are further analyzed using acoustic features. The following acoustic features are extracted from the VOC islands:

1. Duration analysis: It is assumed that every burst of energy which composes the child speech has to be of certain duration to be considered as a meaningful speech (vocalization). For example, if a continuous energy section is more than 3 seconds, it can be assumed that the speech is not a vocalization, but is most likely to be some sort of cry or scream (based on other criteria). FIG. 6 shows an example of a vocalization, which is a series of consonant vowel sequences, (hi-ba-ba-bab-bab). Only the vowels are the high energy parts while the consonants have low energy. The duration of the high energy parts are measured for validation of vocalization.

2. Canonical syllable identification: Formant transitions (mainly for F1 and F2) can be noticed in CV, VC, CVC or VCV sequences. FIG. 6, which is a series of CV and CVC sequences, shows formant transitions from /b/ to the following vowel /a/ and then to /b/. These types of formant movements are indicative of canonical syllables which are part of vocalizations.

Figure 20:
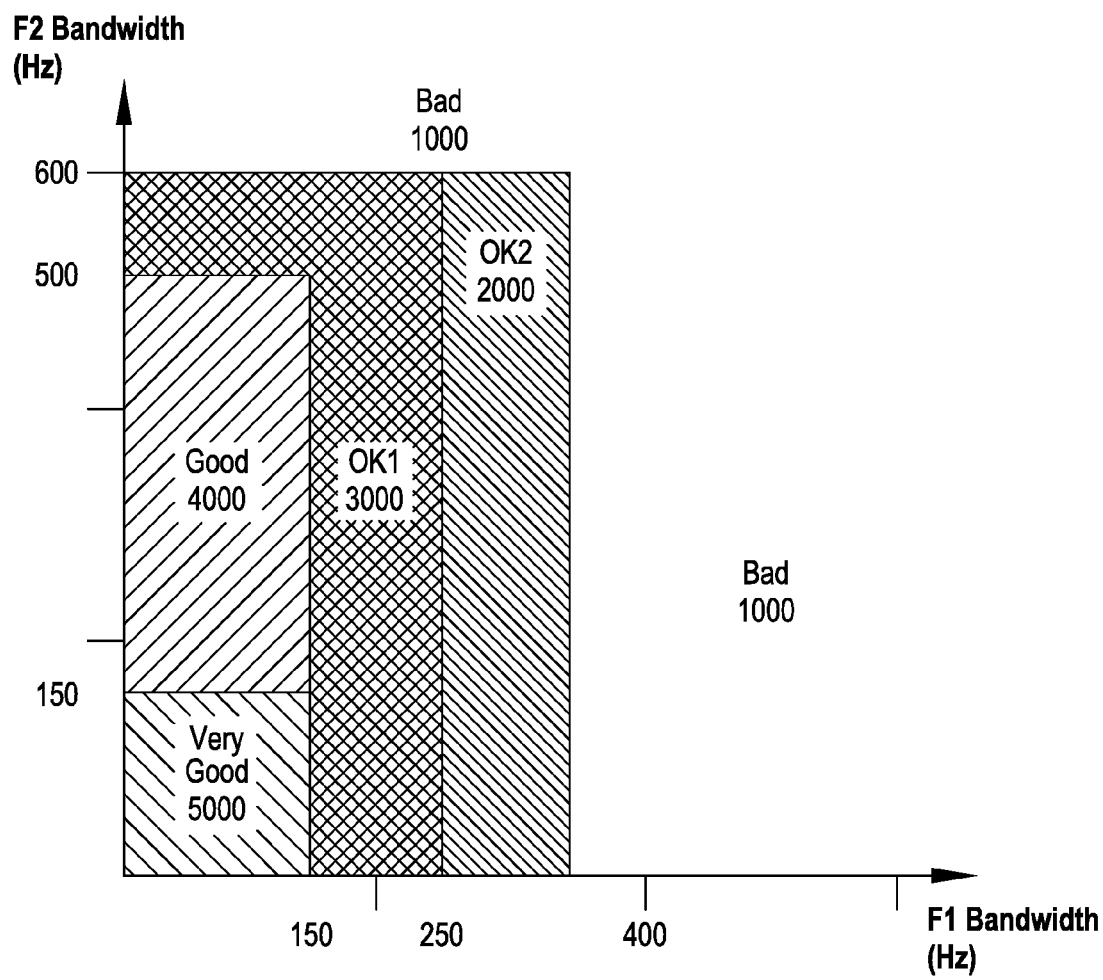
FIG. 20 shows a graphical representation of an empirical display for how the grouping of formant bandwidths can mark the articulation level.

3. Articulation analysis: Formant bandwidths mark the clarity of pronunciation. The narrower the bandwidth, the clearer the speech. It is expected that cries or other fixed-signals (e.g., lip smacking) or vegetative-sound will have wider bandwidths than a true vocalization. FIG. 20 shows an empirical display for how the grouping of F1 and F2 bandwidths can mark the articulation level. A score is assigned to each articulation group based of the "goodness" of each articulation level.

4. Emotional intensity analysis: High intensity speech sounds (e.g., a cry with a full lung of air) are observed to have the first spectral peak above 1500 Hz. Normal vocalizations will have more energy in the lower frequencies (ranging from 300 to 3000 Hz) than higher frequencies (6000 to 8000 Hz). Thus, there will be a 30 dB drop expected from the first part of the spectrum to the end of the spectrum, which is referred to as spectral tilt with a negative slope. For cries, the spectral tilt may not exist, where the spectrum is rather flat. A spectral tilt with a positive slope (low energy in lower frequencies and high energy in higher frequencies) indicates non-vocal sound (e.g., breathing, lip smacking).

5. Dysphonation analysis: It is assumed that normal vocalizations which are mostly composed of vowels makes the spectrum periodic. On the other hand, dysphonated sounds have rather random spectrums with subharmonics in the spectrum. The randomness of the spectrum can be measured by the entropy of the spectrum. The higher the entropy, the more random is the spectrum and the higher the dysphonation.
6. Pitch analysis: Pitch is used to detect squeals and growls. Normal pitch for a child is in the range of 250 to 600 Hz. A vocalization is marked as a squeal if the pitch is more than 600 Hz (it could go up to 3000 Hz). Similarly, growls are vocalizations which have pitch lower than 250 Hz.
7. Intonation analysis: Intonation has a major role in determining the emotion of the child. Squeals and growls are vocalizations only when they are playful and happy. Angry versions of those high- or low pitched and dysphonated sounds are cries. Pitch contours help determine whether the speech is angry or happy. Typically, a rising pitch is an indicator of happy sounds, while a falling pitch is a sad sound.
8. Voicing analysis: It is assumed that vocalizations are mostly composed of vowels, which are voiced speech, with interlaced consonants (unvoiced speech). If an entire speech section is unvoiced, then it is assumed to be some sort of a vegetative-sound/fixed-signal sound (e.g., cough, throat clearing, etc.).

For this analysis, formant peaks and formant bandwidths are detected using Linear Predictive (LP) analysis, while pitch is calculated based on autocorrelations. Finally, formant and pitch contours are extracted by applying a smoothing filter—median filter. Other spectrum analyses are performed using a 1024 point FFT.

In blocks 1825 and 1850 of FIGS. 17 and 18, the transparent parameters are extracted. These parameters are used to determine whether a subject is normative or autistic. FIG. 21 shows acoustic parameters pertinent to the determination of autism. FIGS. 21 and 22 show additional acoustic and non-acoustic parameters that may be extracted from recordings. In the present embodiment, the acoustic parameters depicted in FIGS. 21 and 22 are used for the detection of autism. Alternatively, the non-acoustic parameters depicted in FIG. 22 may be used for the detection of autism. Collectively, these acoustic and non-acoustic parameters are referred to as transparent parameters. It has been shown through utilizing the methodology of the present embodiment that there are differences between the transparent parameters observed in normal, delayed, and autistic children. Generally, the acoustic parameters relate to those vocalizations created by the key child, and non-acoustic parameters are those relating to the interactions, specifically those interactions between the key child and adults, and the environment that the child experiences.

The nine non-acoustic parameters are shown in FIG. 22. The adult vocalization length in seconds refers to the length of adult vocalization on the recording. The adult vocalization count refers to the number of vocalizations made by an adult. The number of child-initiated conversations refers to the number of times a child makes a vocalization and an adult replies. The number of conversational turns refers to the number of times a child responds to an adult vocalization. The number of conversational turns in child-initiated conversations refers to when a child initiates a conversation and then responds to an adult vocalization thereafter. The child vocalization length in seconds in conversational turns refers to the length of time child vocalizations last in conversational turns. The child vocalization counts in conversational turns refer to the number of vocalizations a child makes in a conversational turn (which may indicate the complexity of an answer). The child vocalization length in conversations with an adult is the average vocalization length of a child over a conversation with an adult. The child vocalization counts in conversations with and adult is the number of vocalizations made by a child over a delineated conversation with an adult.

The twelve acoustic parameters shown in FIG. 21 are both theoretically (based on models from 30 years of research in vocal development) and statistically (as indicated by principal components analysis, PCA) clustered into four groupings pertaining to the infrastructure for speech. Each of the 12 parameters are classified as a plus or minus. To adjust for differences in rate of vocalization (volubility) across individual children and recordings as well as differences in lengths of recordings, for each parameter the ratio of the number of vocalizations labeled plus to the number of utterances is taken. This yields a set of 12 numbers (one for each parameter) per recording. This 12-dimensional vector is used to predict vocal development and to classify recordings as belonging to typically developing or autistic children in the analyses.

Figure 23:
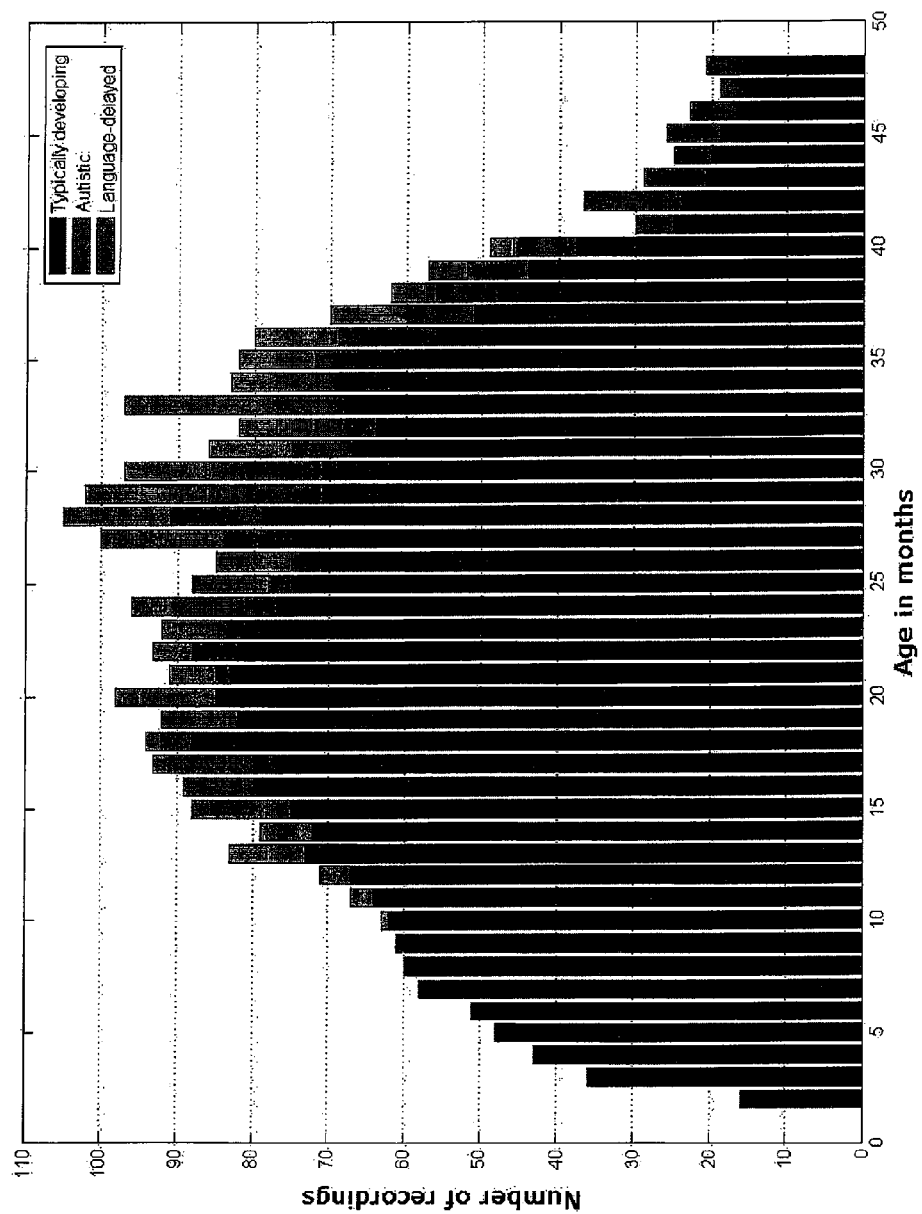
FIG. 23 shows a data set used in developing a model for the detection of autism.

As shown in FIG. 23, a large data set having children with ages spanning age 2-48 months was used. There were 2682 recordings of 328 children in the same set which showed normal development. There were 300 recordings of 30 children which showed delay in language development. There were 225 recordings of 34 children who were diagnosed as autistic. From this data set, the model and trend lines were created.

Figure 24:
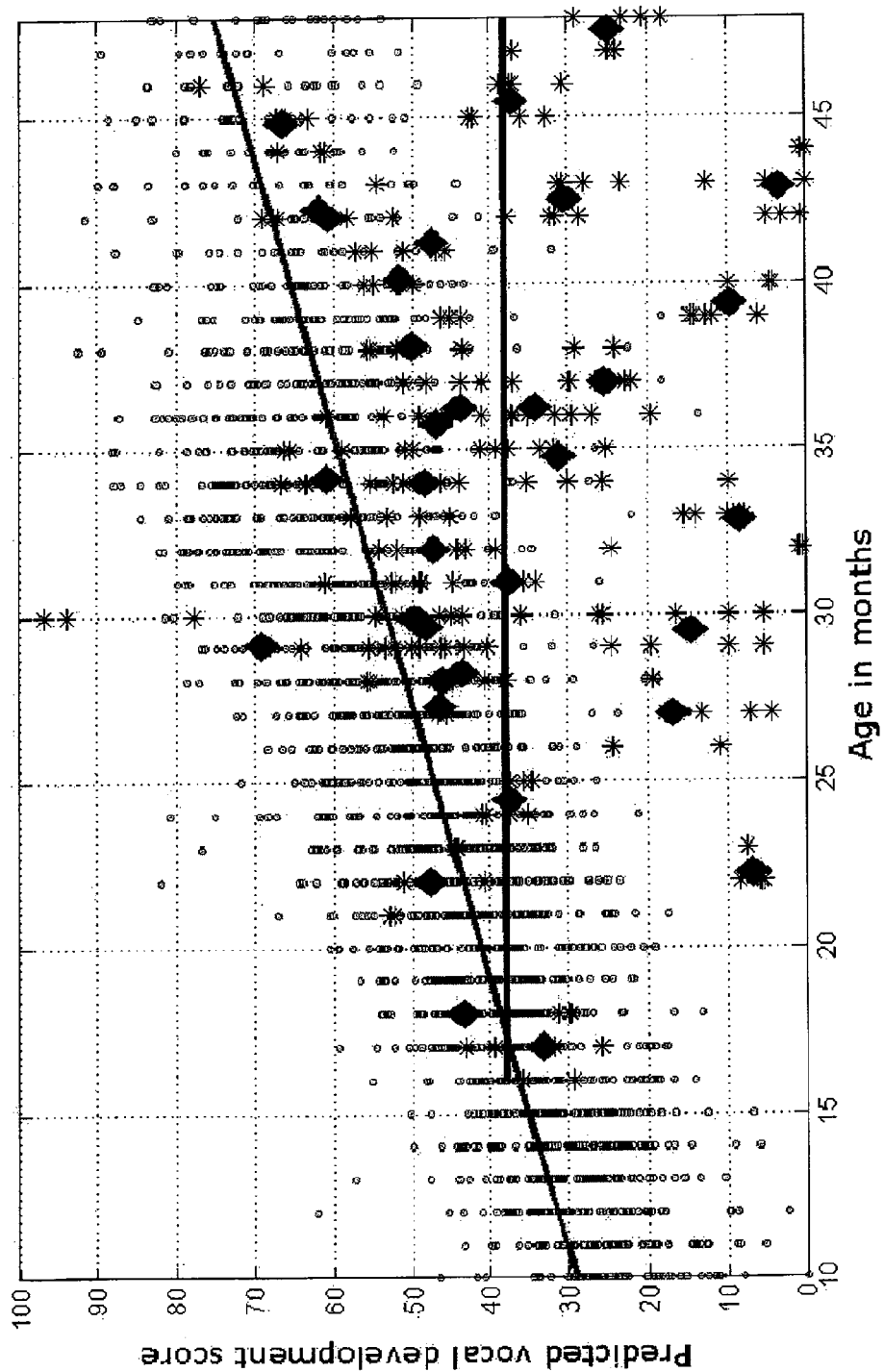
FIG. 24 shows a trend chart for acoustic parameters in autistic and normally developing children.
Figure 25:
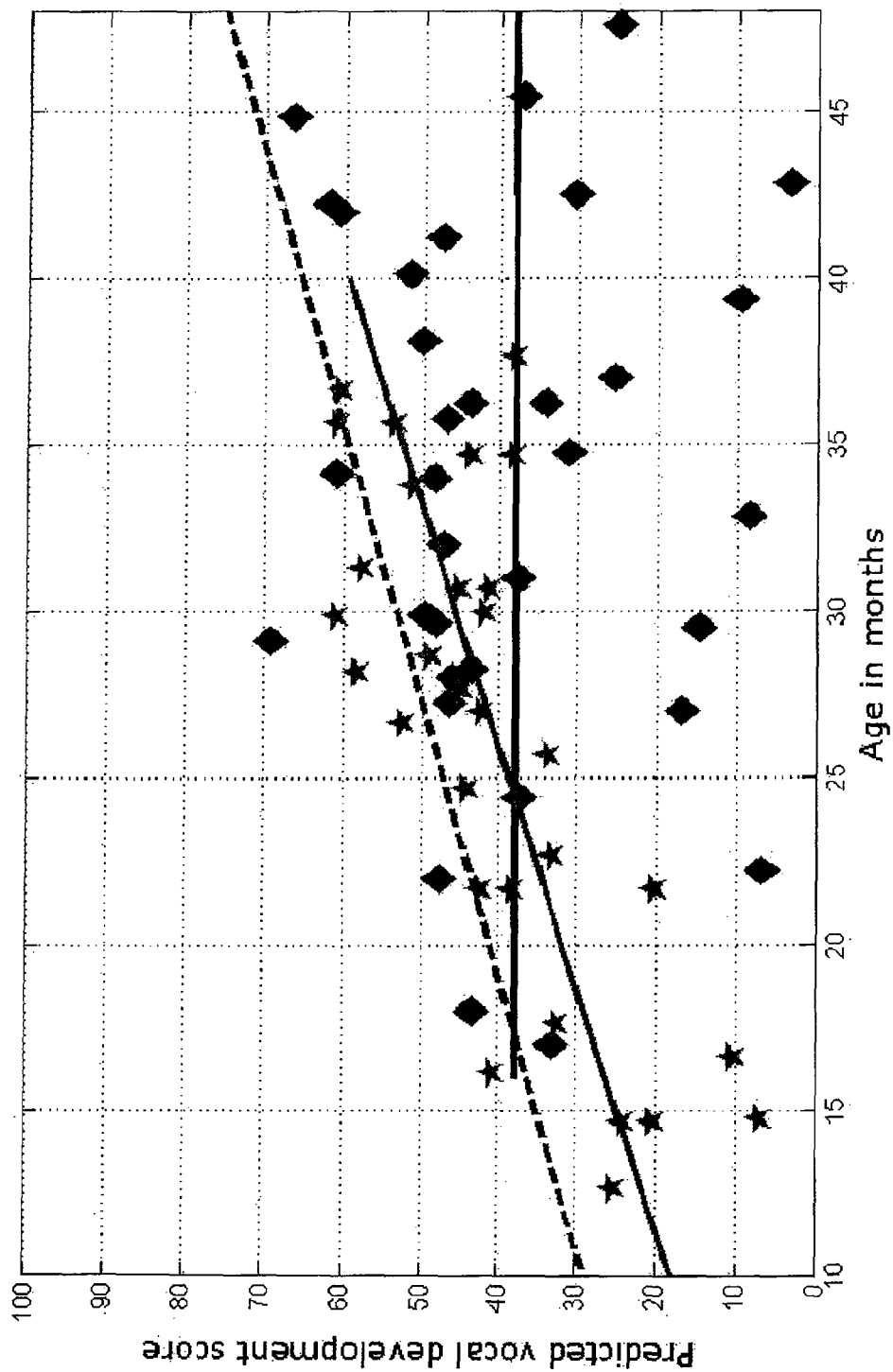
FIG. 25 shows a trend chart for acoustic parameters in autistic, normally developing, and language delayed children.
Figure 26:
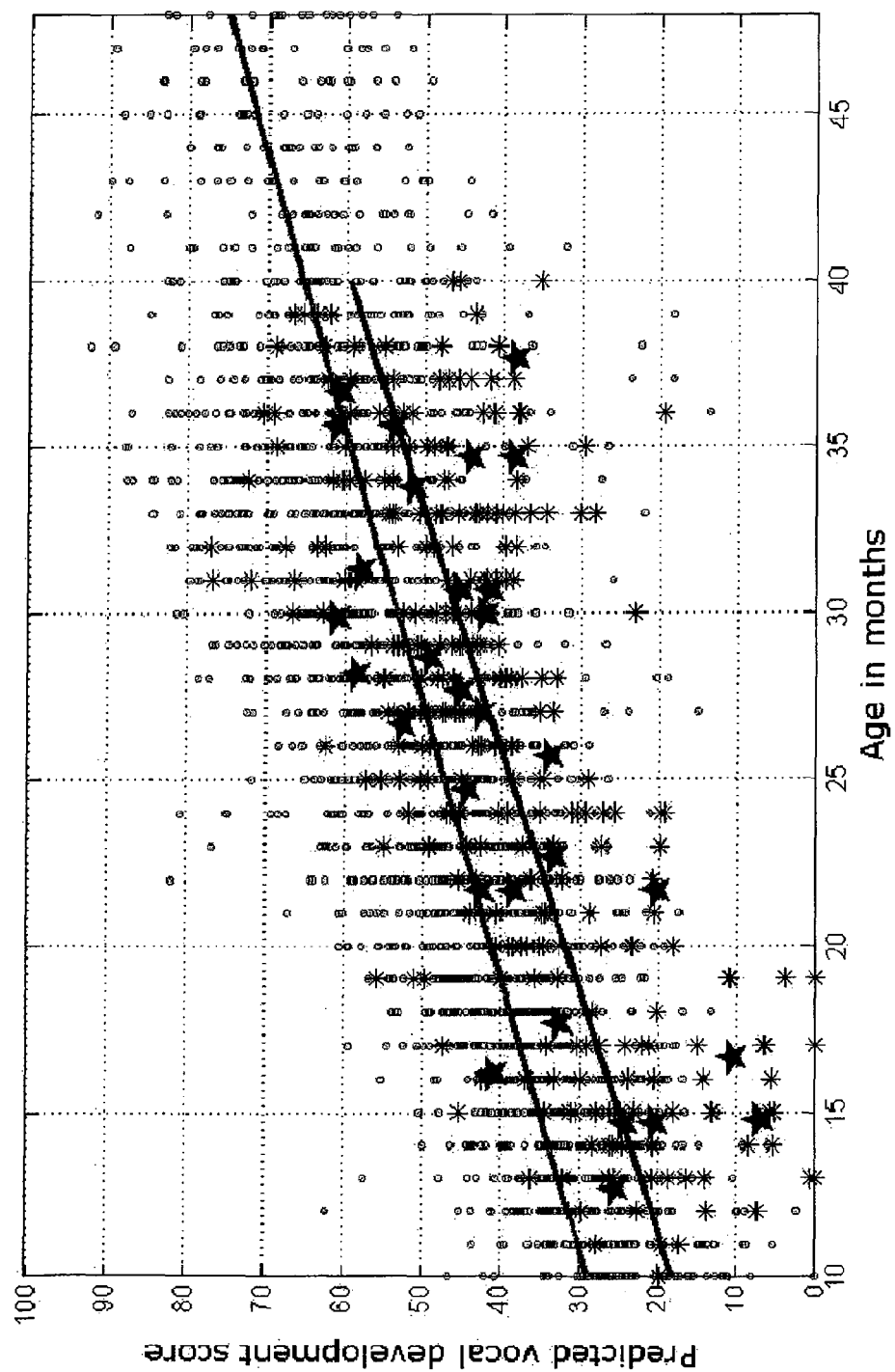
FIG. 26 shows a trend chart for acoustic parameters in normally developing and language delayed children.

In block 1855 of FIG. 18, trends are created based on the recordings collected to be used as a model. A predicted vocal development score is developed based on analysis of transparent parameters as will be explained below. FIGS. 24-29 show trend lines and data points for predicted vocal development scores. FIG. 24 shows a trend chart for acoustic parameters in autistic and normally developing children. The gray dots represent the vocal development scores for normally developing children. The gray line is a trend line for normally developing children. The asterisks represent vocal development scores for autistic children. The diamonds represent the average (based on multiple recordings for a single child) vocal development scores for autistic children. The black trend line is for autistic children. FIG. 25 shows a trend chart for acoustic parameters in autistic, normally developing, and language delayed children. The gray stars represent the average (based on multiple recordings for a single child) vocal development scores for language delayed children. The black diamonds represent the average (based on multiple recordings for a single child) vocal development scores for autistic children. The gray trend line is for language delayed children. The black trend line is for autistic children. The broken trend line is for normally developing children. FIG. 26 shows a trend chart for acoustic parameters in normally developing and language delayed children. The gray dots represent the vocal development scores for normally developing children. The asterisks represent vocal development scores for language delayed children. The black stars represent the average (based on multiple recordings for a single child) vocal development scores for language delayed children. The black trend line is for language delayed children. The gray trend line is for normally developing children.

Figure 27:
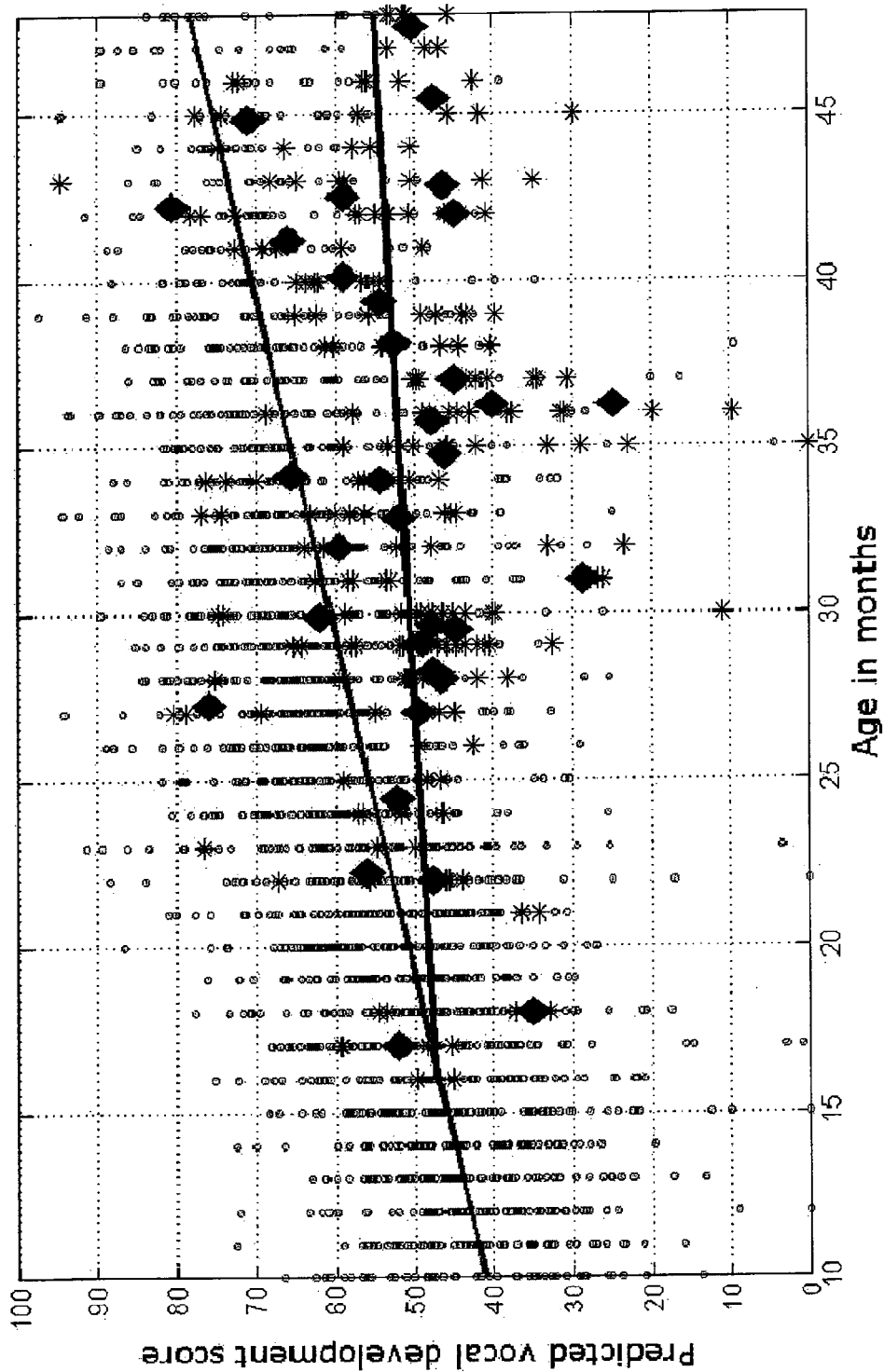
FIG. 27 shows non-acoustic parameters in normal and autistic children.
Figure 28:
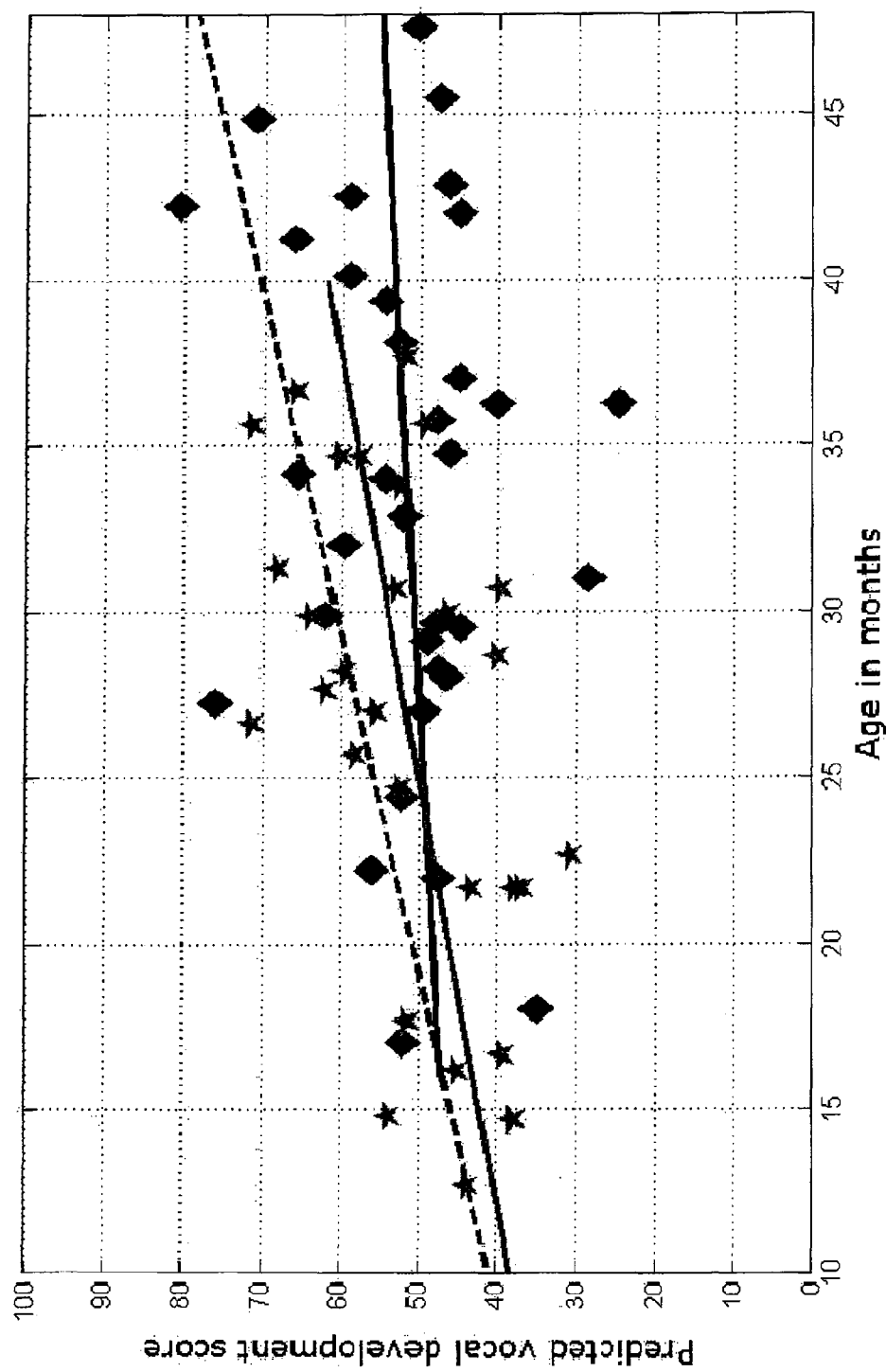
FIG. 28 shows a trend chart for acoustic parameters in autistic, normally developing, and language delayed children.
Figure 29:
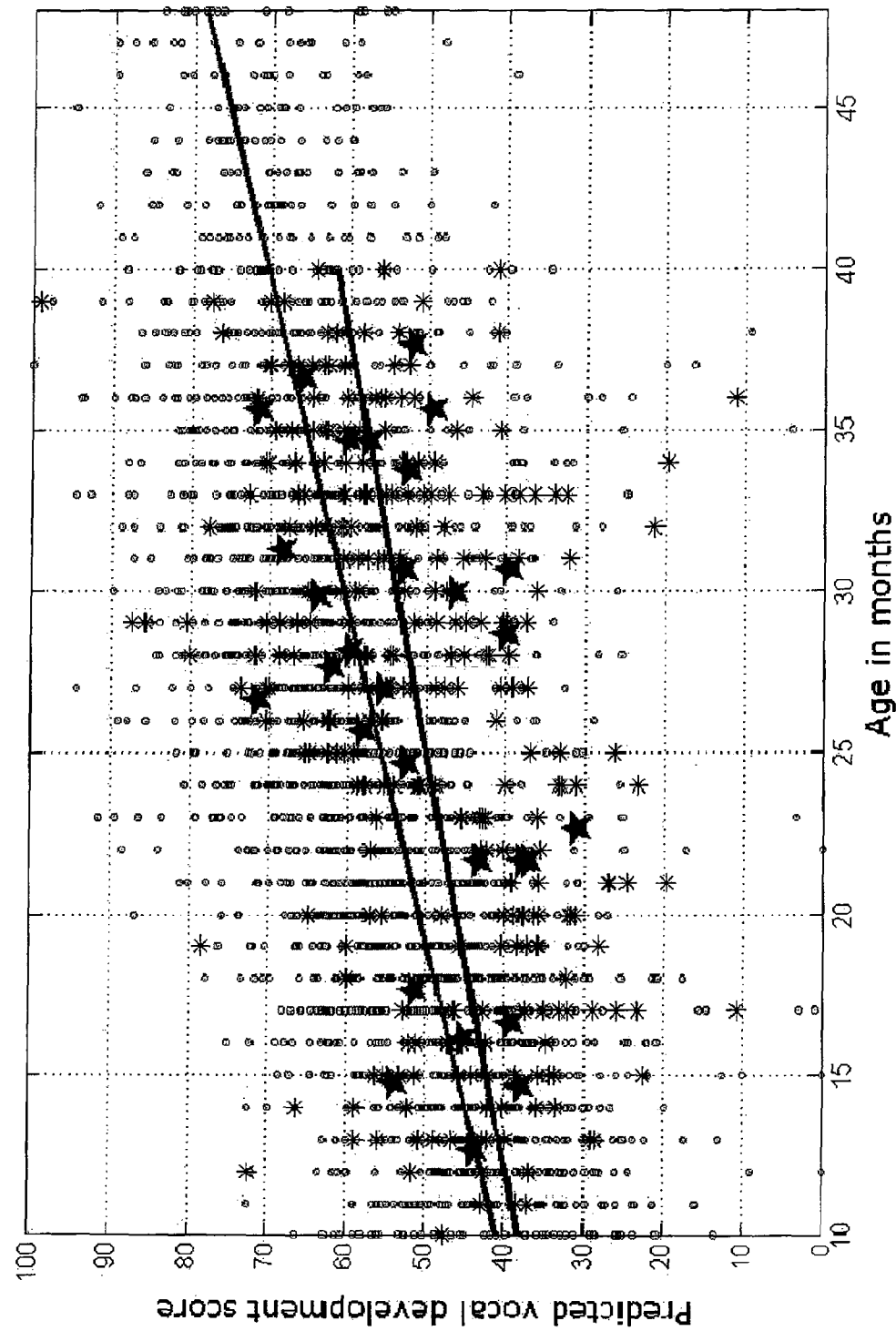
FIG. 29 shows a trend chart for acoustic parameters in normally developing and language delayed children.

FIG. 27 shows non-acoustic parameters in normally developing and autistic children. The gray dots represent the vocal development scores for normally developing children. The gray line is a trend line for normally developing children. The asterisks represent vocal development scores for autistic children. The diamonds represent the average (based on multiple recordings for a single child) vocal development scores for autistic children. The black trend line is for autistic children. FIG. 28 shows a trend chart for acoustic parameters in autistic, normally developing, and language delayed children. The gray stars represent the average (based on multiple recordings for a single child) vocal development scores for language delayed children. The black diamonds represent the average (based on multiple recordings for a single child) vocal development scores for autistic children. The gray trend line is for language delayed children. The black trend line is for autistic children. The broken trend line is for normally developing children. FIG. 29 shows a trend chart for acoustic parameters in normally developing and language delayed children. The gray dots represent the vocal development scores for normally developing children. The asterisks represent vocal development scores for language delayed children. The black stars represent the average (based on multiple recordings for a single child) vocal development scores for language delayed children. The black trend line is for language delayed children. The gray trend line is for normally developing children. As shown in FIGS. 24-29, the predicted vocal development score by employing acoustic or non-acoustic parameters for the population studied can be projected versus the age in months of the child.

The creation of a predicted vocal development score is based on analysis of transparent parameters (including acoustic or non-acoustic). For example, in a case of acoustic parameters, multiple linear regression (MLR) analysis can be conducted to obtain perspective on both development and group differentiation. In one experiment using acoustic parameters (shown in FIG. 21), the 12 acoustic parameter ratios of speech-related vocal islands (SVIs, previously referred to as VOC islands) to speech-related child utterances (SCUs) were regressed within each recording against age for the typically developing sample, yielding a normative model of development with respect to acoustic organization of vocalizations. After the model had been developed, its coefficients were used to calculate developmental scores for the autism and language-delayed recordings. Growth in the developmental scores across age was found for the typically developing sample and the language-delayed sample, but not for the autistic sample, whose developmental scores were also in general considerably below those of the typically developing sample. FIGS. 24-29 show the results of the analysis.

Figure 30:
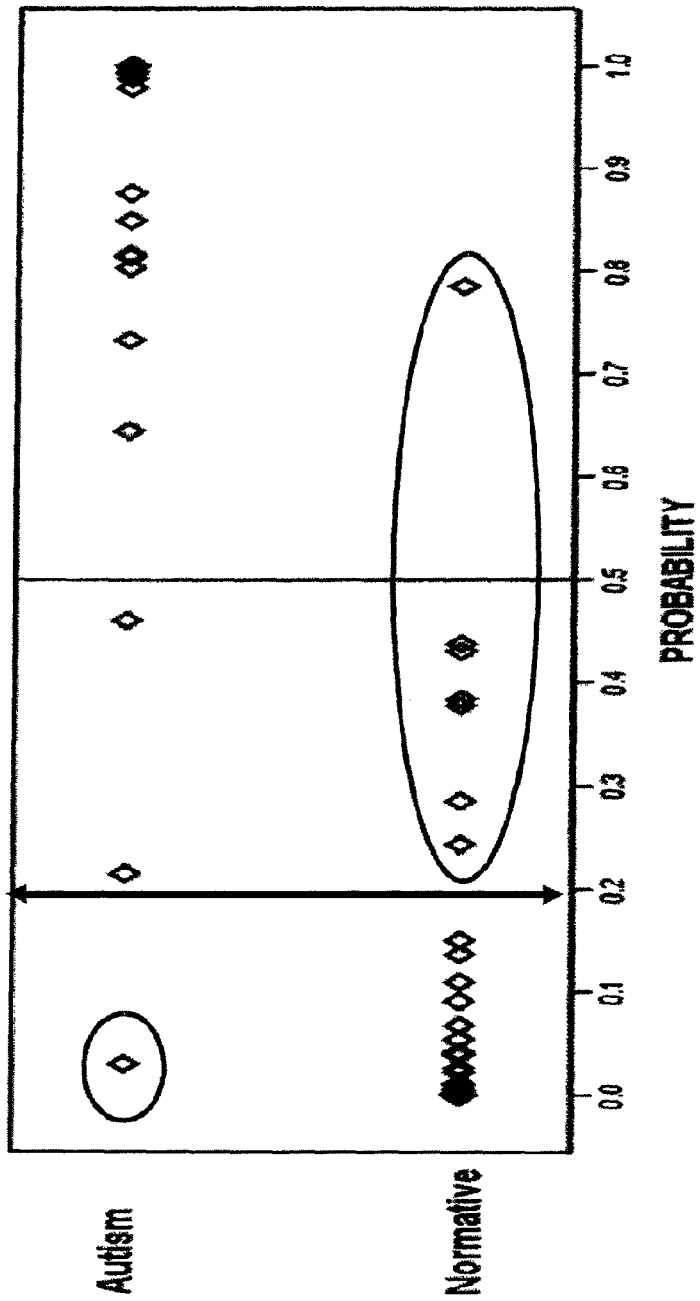
FIG. 30 shows the results of the use of logistical regression analysis in determining normally developing and autistic individuals.

In block 1830 of FIG. 17, the data set related to the key child in question is compared to the trend lines of known subjects in order to make a determination as to whether the individual is autistic, delayed, or normal. As shown in FIG. 30, Logistic Regression Analysis, was used to model optimum classification of children as autistic or non-autistic based on the 12 acoustic parameters. In the case of normally developing children, a high percentage of normal children were identified as normal.

In FIG. 31, a number of tables are shown showing the accuracy of various methodologies of determining the likelihood of autism. Using Logistic Regression and an equal error rate (EER), the method had a high degree of success while only delivering a small number of false positives. For instance, in the case where a probability of 0.98 was used, the system and method determined that 93% of those subjects were considered normal, and only had a small error rate in determining that some normal individuals were autistic. At the same time, only 12% of individuals were determined to be normal when they were really autistic, and 88% of autistic individuals were correctly identified as autistic. The bottom row of tables shows the alternative Linear Discriminant Analysis, and shows similar results.

Although the above system and method is described for application in detecting autism, it may be used in for a number of different diseases and disorders related to speech. Through capturing information concerning trends in the population, processing the information to determine trends, and comparing individuals to those trends, diseases and disorders may be diagnosed. Generally, the model/trend creation functions according to the same principles described in FIG. 18. By segmenting the sound signal in block 1835 to reveal those sounds produced by the subject intended to be studied and then further subdividing the sounds of the subject into at least those sounds that are vocalizations and those sounds that are not in block 1840, the sound signal to be studied can be pinpointed. Then through the acoustic analysis and development of transparent parameters in blocks 1845 and 1850, the features of the sound signals can be revealed. From these features, compared to the prevalence of the disease or disorder in the individuals studied, a trend or model can be created in block 1855 that may be used to compare new subjects in order to determine if they have the disease or disorder. New subjects are processed according to FIG. 17 in a similar fashion and ultimately compared to the trend determined in block 1830. Furthermore, although the above description focuses on vocalization data, as the database of child recordings in a natural language environment grows for children of very young (less than a year) ages, data concerning the cries of children may reveal trends that can allow for the detection of autism.

In an alternative embodiment, autism (and other diseases) may be detected using either solely the above-described phone analysis in relation to child language development or the above-described phone analysis in conjunction with transparent feature analysis. Using frequency of phones or a PCA (principal component analysis) dimension-reduced bi-phone analysis, human SLP assessment scores can be predicted by an embodiment of the above-described system and method. A phone-based feature used for AVA could be used for autism detection with the rest of the system unchanged, including LDA (linear discriminant analysis), logistic regression, etc. The addition of phone-based feature analysis to acoustic transparent feature analysis could provide additional resolution in respect to autism detection. Furthermore, although much of the analysis is focused on vocalizations as the database of child recordings in a natural language environment grows for children of very young (less than a year) ages, data concerning the cries of children may reveal trends.

In one embodiment of a method of detecting autism, a party interested in a detecting autism in a child may request a test system be sent to them. In response, a test system may be sent to them by mail or other delivery means, or may be given to them by a doctor or medical professional. The system includes the recording unit, instructions, and clothing for the subject (the key child) to wear that is adapted to hold the recording unit. The child is then recorded for the specified period and the system is returned by mail or physically returned to a central processing receiver. The central processing receiver, then retrieves the data from the system and processes the data. Reports are returned to the necessary parties which may include the parents of the key child, the physician, other professionals, etc. This method may be implemented in a low cost fashion since the key child or key child's guardian/parent is in effect "renting" the unit for a one time use. After usage the same unit may be reused for another subject who will pay the "rental" fee, collect the needed data, return the unit, and receive the needed test results.

Development of a Child Model and Unsupervised Analysis

As discussed above, some embodiments use automatic speech recognition (ASR) systems designed for adults in order to identify phones for use in determining a child's developmental level. One such ASR is the Sphinx decoder. This decoder and others like it are based on a phone model developed from adult speech. Although the speech of children is similar to that of adults, an ASR designed for adults may not produce optimal phone detection for children. The adult ASR is based on adult speech. The data analyzed is child speech. Therefore, the data from which the model was created may have limitations or inaccuracies when compared to disparate data, e.g., child speech. In order to eliminate data model mismatch, a model created from the analysis of child speech may be used.

Traditionally, a speech model for children could be created by directly training and creating a speech model. This would resolve the data model mismatch. This process would involve a professional listening to child recordings and classifying the phone spoken by the child. However, labeling child speech is a very time consuming and error-prone task, because child speech usually is not well-pronounced and has large variations. Therefore, supervised child speech modeling might be difficult and costly.

Instead, in one embodiment, unsupervised clustering methods could be used for child speech modeling. This method, based on the statistical characteristics of data, clusters similar child speech data together. This methodology may reduce the need for human classification of child speech. Since the above methods are based on statistically comparing the development of a subject to a model for development of known subjects, the actual phones spoken may be excluded from the analysis. Instead, clusters of speech segments that may or may not represent actual phones are developed, and the speech of a subject is compared to these clusters.

One methodology of clustering is a K-means. A brief description of K-means algorithm is given in the following:
1. For a given data set $\{x_i | i=1, \ldots, n\}$, K-means algorithm is trying to find k representative points $\{c_i | i=1, \ldots, k\}$, where k is smaller (or much smaller) than n. $c_i$ are cluster centroids or cluster means. This is why it is called K-means.
2. Initializing $c_i$. This could be done by randomly choosing from a data set or by other methods.
3. For each data point $x_i$, find the closest cluster by measuring the distance to each cluster centroid, and label this data point as that cluster.
4. For each cluster, pool all the data points labeled as this cluster and calculate the mean of this cluster. Update the cluster centroid with the new calculated mean.
5. Iterate step 3 and step 4 until some convergence criterion is met (theoretically, the iteration is guaranteed to converge to at least the local minimum of smallest overall data "distortion").

The obtained clusters of child speech are considered to resemble phones, and analysis is performed according to the above uni-phone or bi-phone analysis substituting the cluster model for the ASR adult model. Child speech could be decoded with cluster models (centroids) to find out the cluster label sequence of child speech. This is much like the phone-decoding process using the adult-phone model. The cluster label sequence, then, could be used in the same way as the phone sequence used in AVA analysis.

Figure 32:
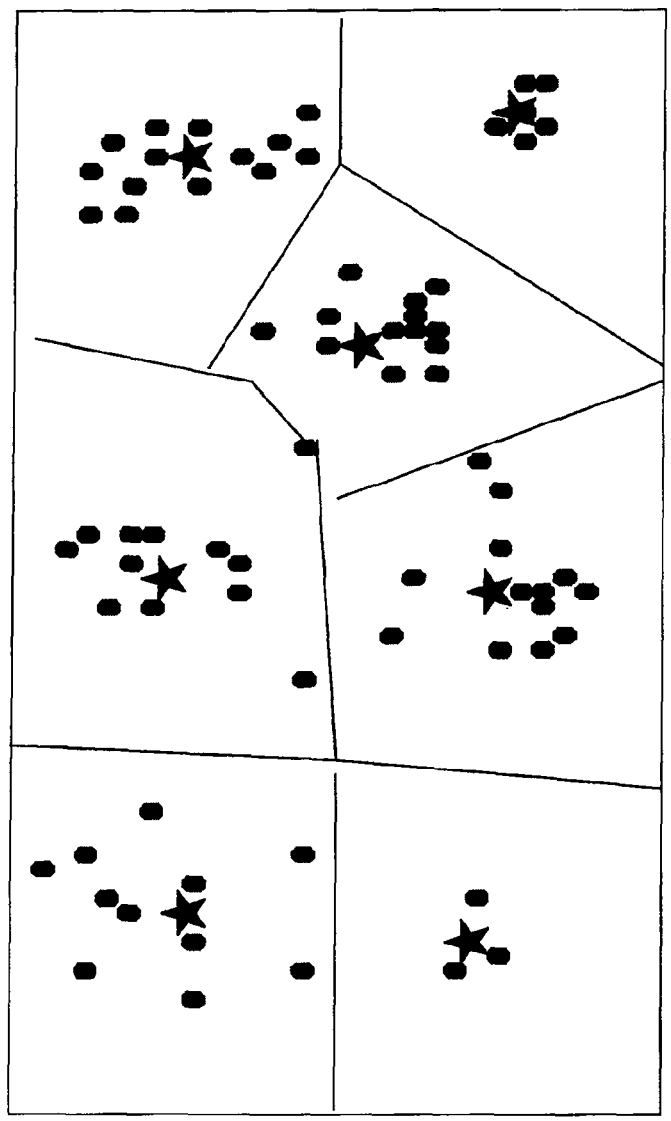
FIG. 32 shows an illustration of K-means clusters.

FIG. 32 shows an illustration of K-means clusters (centroids). As shown in the figure, dots represent data points, stars represent cluster means (centroids), and black lines illustrate the boundaries in the feature space among different clusters which are defined by cluster means (centroids). A K-means algorithm will automatically find optimal "stars" given "dots". The "optimal" is in the sense of minimum distortion (at least locally).

Table 1 below shows experimental results based on an unsupervised child model.

TABLE 1

Adult Model And Unsupervised Child Model Comparison

| | Modeling Detail | Correlation between human SLP scores and machine scores (leave one out cross-validation) |
|---|---|---|
| Adult Model (Sphinx) | Uni-phone | 0.718 |
| | Bi-phone with PCA (50 feature after PCA) | 0.746 |
| Unsupervised Child Model | 64-cluster (uni-phone-way) | 0.730 |
| | 64-cluster-for-above-15-month and 16-cluster-for-below-15 (uni-phone-way) | 0.744 |

The above table shows essentially the same performance of unsupervised method as the one using an adult phone model. This is a verification of previous analysis using an adult phone model. At the same time, this also shows the promise and potential of unsupervised method because it may be more flexible in terms of number of clusters to choose, etc. Although particular numbers of clusters are shown, the optimal number of clusters for a given data set may depend on the size of the data set and various numbers of clusters may be used.

Furthermore, cluster-based feature analysis can be used for autism detection or the detection of other disorders/diseases. Again, the combination of cluster-based feature, adult-phone-model-based feature, acoustic-transparent feature could be done towards autism detection. Currently, in the case of autism detection, transparent features are used in the analysis. Referring to FIG. 21, a table of acoustic parameters is shown. The acoustic parameters shown are extracted from recordings. However, these acoustic parameters are based on real word observations and not clustering. In an alternative cluster-based transparent parameter analysis, clusters are developed in relation to the characteristics of speech and sound. These characteristics may include the pitch of the sound, the duration of the sound, the rhythm of the sound, the organization of the sound, etc. For instance, in the case of sound duration, the acoustic parameters shown have definitions for short, medium, long, and extra-long duration islands. Instead, these definitions may be established by clustering of actual sound recordings and will create a cluster model representative of the data collected.

In this way, the model developed may be finely tuned according to specific age and any other characteristics that are known about the population representing the recording data upon which the model is based. On a most basic level, the characteristics of speech primarily consist of the pitch of the speech, the duration of the speech, and organization of the speech. Clustering can be done according to any and all of these characteristics alone and in combination. Additional speech characteristics may include speech flow, loudness, intonation, and intensity of overtones. Speech flow includes the production speed of utterances and the length of breaks in speaking. Loudness is the amount of energy associated with the speech. Intonation relates to rise and fall in pitch with respect to the speaker's mean vocal pitch. Overtones include higher tones which accompany fundamental tones and are generally fainter than the fundamental tone. All of these characteristics and more can be used to form clusters.

Clustering allows for analysis in the absence of preconceived notions about the characteristics of speech and may reveal patterns previously unrecognized. As long as the sample collected is large enough (statistically speaking), the patterns revealed through clustering will hold true for a population and may be applied to any type of speech analysis in terms of development, detection of disease and disorder (such as autism), and other characteristics of speech, such as emotion, the speaker's underlying motivations, veracity, for example.

Emotion/Stress Detection

Figure 33:
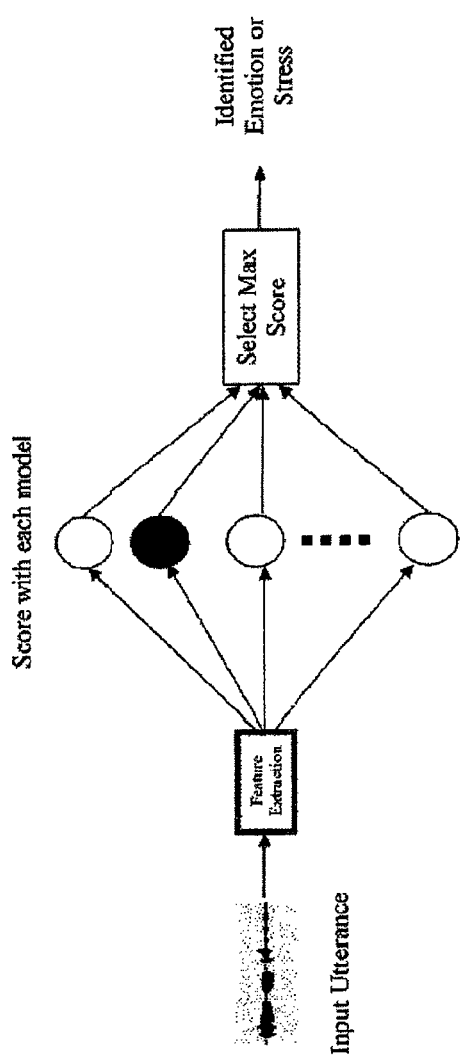
FIG. 33 shows a methodology for determining emotion in an utterance.

It is theorized that the emotions expressed by parents and caregivers may affect the language development of children. The above-described methods and systems lend themselves well to determining the effect of emotion on child language development. One embodiment of a methodology for determining emotion in an utterance is shown in FIG. 33. For purposes of the analysis, it is assumed that one utterance contains only one type of emotion, or in stress detection case, is either stress or neutral (non-stress). When input utterance is received, emotion-related acoustic feature is extracted. Mel-frequency cepstral coefficient (MFCC) and Perceptual Minimum Variance Distortionless Response (PMVDR) may be used as the feature for emotion detection. Once the feature is extracted, the utterance is scored upon the feature in respect to a plurality of models representing emotions. The model having the maximum score is selected, and the emotion associated with that model is identified as the emotion status of the utterance. A Gaussian Mixture Model (GMM) may be used for the scoring, which is described above for segmentation and segment-ID task. In the context of emotion detection, the detection of a stressed or non-stressed condition may be simpler than specific emotion detection and, thus, may be more accurate. This methodology may be performed using the speech detection and analysis system described herein.

In order to experiment with the described method and system and to optimize the model size and feature size, emotion data is needed. A free German emotion database was used, available via the Internet. Twenty full-day natural home environment recordings from 20 different ordinary American families were processed according to the above-described segmentation and ID system, annotated the automatically detected adult utterances for stress and non-stress detection, and obtained about 900 human confirmed stress/non-stress-labeled utterances for this purpose. The data set is called LENA-Emotion-Data-1. The described emotion database is unique and valuable for emotion detection research and development in a natural home environment and how emotion may affect child speech and language development. The system for speech collection described in the '520 application allows for collection of speech in the natural language environment, and processing techniques described above provide for filtering and segmentation of the recorded sound signal.

With the German emotion database, MFCC, PMVDR and GMM, optimal model size and feature size were searched. For model size, with a fixed 36-order-MFCC and its derivative feature (or delta feature, total 72-dimension), optimal GMM size was searched. As shown in Table 2, 128 Gaussians for each emotion GMM model gave the best detection rate for the task of all emotion detection (64.57%) and stress-v.-non-stress detection (89.83%). With the fixed 128 Gaussians per GMM model size, MFCC feature size was further optimized. As shown in Table 3, MFCC feature size of 12 (MFCC+its-delta=24 dimension) gave the best detection rate on the German database. PMVDR was also compared with MFCC for emotion detection task. The experiment result is shown in Table 4.

TABLE 2

Model size optimization, Detection Rate v. number of Gaussians per model

| | # Gaussians/model | | | | | |
|---|---|---|---|---|---|---|
| | 8 | 16 | 32 | 64 | 128 | 256 |
| ALL Emotions | 56.44% | 56.81% | 60.79% | 64.22% | 64.57% | 60.69% |
| Stress v. Non-stress | 84.37% | 84.57% | 88.13% | 88.79% | 89.83% | 88.67% |

TABLE 3

MFCC feature size for emotion detection on German database

| | Feature Size | | | | | | | |
|---|---|---|---|---|---|---|---|---|
| | 12 | 14 | 16 | 18 | 20 | 22 | 24 | 26 |
| All Emotions | 66.76 | 69.92 | 70.39 | 69.53 | 70.11 | 72.92 | 73.36 | 69.69 |
| Stress v. Non-stress | 88.88 | 91.09 | 90.94 | 90.32 | 90.59 | 92.71 | 92.68 | 91.34 |

TABLE 4

Different Feature for Emotion Detection on German database

| | MFCC (24) | PMVDR (24) |
|---|---|---|
| All Emotions | 73.36 | 73.80 |
| Stress v. Non-stress | 92.68 | 93.16 |

To incorporate more information about emotion in the feature used, the dimension of feature needs to be increased to include more relevant characteristics. This may be done by using higher orders of MFCC or PMVDR and including more context (or neighboring) feature frames to cover dynamics of speech which may be associated with emotion. However, increasing the feature dimension may not necessarily improve the detection rate. The reason is that the increased feature dimension may result in the model size increase and thus intensify the conflict between model size and limited amount of training data. Although increasing feature size may incorporate more useful information, increasing the feature size could also introduce some irrelevant features or noise. This could make the modeling process even harder to converge to relevant characteristics of input features. To resolve this issue, Linear Discriminant Analysis (LDA) is used to reduce the feature dimension to reserve the most relevant information from high or very high dimensional features. Alternatively, other forms of analysis that can reduce the dimensionality are used, including feature extraction and feature selection techniques. A simple test in Table 5 showed that LDA helps to reduce the feature dimension and model size and eventually improve the emotion detection rate.

TABLE 5

Simple Test of LDA for emotion detection on German database

|  | 12-dimension MFCC | 6-dimension of LDA |
|---|---|---|
| All Emotions | 58.41 | 58.39 |
| Stress v. Non-stress | 84.72 | 85.30 |

The output dimension of standard LDA may be confined by the total number of classes involved (actually the maximum number of output feature for standard LDA is J−1 if there are J classes). For stress-v.-non-stress detection, the standard LDA can only have one output feature, which may not be good enough. To resolve this issue, sub-class LDA was proposed. For each class, different sub-classes (or clusters) could be obtained using, e.g., K-means algorithm which is described earlier. Since this is basically an unsupervised method, each class can have as many sub-classes as needed. Once sub-classes are generated for each class, the total number of sub-class-pair between each class-pair could be very large, resulting in the number of LDA output virtually unconfined. With this method, experiments were done on German database. Table 6 shows the comparative result, confirming that LDA improves the emotion detection performance.

TABLE 6

Sub-Class LDA Emotion Detection Result on German database

|  | 24-dimension MFCC | 34-dimension of LDA |
|---|---|---|
| All Emotions | 73.36 | 75.62 |
| Stress v. Non-stress | 92.68 | 94.82 |

24-dimension MFCC: The best MFCC result obtained.
34-dimension of LDA: each class has 5 sub-classes, and 7 context frames were used in LDA The German database is acted emotion data. Infoture LENA-Emotion-Data-1 comes from a real natural home environment in an unobtrusive way. To test ideas and methods for emotion detection on Infoture LENA-Emotion-Data-1 may be interesting since the Infoture LENA-Emotion-Data-1 was collected in a natural language environment. Initially, the model trained with the German database was applied on LENA-Emotion-Data-1 for stress/non-stress detection. The detection rate is 51%, similar to random guessing. This is probably due to the mismatch between the LENA-Emotion-Data-1 and the model trained from the German database. To resolve this issue, models trained on LENA-Emotion-Data-1 is directly tested on LENA data. However, to deal with the limited amount of LENA data, leave-one-recording-out-cross-validation was used to take advantage of labeled LENA-Emotion-Data-1 available, while there is no single testing recording family involved in the training of its testing model. This gives the results shown in Table 7, confirming that the current method is feasible for the real natural home environment data like LENA-Emotion-Data-1 for stress detection.

TABLE 7

Leave-one-recording-out-cross-validation on LENA-Emotion-Data-1

| Feature Used | MFC-12 | MFC-40 |
|---|---|---|
| Stress Detection Rate | 68.6% | 70.5% |

An indication as to the emotion of responses and interactions that the child has may be valuable in gaining greater resolution into a child's language development and how to further improve a child's natural language environment. The present systems and methods are well positioned to perform such analysis due to their non-intrusive nature.

The foregoing description of the embodiments of the invention has been presented only for the purpose of illustration and description and is not intended to be exhaustive or to limit the invention to the precise forms disclosed. Numerous modifications and adaptations are apparent to those skilled in the art without departing from the spirit and scope of the invention.

What is claimed is:

1. A method of assessing expressive language development of a key child, comprising:
processing an audio recording taken in a language environment of the key child to identify segments of the audio recording that correspond to vocalizations of the key child;
applying an adult automatic speech recognition phone decoder to the segments to identify each occurrence of a plurality of bi-phone categories and to determine a frequency count for each of the plurality of bi-phone categories, wherein each of the plurality of bi-phone categories corresponds to a pre-defined sequence of two phonemes, and wherein the plurality of bi-phone categories are a first subset of the vocalizations of the key child;
determining a frequency distribution for the plurality of bi-phone categories based on the frequency counts for the plurality of bi-phone categories; and
using the frequency distribution for the plurality of bi-phone categories in an age-based model to assess the expressive language development of the key child, wherein the age-based model is selected based on a chronological age of the key child and the age-based model includes a plurality of different weights associated with the plurality of bi-phone categories.

2. The method of claim 1, wherein applying the adult automatic speech recognition phone decoder comprises identifying occurrences of a plurality of non-phone categories, wherein each of the plurality of non-phone categories corresponds to a pre-defined non-speech sound, and wherein the plurality of non-phone categories are a second subset of the vocalizations of the key child.

3. The method of claim 1, wherein there is a correlation between the frequency count for each of the plurality of bi-phone categories to chronological age.

4. The method of claim 1, wherein the age-based model is based on an age in months.

5. The method of claim 1, wherein the age-based model is an adjustment of the chronological age of the key child.

6. The method of claim 1, wherein using the frequency distribution for the plurality of bi-phone categories in the age-based model to assess the expressive language development of the key child comprises computing an estimated developmental age for the key child based at least in part on the plurality of different weights associated with the plurality of bi-phone categories.

7. The method of claim 6 further comprising using the estimated developmental age for the key child to determine an estimated mean length of utterance for the key child.

8. The method of claim 6 further comprising:
processing, using an audio engine, at least one additional audio recording taken in the language environment of the key child to identify additional segments that correspond to the vocalizations of the key child;

applying the adult automatic speech recognition phone decoder to the additional segments to identify each occurrence of each of the plurality of bi-phone categories and to determine an additional frequency count for each of the plurality of bi-phone categories;

determining an additional frequency distribution for the plurality of bi-phone categories based on the additional frequency counts for the plurality of bi-phone categories;

using the additional frequency distribution in the age-based model to assess the expressive language development of the key child and to generate an additional estimated developmental age for the key child based at least in part on the plurality of different weights associated with the plurality of bi-phone categories; and averaging the estimated developmental age and the additional estimated developmental age.

9. The method of claim 1, wherein:

applying the adult automatic speech recognition phone decoder comprises identifying occurrences of a plurality of non-phone categories, wherein each of the plurality of non-phone categories corresponds to a pre-defined non-speech sound, and wherein the plurality of non-phone categories are a second subset of the vocalizations of the key child;

the age-based model is an adjustment of the chronological age of the key child; and the age-based model is based on an age in months.

10. The method of claim 1 further comprising:

computing a standard score and a developmental age for the key child; and generating an output comprising at least one of: the standard score or the developmental age.

11. A system for assessing expressive language development of a key child, comprising:

a processor-based device comprising an audio engine for processing an audio recording taken in a language environment of the key child to identify segments of the audio recording that correspond to vocalizations of the key child;

an adult automatic speech recognition phone decoder for processing the segments that correspond to the vocalizations of the key child to identify each occurrence of a plurality of bi-phone categories and to determine a frequency count for each of the plurality of bi-phone categories, wherein each of the plurality of bi-phone categories corresponds to a pre-defined sequence of two phonemes, and wherein the plurality of bi-phone categories are a first subset of the vocalizations of the key child; and an expressive language assessment component configured to determine a frequency distribution for the plurality of bi-phone categories based on the frequency counts for the plurality of bi-phone categories and configured to use the frequency distribution for the plurality of bi-phone categories in an age-based model to assess the expressive language development of the key child, wherein the age-based model is selected based on a chronological age of the key child and the age-based model includes a plurality of different weights associated with the plurality of bi-phone categories.

12. The system of claim 11, wherein:

the expressive language assessment component is further configured to compute a standard score and a developmental age for the key child; and the system further comprises:

an output component configured to receive the standard score and the developmental age for the key child and configured to generate an output comprising at least one of: the standard score or the developmental age.

13. The system of claim 11, wherein:

the adult automatic speech recognition phone decoder is further configured to identify occurrences of a plurality of non-phone categories, wherein each of the plurality of non-phone categories corresponds to a pre-defined non-speech sound, and wherein the plurality of non-phone categories are a second subset of the vocalizations of the key child.

14. The system of claim 11, wherein there is a correlation between the frequency count for each of the plurality of bi-phone categories to chronological age.

15. The system of claim 11, wherein the age-based model is based on an age in months.

16. The system of claim 11, wherein the age-based model is an adjustment of the chronological age of the key child.

17. The system of claim 11, wherein the expressive language assessment component is further configured to compute an estimated developmental age for the key child based at least in part on the plurality of different weights associated with the plurality of bi-phone categories.

18. The system of claim 17, wherein the expressive language assessment component is further configured to use the estimated developmental age for the key child to determine an estimated mean length of utterance for the key child.

19. The system of claim 17, wherein:

the audio engine is further configured to process at least one additional audio recording taken in the language environment of the key child to identify additional segments that correspond to the vocalizations of the key child;

the adult automatic speech recognition phone decoder is further configured to be applied to the additional segments to identify each occurrence of each of the plurality of bi-phone categories and to determine an additional frequency count for each of the plurality of bi-phone categories; and the expressive language assessment component is further configured to perform:

determining an additional frequency distribution for the plurality of bi-phone categories based on the additional frequency counts for the plurality of bi-phone categories;

using the additional frequency distribution in the age-based model to assess the expressive language development of the key child and to generate an additional estimated developmental age for the key child based at least in part on the plurality of different weights associated with the plurality of bi-phone categories; and averaging the estimated developmental age and the additional estimated developmental age.

20. The system of claim 11, wherein:

the adult automatic speech recognition phone decoder is further configured to identify occurrences of a plurality of non-phone categories, wherein each of the plurality of non-phone categories corresponds to a pre-defined non-speech sound, and wherein the plurality of non-phone categories are a second subset of the vocalizations of the key child;

the age-based model is an adjustment of the chronological age of the key child; and the age-based model is based on an age in months.

\* \* \* \* \*